(12) United States Patent
Foguet et al.

(10) Patent No.: US 12,409,112 B2
(45) Date of Patent: Sep. 9, 2025

(54) PRESSURIZED NANOEMULSION

(71) Applicant: Biofrontera Bioscience GmbH, Leverkusen (DE)

(72) Inventors: Montserrat Foguet, Leverkusen (DE); Mirella Gwarek, Leverkusen (DE); Lars Möllmann, Leverkusen (DE)

( * ) Notice: Subject to any disclaimer, the term of this patent is extended or adjusted under 35 U.S.C. 154(b) by 0 days.

(21) Appl. No.: 18/533,521

(22) Filed: Dec. 8, 2023

(65) Prior Publication Data

US 2024/0335360 A1    Oct. 10, 2024

(51) Int. Cl.
| | | |
|---|---|---|
| A61K 8/06 | (2006.01) | |
| A61K 9/107 | (2006.01) | |
| A61K 31/197 | (2006.01) | |
| A61K 47/10 | (2017.01) | |
| B82Y 5/00 | (2011.01) | |

(52) U.S. Cl.
CPC .......... *A61K 8/068* (2013.01); *A61K 9/1075* (2013.01); *A61K 31/197* (2013.01); *A61K 47/10* (2013.01); *A61K 2800/30* (2013.01); *A61K 2800/592* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,891,490 | A | 4/1999 | Merabet |
| 6,165,500 | A | 12/2000 | Cevc |
| 6,245,349 | B1 | 6/2001 | Yiv et al. |
| 6,274,150 | B1 | 8/2001 | Simonnet et al. |
| 6,375,960 | B1 | 4/2002 | Simonnet et al. |
| 6,413,527 | B1 | 7/2002 | Simonnet et al. |
| 6,500,862 | B1 | 12/2002 | Zanello |
| 6,559,183 | B1 | 5/2003 | Schmid et al. |
| 6,602,511 | B2 | 8/2003 | Von Corswant |
| 6,897,238 | B2 | 5/2005 | Chen et al. |
| 7,314,624 | B2 | 1/2008 | Baker et al. |
| 11,540,981 | B2 | 1/2023 | Roca et al. |
| 2002/0155084 | A1 | 10/2002 | Roessler et al. |
| 2003/0148927 | A1 | 8/2003 | Patt et al. |
| 2003/0167033 | A1 | 9/2003 | Chen et al. |
| 2003/0190347 | A1 | 10/2003 | Supersaxo et al. |
| 2005/0158389 | A1 | 7/2005 | Domb |
| 2005/0208083 | A1 | 9/2005 | Annis |
| 2006/0078525 | A1 | 4/2006 | Tomokuni |
| 2006/0140984 | A1 | 6/2006 | Tamarkin et al. |
| 2009/0110703 | A1 | 4/2009 | Tolla et al. |
| 2009/0324727 | A1 | 12/2009 | Foguet Roca |
| 2011/0060042 | A1 | 3/2011 | Ito |
| 2018/0168948 | A1* | 6/2018 | Glenn, Jr. ............... A61Q 5/02 |

FOREIGN PATENT DOCUMENTS

| | | |
|---|---|---|
| EP | 0620271 A1 | 10/1994 |
| EP | 0704209 A1 | 4/1996 |
| EP | 1473367 A1 | 11/2004 |
| EP | 1655021 A1 | 5/2006 |
| JP | 2002-302414 A | 10/2002 |
| JP | 2006-273821 A | 10/2006 |
| WO | WO 1996/041647 A1 | 12/1996 |
| WO | WO 1997/041855 A1 | 11/1997 |
| WO | WO 1998/021307 A1 | 5/1998 |
| WO | WO 2002/066589 A2 | 8/2002 |
| WO | WO 2005/027872 A2 | 3/2005 |
| WO | WO 2005/110370 A1 | 11/2005 |

OTHER PUBLICATIONS

Aboofazeli et al., "Particle Size Analysis of Concentrated Phospholipid Microemulsions: I. Total Intensity Light Scattering", AAPS PharmSci, 2000, 2(2): 1-13.
Alam et al., "Design and Characterization of Nanostructured Topical Gel of Betamethasone Dipropionate for Psoriasis," Journal of Applied Pharmaceutical Science, 2012, 2(10): 148-158.
Bagwe et al., "Improved Drug Delivery Using Microemulsions: Rationale, Recent Progress, and New Horizons", Critical Reviews in Therapeutic Drug Carrier Systems, 2001, 18(1): 77-140.
Binks et al., "Phase Behaviour of microemulsions stabilised by double chain cationic surfactants and alcohol co-surfactants", Colloids and Surfaces A: Physicochem. Eng. Aspects, Jan. 23, 2003, 212(2-3): 135-145.
Danielsson et al., "The Definition of Microemulsion", Colloids and Surfaces, Dec. 1981, 3(4): 391-392.
Fendler et al., "Liposomes as Drug Carriers", Life Sciences, Apr. 1, 1977, 20(7):1109-1120.
Fritsch et al., "Fluorescence Diagnosis and Photodynamic Therapy of Skin Diseases", Atlas and Handbook, 2003, pp. 23-31.
International Food Information Service, "Dictionary of Food Science and Technology", 2nd ed. 2009, p. 250.
International Search Report and Written Opinion for PCT International Patent Application No. PCT/EP2007/011404, dated May 9, 2008.
Kang et al., "Preparation and Characterization of Nano-Liposomes Using Phosphatidylcholine", International Journal of Industrial and Engineering Chemistry, Nov. 2005, 11(6): 847-851.
Kosar et al., "Exogenously-applied 5-aminolevulinic acid modulates some key physiological characteristics and antioxidative defense system in spring wheat (*Triticum aestivum* L.) seedlings under water stress," Journal of Botany, 2015, 96: 71-77.
Moreno, "Lecithin-Based Oil-in-Water Microemulsions for Parenteral Use: Pseudoternary Phase Diagrams, Characterization and Toxicity Studies", Wiley-Liss Journal of Pharmaceutical Science, 2003, 92(7): 1428-1437.
O'Neil et al., "The Merck Index: An Encyclopedia of Chemicals, Drugs, and Biologicals," Merck & Co., Inc.; entries for "aminolevulinic acid," "Lecithins," and "Polysorbates," 2006, pp. 1-8 (as provided).
Sarker, "Engineering of Nanoemulsions for Drug Delivery", Current Drug Delivery, Oct. 2005, 2(4): 297-310.

(Continued)

*Primary Examiner* — Jennifer Chin
(74) *Attorney, Agent, or Firm* — Lathrop GPM LLP; James H. Velema

(57) ABSTRACT

The present invention relates to stabilizing an oil in water nanoemulsion in a pressurized container. The nanovesicles comprised in the nanoemulsion are particularly stable in regard to vesicle size and vesicle size homogeneity after long-term storage at different temperatures.

21 Claims, 12 Drawing Sheets

(56) References Cited

OTHER PUBLICATIONS

Figure 1:

Sinko et al., "Martin's Physical Pharmacy and Pharmaceutical Sciences", Physical Chemical and Biopharmaceutical Principles in the Pharmaceutical Sciences, 15th ed., 2009, Chapter 18, "Coarse Dispersions" pp. 499-530.
Sonneville-Aubrun et al., "Nanoemulsions: a new vehicle for skincare products", Advanced Colloid and Interface Science, May 20, 2004, 108-109: 145-149.
Suppasansatorn et al., "Microemulsions as topical delivery vehicles for the anti-melanoma prodrug, temozolomide hexyl ester (TMZA-HE)", Journal of Pharmacy and Pharmacology, Jun. 2007, vol. 59, pp. 787-794.
Tadros et al., "Formation and stability of nano-emulsions", Advances in Colloid and Interface Science, May 20, 2004, vol. 108-109, pp. 303-318.
Weiss et al., "Nanostructured Encapsulation Systems: Food Antimicrobials", Global Issues in Food Science and Technology, 2009, Chapter 24, pp. 425-479.
Yuan et al., "Investigation of microemulsion system for transdermal delivery of meloxicam", International Journal of Pharmaceutics, Sep. 14, 2006, 321(1-2): 117-123.
Acharaya et al., "Physicochemical Investigations of Microemulsification of Coconut Oil and Water Using Polyoxyethylene 2-Cetyl Ether (Brij 52) and Isopropanol or Ethanol", Journal of Colloid and Interface Science, 2002, 245: 163-170.
Changez et al., "Effect of the composition of lecithin/n-propanol/isopropyl myristate/water microemulsions on barrier properties of mice skin for transdermal permeation of tetracaine hydrochloride: In vitro", Colloids and Surfaces B: Biointerfaces, 2006, 50: 18-25.
De Spiegeleer et al., "The Importance of the Cosolvent Propylene Glycol on the Antimicrobial Preservative Efficacy of a Pharmaceutical Formulation by DOE-Ruggedness Testing", Informa Healthcare; Pharmaceutical Development and Technology, 2006, 11: 275-284.

\* cited by examiner

PRESSURIZED NANOEMULSION

RELATED APPLICATIONS

This application claims priority to International Patent Application No. PCT/EP2023/059292, filed Apr. 6, 2023, the entire disclosure of which is hereby incorporated herein by reference.

DESCRIPTION

The present invention relates to stabilizing an oil in water nanoemulsion for pharmaceutical and cosmetic use which is comprised in a pressurized container. The nanovesicles are particularly stable regarding vesicle size and vesicle size homogeneity after long-term storage at different temperatures.

BACKGROUND OF THE INVENTION

Liquid nanoemulsions can be stored in containers under pressure with the help of a propellant. These pressurized nanoemulsions can be released as foam or spray, depending on the form of the dispenser head.

Foam and spray formulations are easy to distribute uniformly over the skin or the treatment area and can reach areas, which are difficult to reach, such as, wrinkles, skin folds etc., which makes them well suited for topical treatment. They are considered a convenient vehicle for topical delivery of active agents.

Foam and spray formulations are generally easier to apply, are less dense, and spread more easily compared with other topical dosage forms. When assessed, particularly in terms of ointments, or even creams and lotions, foams require negligible mechanical shearing force in order to spread the formulation on the skin. This is a major advantage when applying a medicament to highly inflamed skin; for example, in cases of sunburn where rubbing the formulation on to the skin to effect spreading may be painful or cause further inflammation. Furthermore, even when applied to hirsute areas such as the scalp, these formulations break down relatively rapidly, and easily reach the stratum corneum through the hair shafts. In this respect, they behave much like lotions and scalp application solutions, therefore resulting in enhanced patient compliance.

Foams are colloidal systems in which gas bubbles are suspended or dispersed in a liquid medium. Liquid foams usually need some sort of stabilizing or foaming agent to prevent or retard the coalescence of the gas bubbles. Foams are very complex and sensitive systems, especially foams for cosmetic or pharmaceutical use.

There are several types of topical foams, including aqueous foams, such as commonly available shaving foams; hydroalcoholic foams; emulsion-based foams, comprising oil and water components; and oleaginous foams, which consist of high oil content. In skin therapy, oil containing foams are preferred, since oil contributes to skin protection and moisturization, which may improve the therapeutic effect of the formulation. Typically, foams are made using liquefied hydrocarbon gas propellants, such as propane, butane and isobutane, or hydro-fluoro carbon propellants.

Nanoemulsions are homogeneous, transparent, and slightly opalescent dispersions of oil and water. These dispersions are colloidal systems. The dispersed particles or vesicles in such emulsions are composed of a lipid core surrounded by at least one surfactant or emulsifier monolayer. Nanoemulsions are characterized by a mean particle or vesicle size of less than 200 nm, often less than 100 nm and a predominantly monodisperse particle or vesicle size distribution with a polydispersity index below 0.4.

Although nanoemulsions are generally thermodynamically more stable than conventional emulsions and microemulsions, they are often not stable in stress situations such as high temperature or freezing conditions. They can be in a metastable state and its structure depends often on the manufacturing process, making them a fragile system and complicated to formulate to a pharmaceutical or cosmetic composition, which have to maintain stability for long periods of time. If destabilized, they can become opaque, exhibit creaming or phase separation. On the other side, nanoemulsions can provide useful applications in skin care in that they may exhibit good textural and sensual properties due to the fine and homogenous nanovesicle, droplet or globule size making them a favorable vehicle for pharmaceutical and cosmetical compositions.

In pharmaceutical and cosmetic formulations, nanoemulsions are combined with active agents, such as 5-aminolevulinic acid.

5-aminolevulinic acid (also termed herein "ALA" or "5-ALA") is a small biogenic amino acid with a molecular weight (as HCl salt) of 167.59 g/mol and is very hydrophilic, i.e. readily soluble in water with an octanol-water partition coefficient (log P) of around-3. ALA is used in Photodynamic Therapy (PDT) as a prodrug to drive the synthesis of protoporphyrin IX in diseased tissue, which is subsequently illuminated with light of appropriate wavelengths to induce the photodynamic effect.

Known formulations of ALA for topical use on the skin are instable in aqueous solutions (see Reinhold, Future Oncology, 2017 November; 13 (27): 2413-2428, doi: 10.2217/fon-2017-0247). So far, the nanoemulsion used with ALA contained 10% active ingredient and was formulated as a gel. The previous gel formulation showed stability up to 36 months at refrigerated temperatures (2-8° C.) but was susceptible to higher temperatures (standard room temperature and above). Exposure to higher temperatures was tolerated in the range of only a week without risking pharmaceutical quality loss for human use.

The prior art fails to teach a nanoemulsion composition, which is highly stable, even under stressed conditions (e.g., elevated temperature or at freezing conditions), on itself or combined with active pharmaceutical or cosmetic ingredients. The stability of such nanoemulsion compositions is characterized by a small droplet (nanovesicle) size and a predominantly monodisperse population of nanovesicles. Surprisingly, the inventors found that these two properties are stable over a long period of time and under stressed conditions when the nanoemulsion is stored in a pressurized container. The concentration of active agent in cosmetic and pharmaceutical compositions with nanoemulsions is also positively influenced by a pressurized formulation. The same formulations are much less stable, specially under stressed conditions, when not stored in a pressurized container. It is also surprising that the stability of the pressurized nanoemulsion is not dependent on the presence and/or concentration of gelling agents, known as emulsion stabilizers.

As described above, nanoemulsions tend to coalescent under certain circumstances, such as exposure to extreme temperatures, leading to bigger droplet sizes and harm the nanoemulsion quality.

These aspects make it clear that design and formulation of a pressurized nanoemulsion composition with high stability in regard to droplet sizes and vesicle size distributions under different storage temperatures compared to a nanoemulsion, which has not been stored in a pressurized container, could in no way be considered trivial or simple, but required considerable inventive activity.

SUMMARY OF THE INVENTION

A first aspect of the invention relates to a formulation comprising: (a) a nanoemulsion comprising: (i) at least one aqueous component; (ii) a carrier component comprising (1) at least one lipophilic component, (2) at least one surfactant, and (3) at least one alcohol; and (b) a propellant, wherein the formulation is comprised in a pressurized container, and wherein the formulation comprises essentially no fatty alcohol as foam adjuvant.

A second aspect of the invention relates to a method for stabilizing a nanoemulsion, comprising the following steps: (a) providing a nanoemulsion comprising: (i) at least one aqueous component; (ii) a carrier component comprising: (1) at least one lipophilic component, (2) at least one surfactant, and (3) at least one alcohol; (b) introducing the nanoemulsion into a container; and (c) adding a propellant to the container to pressurize the container.

A third aspect of the invention relates to a use of a nanoemulsion for the preparation of a foam or a spray, comprising the following steps: (a) providing a formulation comprising a nanoemulsion, the nanoemulsion comprising: (i) at least one aqueous component; (ii) a carrier component comprising: (1) at least one lipophilic component, (2) at least one surfactant, and (3) at least one alcohol; (b) introducing the formulation comprising the nanoemulsion into a container; (c) adding a propellant to the container to pressurize the container; and (d) releasing a foam or a spray from the pressurized container.

A fourth aspect of the invention relates to a container or a dispenser product comprising a container, comprising a formulation, wherein said formulation comprises a nanoemulsion comprising (i) at least one aqueous component; (ii) a carrier component comprising (1) at least one lipophilic component, (2) at least one surfactant, and (3) at least one alcohol; and (b) a propellant, wherein the formulation comprises essentially no fatty alcohol; and wherein the container further comprises a propellant, wherein the propellant is provided to pressurize the container.

A fifth aspect of the invention relates to a foam obtained from the formulation of the first aspect.

A sixth aspect of the invention relates to a cosmetic use of the formulation of the first aspect or the foam of the fifth aspect.

A seventh aspect of the invention relates to the formulation of the first aspect or the foam of the fifth aspect for use in medicine.

DETAILED DESCRIPTION

Before the present invention is described in detail below, it is to be understood that this invention is not limited to the particular methodology, protocols and reagents described herein as these may vary. It is also to be understood that the terminology used herein is for the purpose of describing particular embodiments only and is not intended to limit the scope of the present invention, which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IU-PAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturers' specifications, instructions etc.), whether supra or infra, is hereby incorporated by reference in its entirety.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims that follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

Generally, in pharmaceutical technology, topical formulations are chosen to accommodate the physico-chemical properties of the API and to enhance or regulate both skin/body surface penetration and stability. Usually, APIs with clearly different properties, such as molecular weight or degree of lipophilicity, demand markedly different formulations as suitable vehicles.

In preferred embodiments, the formulations of the present invention bring the advantages of foams and nanoemulsions together.

The formulations of the invention comprise three phases:
(I) an aqueous phase or aqueous component,
(II) a lipid phase or carrier component, and
(III) a gas phase (i.e. a propellant).

The aqueous phase and the lipid phase together form the nanoemulsion. The nanoemulsion is present in liquid form. Thus, the formulations of the invention can also be described as comprising
 a liquid element comprising or consisting of the nanoemulsion, and
 a gas element.

In the context of the present invention, the term "liquid" specifies a low-viscosity formulation of one or more fluids in which other components are dissolved or dispersed. Low viscosity in the context of the present specification refers to a viscosity of ≤8 Pa s (pascal-second), ≤6 Pa s, ≤5 Pa s, preferably ≤4 Pa s, ≤3 Pa s, more preferably ≤1.0 Pa s, or ≤0.5 Pa s.

The skilled person is aware of suitable methods for determining the viscosity. Preferably, the viscosity is determined as described in the examples section.

The examples of the present invention demonstrate that the stability of a formulation comprising nanovesicles can be improved when stored in a pressurized storage device. In particular, the stability is improved when stored under stressed conditions, such as storage at elevated temperatures (e.g., 40° C.), or when subjected to a freeze-thaw cycle.

The presence of a gelling agent, such as xanthan gum or poloxamer, can further improve the stability, in particular at elevated temperature (e.g., 40° C.), and/or when subjected to a freeze-thaw cycle. The data of the invention demonstrate that surprisingly, nanovesicle size stability is dependent on the interplay between lipid content and gelling agent in formulations stored under pressure. This is not the case in formulations stored in conventional storage devices, such as tubes or glass vials and which do not form a foam. In the formulation of the invention, the addition of poloxamer provides better nanovesicle size stability at stressed conditions (e.g., at 40° C.) with high lipid contents (e.g., 20%), while at lower lipid content (e.g., 10%), the absence of any gelling agent provides better stability at stressed conditions (e.g., at 40° C.). The gelling agent poloxamer can have opposite effects on nanovesicle stability depending on the lipid content of the nanoemulsion. With high lipid content (such as 20%), poloxamer improves stability, while with lower lipid content (such as 10%) this effect was not observed. The discovery of this specific interplay is unprecedented by prior knowledge.

The data of the invention demonstrates that high lipid content (e.g., of 15-20% w/w with respect to the nanovesicles) can improve foam strength (characterized by the collapse time) of a foam generated from the formulation comprising nanovesicles, as described herein.

In the formulation of the invention, the presence of xanthan gum provides better nanovesicle size stability at stressed conditions (e.g., 40° C.) in pressurized containers.

Furthermore, the present invention demonstrates that the stability of a formulation comprising nanovesicles can be improved, wherein an active agent is dissolved in the aqueous phase or dissolved into the nanovesicles, when stored in a pressurized device, compared to a conventional storage device, such as a glass vial, stability meaning both or either nanovesicle size and/or chemical stability of the active ingredients. The inventors have found that the stabilizing effect can be observed in nanoemulsions (and foams derived thereof) carrying active agents with very different properties. Two examples that are useful to understand the range of properties in terms of molecular weight and hydrophilicity: the hydrophilic compound 5-aminolevulinic acid hydrochloride weight of 131 g/mol, and the lipophilic compound tacrolimus, having a molecular weight of 804 g/mol. These exemplary compounds, not limiting the scope of the invention, cover hydrophilic and lipophilic compounds with a molecular weight in the range of about 100 g/mol to about 1000 g/mol.

An exemplary formulation of the invention comprises ALA. A formulation comprising ALA can be prepared with a lipid phase (or carrier component) of, for example, 10%.

Another example of the invention relates to a formulation comprising TC. The release of TC from a formulation and subsequent penetration of the skin, can be improved using a nanoemulsion formulation, in particular a nanoemulsion foam, with a lipid phase (or carrier component) of, for example, 20%. Foams may further be beneficial in combination with TC, because they are easier and more pleasant to apply due to their soft texture. This is of added value when sensitive or irritated skin is treated, such as with atopic dermatitis or similar conditions. Further, the nanoemulsion foam formulation in pressurized containers is able to stabilize TC under stressed conditions.

Another example of the invention is a nanoemulsion formulation comprising the API betamethasone propionate (BMP), a high potency topical corticosteroid. BMP can be used to treat inflammatory conditions of the skin. BMP has a molecular weight of 392.46 g/mol and a log P of 1.14. A BMP nanoemulsion according to the invention can comprise 15% of carrier component. It thus has properties in between ALA and TC, further highlighting the versatility of the nanoemulsion formulation of the invention.

In a first aspect of the invention relates to a formulation comprising:
   (a) a nanoemulsion comprising:
      (i) at least one aqueous component;
      (ii) a carrier component comprising:
         (1) at least one lipophilic component,
         (2) at least one surfactant, and
         (3) at least one alcohol, and
   (b) a propellant,
   wherein the formulation is comprised in a pressurized container and
   wherein the formulation comprises essentially no fatty alcohol.

The formulation comprised in the pressurized container can also be referred to as "pressurized formulation", and the nanoemulsion comprised in the formulation can be referred to as "pressurized nanoemulsion".

In some embodiments, the formulation is a lotion, a spray, a foam, an emulsion, a nanoemulsion, a gel or a cream. In some embodiments, the formulation comprised in the pressurized container is a lotion, an emulsion, a nanoemulsion, a gel or a cream. In some embodiments, the formulation comprised in the pressurized container is a lotion. In the context of the present specification, a lotion is a low-viscosity topical preparation intended for application to the skin. In preferred embodiments the formulation is a liquid as specified above. The pressurized formulation can be released from the pressurized container as a spray or foam.

In preferred embodiments of any aspect described herein, the formulation comprising the nanoemulsion is a foamable formulation. In the context of the present specification, the term "foamable" signifies that when a formulation is released from the pressurized container via a suitable valve, a foam is obtained. The skilled person is aware of suitable valves for the formation of a foam from a liquid formulation comprised in a pressurized container. Relevant information relating to the generation of a foam from a liquid formulation comprised in a pressurized container can be found e.g. in "Pharmazeutische Technologie" 9th edition, Rudolf Voigt (Deutscher Apotheker Verlag Stuttgart 2000).

In preferred embodiments of the formulations described in the present invention, the aqueous component comprises an aqueous phase or forms an aqueous phase.

In preferred embodiments of the formulations described in the present invention, the carrier component comprises or consists of nanovesicles. In other words, the nanoemulsion comprises nanovesicles. In some embodiments, the nanovesicles comprise the at least one lipophilic component, the at least one surfactant, and the at least one alcohol.

In preferred embodiments, the formulation is provided for topical use.

In pressurized formulations, in particular in foamable formulations, fatty alcohols have been described to work as foam adjuvants.

In the context of the present specification, the term "foam adjuvant" relates to compounds capable of increasing the foaming capacity of a formulation and/or stabilizing a foam.

In particular, the term "foam adjuvant" relates to fatty acids and fatty alcohols having at least 6 carbon atoms.

The formulation of the first aspect of the invention comprises essentially no fatty alcohol. Preferably, the formulation comprises essentially no fatty alcohol and essentially no fatty acid. More preferably, the formulation comprises essentially no foam adjuvant.

In the context of the present specification, the expression "essentially no" specifies that the formulation is either free of a compound or comprises less than 0.5% (w/w), less than 0.4% (w/w), less than 0.3% (w/w), less than 0.2% (w/w), less than 0.1% (w/w), less than 0.08% (w/w), less than 0.07% (w/w), less than 0.06% (w/w), less than 0.05% (w/w), less than 0.04% (w/w), less than 0.03% (w/w), less than 0.02% (w/w), or less than 0.01% (w/w) of a compound based on the total weight of the formulation.

Whenever it is specified that the formulation comprises "essentially no compound X", it is preferred that the formulation comprises "no compound X".

In the context of the present specification, the term "fatty alcohol" relates to alcohols having at least 6 carbon atoms, usually 6-28 carbon atoms. Fatty alcohols can be saturated or unsaturated and unbranched or branched. Fatty alcohols are usually straight-chain primary alcohols. The term "fatty alcohol" as used herein relates to fatty alcohols in their standalone form and does not include esters comprising fatty alcohols.

In the context of the present specification, the term "fatty acids" relates to carboxylic acids with an aliphatic chain of at least 6 carbon atoms, usually 6-28 carbon atoms. Fatty acids can be saturated or unsaturated and unbranched or branched. Most naturally occurring fatty acids have an unbranched chain of carbon atoms. The term "fatty acid" as used herein relates to fatty acids in their standalone form and does not include esters comprising fatty acids.

The formulation is either free of a fatty alcohol (in its standalone form, or in other words as isolated molecule) or comprises less than 0.5% (w/w), less than 0.4% (w/w), less than 0.3% (w/w), less than 0.2% (w/w), less than 0.1% (w/w), less than 0.08% (w/w), less than 0.07% (w/w), less than 0.06% (w/w), less than 0.05% (w/w), less than 0.04% (w/w), less than 0.03% (w/w), less than 0.02% (w/w), or less than 0.01% (w/w) of a fatty alcohol (in its standalone form, or in other words as isolated molecule) based on the total weight of the formulation.

In particular, the formulation is either free of a fatty acid and a fatty alcohol (in their standalone form, or in other words as isolated molecules) or comprises less than 0.5% (w/w), less than 0.4% (w/w), less than 0.3% (w/w), less than 0.2% (w/w), less than 0.1% (w/w), less than 0.08% (w/w), less than 0.07% (w/w), less than 0.06% (w/w), less than 0.05% (w/w), less than 0.04% (w/w), less than 0.03% (w/w), less than 0.02% (w/w), or less than 0.01% (w/w) of a fatty acid and a fatty alcohol (in their standalone form, or in other words as isolated molecules) based on the total weight of the formulation.

Preferably, the formulation is either free of foam adjuvant or comprises less than 0.5% (w/w), less than 0.4% (w/w), less than 0.3% (w/w), less than 0.2% (w/w), less than 0.1% (w/w), less than 0.08% (w/w), less than 0.07% (w/w), less than 0.06% (w/w), less than 0.05% (w/w), less than 0.04% (w/w), less than 0.03% (w/w), less than 0.02% (w/w), or less than 0.01% (w/w) of a foam adjuvant based on the total weight of the formulation.

Surprisingly, the formulation of the present invention comprised in a pressurized container has a high foaming capacity and forms a stable foam (long collapse time) when released from the pressurized container, even in the absence of a fatty alcohol or another foam adjuvant.

In preferred embodiments, the formulation of the first aspect of the invention comprises essentially no emollient selected from a monoester or diester comprising an alcohol and a carboxylic acid.

In the context of the present specification, the term "monoester" relates to a molecule containing one and only one ester group, and the term "diester" relates to a molecule containing two and only two ester groups.

In the context of the present specification, the term "emollient" relates to compounds that have a softening or hydrating effect when applied to skin. Emollients are capable of covering skin with a protective film to prevent loss of moisture.

Examples of emollients are isostearic acid esters, isopropyl palmitate, isopropyl isostearate, diisopropyl adipate, diisopropyl dimerate, octyl palmitate, cetyl lactate, cetylricinoleate, tocopheryl acetate, cetyl acetate, phenyl trimethicone, glyceryl oleate, tocopheryllinoleate, arachidyl propionate, myristyl lactate, decyl oleate, propylene glycol ricinoleate, isopropyl lanolate, pentaerythrityl tetrastearate, neopentyl glycol dicaprylate/dicaprate, isononyl isononanoate, isotridecyl isononanoate, myristyl myristate, triisocetyl citrate, octyl dodecanol, octyl hydroxy stearate and sucrose esters of fatty acids.

In particular, the formulation of the first aspect of the invention comprises essentially no diisopropyl adipate, essentially no isopropyl myristate and essentially no glyceryl monostearate.

In preferred embodiments, the formulation of the first aspect of the invention comprises essentially no gelling agent or only low amounts of a gelling agent. If the formulation of the first aspect of the invention comprises a gelling agent, the gelling agent is comprised in an amount that does not effect the formation of a gel. As described above, the formulation of the first aspect of the invention comprises a liquid element (the element comprising the nanoemulsion) and a gas element (the propellant). In instances where the formulation comprises a gelling agent, the gelling agent is comprised at a concentration of 5% or less, 4% or less, 3% or less, 2% or less, 1% or less or 0.5% or less based on the total weight of the formulation. In instances where the formulation comprises Poloxamer as a gelling agent, Poloxamer is comprised at a concentration of 5% or less, 4% or less, 3% or less, 2% or less, 1% or less or 0.5% or less based on the total weight of the formulation. In instances where the formulation comprises Xanthan as a gelling agent, Xanthan is comprised at a concentration of 2% or less, 1% or less or 0.5% or less based on the total weight of the formulation.

In preferred embodiments, the formulation of the first aspect of the invention comprises essentially no gelling agent.

In the context of the present specification, the term "gelling agent" relates to a polymeric agent capable of increasing the viscosity of a formulation. Gelling agents include poloxamer, xanthan, bentonite, sodium carboxymethylcellulose, hydroxymethyl cellulose, carbomer, hydroxypropyl cellulose, gellan gum, guar gum, pectin, poly(ethylene)oxide, polycarbophil, alginate, tragacanth, povidone, and gelatin. Gelling agents were described to increase the stability of a nanoemulsion formulation.

Surprisingly, the formulation of the present invention comprised in a pressurized container is highly stable with regard to nanovesicle size, even in the absence of a gelling agent or in the presence of only low concentrations of a gelling agent.

In some embodiments, the formulation comprises an active agent. The terms "active agent" and "active ingredient" are used interchangeably herein. The active agent may be dissolved in the aquaeous phase and capable to interact with the surface of the nanovesicles, and/or the active agent may be dissolved in the core of the nanovesicles. Surprisingly, the formulation of the present invention comprised in a pressurized container is highly stable with regard to the concentration of the active agent, even in the absence of a gelling agent or in the presence of only low concentrations of a gelling agent.

As used herein "capable to interact with the surface of the nanovesicles" includes non-covalently binding of the active agent to the nanovesicles, in particular to the surface of the nanovesicles. For example, at least 10%, at least 20%, at least 30%, at least 40%, at least 50%, at least 70%, at least 80%, or at least 90%, of the total amount of active agent interacts with the surface of the nanovesicles, the balance being dissolved in the aqueous phase.

The small size of the nanovesicles and their high homogeneity confers on them cosmetically advantageous properties, which distinguish them from conventional emulsions: The nanoemulsions of the present invention are transparent and exhibit a novel texture. Further, the nanoemulsion of the present invention can carry active agents more efficiently and, thus, become increasingly important in the field of medicine and pharmacy.

The formulation of the present invention, provided in a pressurized container is surprisingly resistant to aging at stressed conditions in respect to API content and nanoemulsion vesicle size, compared to a nanoemulsion which has been stored in a non-pressurized container, e.g., in a tube or glass vial. In the formulation of the invention, the active ingredient content is stable over a long period of time. In some embodiments, stability can be further improved if the formulation comprises an adjuvant or gelling agent chosen from polymeric agents, such as xanthan gum or poloxamer, such as Poloxamer 407.

"Aging" as used herein, refers to alteration, disintegration and/or degradation of the formulation and/or the active agent, affecting chemical and physical stability during storage, in particular under stressed conditions. Such physical or chemical changes due to storage may include, but are not limited to, Ostwald ripening, flocculation or coalescence, which may lead to a change in nanovesicle size or polydispersity index.

"Aging" as used herein, also refers to alteration, disintegration and/or degradation of the active agent, affecting chemical and physical stability during storage, in particular under stressed conditions. Such physical or chemical changes due to storage may include, but are not limited to a decrease in the concentration of the active agent or the increase of impurities.

As used herein, "stressed conditions" for storage are temperatures significantly exceeding room temperature (e.g., 40° C.), or being significantly below commonly used storage temperatures (e.g., below 0° C., such as −15 to −25° C.).

The Examples of the present invention demonstrate that the pressurized nanoemulsion of the present invention leads to unexpected stable nanovesicle sizes under different conditions, including stressed conditions.

As used herein, a "nanovesicle emulsion" or a "nanoemulsion" is a dispersion of oil in water (oil-in-water dispersion, oil-in-water emulsion, O/W emulsion). The nanoemulsion can be monophasic, transparent, and slightly opalescent. The nanoemulsions of the present invention can be colloidal systems. The dispersed vesicles in such emulsions can be composed of a lipid core surrounded by at least one surfactant or emulsifier monolayers. The nanoemulsions of the present invention can be characterized by a mean vesicle size of less than 500 nm less, than 200 nm, or less than 100 nm. The nanoemulsions of the present invention can have a predominantly monodisperse vesicle size distribution, for example a vesicle size distribution characterized by a polydispersity index of less than or equal to 0.4 or 0.3.

As used herein, "nanovesicle", "nano vesicle", "lipid vesicles", "oil droplets", "droplets" and "oil globules" are interchangeable and refer to small oil droplets in an oil in water emulsion. A lipid vesicle of an average size (see above, e.g., below 500, 200, 100 nm) comprises a monolayer of a surfactant and a lipid core. In the present invention, the nanovesicles can have a size of less than or equal to 500 nm, or less than or equal to 300 nm, or less than or equal to 200 nm, preferably in the range of 5 nm to 200 nm, more preferably in the range of 5 nm to 100 nm.

As used herein, the term "nanoparticle" or "nano particle", is distinguished form "nanovesicles", and refers to solid particles, which are not described in this invention. The formulation of the present invention may be a formulation which is essentially free of nanoparticles. "Essentially free of nanoparticles" means, that the formulation comprises less than or equal to 2% by weight, or less than or equal to 1% by weight, or does not comprise nanoparticles. Nanoparticles are mainly inorganic or polymeric solid particles may have a size of below 100 nm, below 200 nm, or below 500. The size can be determined by the methods as described herein. For example, the formulation may be essentially free of nanoparticles with a diameter of less than 100 nm, as determined by dynamic light scattering.

As used herein, "topical use" of the formulation of the invention describes an application to a particular place on or in the body, in particular the human body. This includes, but is not limited to administration of the formulation to body surfaces such as the skin or mucous membranes. The topical use can be epicutaneous, meaning that the formulation is directly administered to the skin. The topical use can be pharmaceutical or cosmetic use.

As used herein, the "stability" of a formulation comprising nanovesicles, as described herein, includes, but is not limited to the physical and chemical stability. In particular, in the present invention, a formulation is stable if the integrity of the nanovesicles is found to be stable. A measure known to the skilled person to describe integrity of the nanovesicles is the average size and the polydispersity index, as for example determined by dynamic light scattering, as described herein. The nanovesicles produced according to the invention can have a size below 200 nm, preferably below 100 nm, more preferably below 50 nm, even more preferably below 30 nm, immediately after manufacture. The Examples of the invention demonstrate that the size of the nanovesicles may increase to more than 1000 nm or 1500 nm in non-stabilized comparative formulations when stored at stressed condition. In contrast, the size of nanovesicles remains small in the formulations of the invention comprised in a pressurized container. For example, the formulation as described herein is stable if the nanovesicles in the formulation of the present invention have a size (or diameter) of less than or equal to 500 nm or less than or equal to 300 nm, or less than or equal to 200 nm, preferably in the range of 5 nm to 200 nm, more preferably in the range of 5 nm to 100 nm when stored, for example, at stressed conditions, as described herein.

"Stability" can also refer to the absence of processes above described as aging, leading to a loss of pharmaceutical functionality or quality. The pharmaceutical composition described in this invention is pharmaceutically functional, as long as the nanovesicle size is less than or equal to 500 nm or less than or equal to 300 nm, or less than or equal to 200 nm, preferably in the range of 5 nm to 200 nm, more preferably in the range of 5 nm to 100 nm.

Furthermore, "stability" can refer to the stable content of the active pharmaceutical agent or cosmetic agent. During storage, the content of the pharmaceutical active agent or cosmetic active agent is, for example, considered stable if at least 70%, at least 80% or at least 90% of the content of the active agent is still present, when stored, for example, at stressed conditions, as described herein.

In the context of the present specification, whenever a duration is described as "one month, two months, three months" etc., this is meant to include embodiments in which the duration is "at least one month, at least two months, at least three months" etc.

In a formulation of the invention comprising ALA, the ALA content may be
(i) at least 90% or at least 95% after storage for 1, 2, 3, 4, 5, 6, 7, 8, 9, 10, 11 or 12 months at 40° C., and/or
(ii) at least 95% or at least 97% after storage for 1, 2, 3, 4, 5, 6, 12, 18, 24, 30 or 36 months at 25° C., and/or
(iii) at least 95%, at least 97% or at least 99% after storage for 1, 2, 3, 4, 5, 6, 12, 18, 24, 30 or 36 months at 5° C.

In a formulation of the invention comprising TC, the TC content may be
(i) at least 90% after storage for 1 month at 40° C., and/or
(ii) at least 78%, or at least 80% after storage for 1 or 2 months at 40° C., and/or
(iii) at least 71%, or at least 75% after storage for 1, 2 or 3 months at 40° C., and/or
(iv) at least 90%, at least 95%, or at least 97%, or at least 99% after storage for 1, 2, 3, 4, 5, 6, 7, 8, 9, 10, 11 or 12 months at 25° C., and/or
(v) at least 83%, or at least 88% after storage for 1, 2, 3, 4, 5, 6, 7, 8, 9, 10, 11 or 12 months at 25° C., and/or
(vi) at least 90%, at least 95%, at least 97%, or at least 99% or 100% after storage for 1, 2, 3, 4, 5, 6, 7, 8, 9, 10, 11, 12, 18 or 24 months at 5° C.
(vii) at least 90%, at least 95%, or at least 97%, or at least 99% or 100% after storage for 1, 2, 3, 4, 5, 6, 12, 18, 24, 30 or 36 months at 5° C.
(viii) at least 90%, at least 95%, at least 97% or at least 99% or 100% after storage for 1, 2, 3, 4, 5, 6, 12, 18, 24, 30, 36, 42 or 48 months at 5° C.

In the present invention, the formulation can be stable for at least 2 months, at least 3 months, at least 6 months, at least 9 months, e.g. at elevated temperature (e.g. 40° C.). In particular, the formulation of the invention can be stable for at least 3 months, at least 6 months, at least 9 months, at least 12 months, at least 24 months, or at least 36 months at 2-25° C., e.g. at 15-25° C. or at about 5° C. In particular, the formulation of the invention can be stable when subjected to 1, 2, 3, 4, 5 or even more freeze-thaw cycles.

The nanovesicles comprised in the formulation of the present invention have a stable size. The size of the nanovesicles is as indicated below upon preparation. Importantly, the size stays within the indicated ranges even after storage at stressed conditions, in particular storage at elevated temperatures or freezing and thawing.

The formulation of the present invention is homogeneous (predominantly monodisperse) as characterized by a polydispersity index of less than or equal to 0.4. The formulation of the present invention has a stable polydispersity index. The polydispersity index is less than or equal to 0.4 upon preparation. Importantly, the polydispersity index is also less than or equal to 0.4 even after storage at stressed conditions, in particular storage at elevated temperatures or freezing and thawing. In preferred embodiments of any aspect of the invention, the polydispersity index is less than or equal to 0.3.

The nanovesicles in the formulation of the present invention may have a size of less than or equal to 500 nm, or less than or equal to 300 nm, preferably in the range of 5 nm to 200 nm, more preferably in the range of 5 nm to 100 nm, in particular when stored for three, four, five or six months at 40° C. in a pressurized container.

The nanovesicles in the formulation of the present invention may have a size (or diameter) of less than or equal to 500 nm or less than or equal to 300 nm, preferably in the range of 5 nm to 200 nm, more preferably in the range of 5 nm to 150 nm, in particular when subjected to at least one freeze-thaw cycle, preferably one, two, three, four or five freeze-thaw cycles. In particular, a formulation comprising xanthan, as described herein, may comprise nanovesicles having this size.

The at least one freeze-thaw cycle may comprise storage of the formulation independently below −15° C., preferably at −24° C., and thawing, for example at room temperature (e.g., independently selected from 15-25° C.). The formulation may be stored for a period allowing to cool down, for example at least 10 min, at the maximum 30 min, at the maximum 1 h, at the maximum 2 h, at the maximum 6 h or at the maximum 12 h. The formulation may be stored, for example for at the maximum 1 day, at the maximum 2 days, at the maximum 3 days, at the maximum 4 days, at the maximum 5 days, at the maximum 6 days, or even longer.

The nanovesicles in the formulation of the present invention may have a size (or diameter) of less than or equal to 500 nm or less than or equal to 300 nm, preferably in the range of 5 nm to 200 nm, more preferably in the range of 5 nm to 150 nm, in particular when stored below −15° C., preferably at −24° C., in a pressurized container. The formulation may be stored for a period allowing to cool down, for example at least 10 min, at the maximum 30 min, at the maximum 1 h, at the maximum 2 h, at the maximum 6 h or at the maximum 12 h. The formulation may be stored, for example for at the maximum 1 day, at the maximum 2 days, at the maximum 3 days, or at the maximum 4 days, or even longer. In particular, a formulation comprising xanthan, as described herein, may comprise nanovesicles having this size.

The vesicle size or diameter of the nanovesicles as described herein can be expressed as the Z-average (also termed "z-average"). The size distribution of the nanovesicles can be characterized by the polydispersity index. These parameters are well known to the skilled person, and are widely used in the art to characterize particle or vesicles in emulsions, suspensions and/or polymeric solutions.

In the present invention, the z-average (e.g., in nm) and/or the polydispersity index of nanovesicle formulations can be determined by dynamic light scattering (also referred as Photon Correlation Spectroscopy (PCS) or Quasi-Elastic Light Scattering (QELS)). Dynamic light scattering is well known in the art and well established to determine size of nano or micro particles or vesicles in emulsions, suspensions and/or polymeric solutions with a laser.

In the formulation as described herein, the total aqueous component can be present in an amount of 50% to 99% w/w, based on the total weight of the nanoemulsion (a), preferably from 70% to 95% (w/w), and more preferably from 75% to 95% (w/w).

The aqueous component can comprise at least one pH buffering agent. Any suitable buffering agent may be used. Suitable buffering agents are known to the skilled person. For example, the at least one pH buffering agent can be selected from the group consisting of citrate, phosphate, acetate and carbonate.

The pH of the aqueous component can be in the range of 2-9. The pH of the aqueous component can also be preferably in the range of 2-7 or 2-6, such as 2, 3, 4, 5 or 6, more preferably in the range of 3-6 or 4-6, such as 3, 4, 5 or 6. The pH of the aqueous component can also be in the range of 7-9.

In the formulation as described herein, the at least one lipophilic component can be selected from triglycerides and mixtures thereof.

Preferably, the at least one lipophilic component is a lipid, a vegetable oil, a synthetic oil and/or an animal oil. Suitable lipids according to the present invention are physiologically acceptable lipids such as ceramide, mono-, di- and triacylglycerin (triglycerides). In particular, the at least one lipophilic component is a triglyceride, in particular a triglyceride comprising a $C_8$-10 fatty acid, or a mixture thereof. More particular, the at least one lipophilic component is a caprylic and/or capric triglyceride and/or a mixture thereof, particularly preferably Miglyol (such as Miglyol 812, available from IOI Oleochemical) or Myritol (such as Myritol 318, available from BASF). Suitable vegetable and animal oils e.g., are sunflower oil, soybean oil, peanut oil, rape oil, fish oil and/or cetaceum.

In the formulation as described herein, the at least one lipophilic component can be present in an amount of from 0.1% to 30% (w/w) based on the total weight of the nanoemulsion (a), preferably from 0.25% to 15% (w/w), preferably from 0.25% to 10% (w/w), and more preferably from 0.5% to 8% (w/w) or 3% to 8% (w/w). Also preferred is the at least one lipophilic component being present in an amount of from 10% to 30% (w/w) based on the total weight of the nanoemulsion (a), more preferably 15-30%, or 20-30%.

In the formulation as described herein, a triglyceride or triglycerides can be present in an amount of from 2% to 10% (w/w), based on the total weight of the nanoemulsion (a), preferably from 3% to 8% (w/w).

In the formulation as described herein, the at least one surfactant may be any suitable surfactant known to the skilled person.

Surfactants, also referred as surface active agents or emulsifiers, are well-known in the art and include any agent linking oil and water in the composition to form an emulsion. They lower the surface tension of two liquids and are amphiphilic. In emulsions they are referred as emulsifiers and coat the droplets preventing coalescing. Emulsifiers can be described with the hydrophilic/lipophilic balance (HLB), which expresses their affinity towards water or oil. Low HLB (e.g., HLB=1) refers to lipophilic emulsifiers and high (e.g., HLB=20) to hydrophilic emulsifiers. In general, lipophilic emulsifiers are used for water-in-oil emulsions and hydrophilic emulsifiers for oil-in-water emulsions. Persons skilled in the art will identify which emulsifiers or mixtures of them are suited for the preferred vehicles and purpose of the composition. In certain emulsions, combinations of emulsifiers might be advantageous.

A suitable membrane-forming surfactant is a phospholipid, a lysophospholipid, a ceramide and/or a mixture thereof. Preferably, the phospholipid is lecithin or cephalin from soybeans or hens' eggs. More preferably the at least one surfactant is lecithin, most preferably soy lecithin.

In the formulation as described herein, the phospholipid, the lysophospholipid, the ceramide and/or the mixture thereof can be present in an amount of from 1% to 10% (w/w), based on the total weight of the nanoemulsion (a), preferably from 1.25% to 5% (w/w), and more preferably from 1.5% to 4% (w/w).

Preferably, the lecithin has a phosphatidylcholine content of at least 80% by weight, more preferably of at least 90% by weight, and most preferably of at least 94% by weight. The quality of the lecithin, namely its phosphatidylcholine content, plays a crucial role for the size of the vesicles of the nanoemulsion. The higher the phosphatidylcholine content of the lecithin, the smaller is the size of the vesicles of the nanoemulsion.

As O/W emulsion-forming surfactant, anionic, nonionic, cationic and/or amphoteric surfactants are suitable as well as block copolymers. Suitable anionic surfactants are soaps, alkylbenzene sulphonates, alkane sulphonates, alkylsulfates and/or alkyl ether sulfates. Suitable cationic surfactants are quaternary ammonium compounds, preferably having one or two hydrophobic groups (e.g., cetyltrimethylammonium bromide and cetyltrimethylammonium chloride) and/or salts of tong-chain primary amines. A suitable amphoteric surfactant is N-(acylamidoalkyl)betaine, phosphate-alkyl-ammonium compounds, N-alkyl-β-aminopropionate and/or amine-N-oxide. A suitable copolymer building block, for example, is propylene oxide. In the present invention, a nonionic surfactant is particularly preferred as O/W emulsion-forming surfactant.

In the formulation as described herein, the at least one surfactant can be any a polyoxyethylene-type surfactant. A suitable nonionic surfactant can be selected from the group consisting of fatty alcohol polyglycolether, alkylphenol polyglycolether, alkylpolyglucoside, fatty acid glucamide, fatty acid polyglycolether, ethylen oxide-propylene oxide-block polymer, polyglycerol fatty acid ester, fatty acid alcanolamide and (ethoxylated) sorbitane fatty acid ester (sorbitane). A particularly preferred ethoxylated sorbitane fatty acid ester is polyoxyethylene sorbitane monoooleate, most preferably Polysorbate 80.

The at least one surfactant, such as the polyoxyethylene-type surfactant, can be present in an amount of from 1% to 10% (w/w), based on the total weight of the nanoemulsion (a), preferably from 2% to 10% (w/w), from 2% to 8% (w/w), and more preferably from 3% to 7% (w/w).

The formulation of the invention can comprise as least one hydrophilic surfactant with an HLB of 9 to 17, more preferably 12-16, particularly polysorbate 80.

The at least one surfactant can be a sugar-based surfactant. Sugar-based surfactants are a group of non-ionic surfactants using hydrophilic sugars to which hydrophobic tails are bound. One common substance of this class is n-dodecyl-B-D-maltoside, a member of the maltoside surfactants so named because the sugar unit used is maltose. An example of a pyranoside surfactant is n-octyl-β-D-thioglucopyranoside. This class uses pyranose as the sugar unit. Examples of the glycoside surfactants are octyl glucoside, decyl glucoside, and lauryl glucoside. An example of a polysugar surfactant is digitonin.

Another very important group of sugar-based surfactants are the Tween surfactants, most notable Tween 20 (also termed herein Polysorbate 20) and Tween 80 (also termed herein Polysorbate 80). These surfactants are based on a sorbitan sugar, which is why they are commonly referred to as polysorbate surfactants. Three oligo (ethylene glycol) side groups of varying lengths are bound to the sugar increasing the hydrophilicity of the head group. This structure forms the core of all Tween surfactants. They deviate in the hydrophobic tail, which is a fatty acid coupled via an ester to four oligo (ethylene glycol) tail. In Tween 20 this fatty acid is lauric acid; in Tween 80 it is oleic acid.

In the formulation as described herein, the at least one alcohol comprises no more than 5 carbon atoms and can have independently 3-5 or 3-4 carbon atoms. Particularly suitable alcohols having 5 carbon atoms are 1-pentanol and/or 4-methyl-2-pentanol. Suitable alcohols having 4 carbon atoms are 1-butyl alcohol, iso-butyl alcohol (2-methyl-1-propanol), tert-butyl alcohol (2-methyl-2-propanol) and/or sec-butyl alcohol (2-butanol).

Preferably, the at least one alcohol has 3-5 carbon atoms, even more preferably 3 carbon atoms, i.e. is selected from the group consisting of 1-propanol or 2-propanol (isopropyl alcohol) and mixtures thereof. A preferred alcohol is 2-propanol.

In the formulation as described herein, the alcohol may present in an amount of from 0.1% to 10% w/w based on the total weight of the nanoemulsion (a), preferably from 0.5% to 5% (w/w), and more preferably from 1% to 3% (w/w).

In the formulation as described herein, the alcohol may be a $C_3$ to $C_5$ alcohol present in an amount of from 1% to 5% (w/w) based on the total weight of the nanoemulsion (a).

In the formulation as described herein, any suitable propellant may be used. Suitable propellants and mixtures thereof are known to the skilled person. Preferably, the propellant is selected from propane, isobutane, n-butane and mixtures thereof. More preferably, the propellant is a mixture of propane and isobutane. In particular, the propellant is provided to pressurize the container in which the formulation of the invention is provided.

The formulation as described herein may comprise a gelling agent. The inventors have discovered that a gelling agent in the formulations described herein is not necessary to obtain a stable formulation or to form foams but may provide further resistance to formulation aging. Any suitable gelling agent may be used. Suitable gelling agents and mixtures thereof are known to the skilled person. In the formulation as described herein, the gelling agent may be selected from the group consisting of poloxamer, xanthan, bentonite, sodium carboxymethylcellulose, hydroxymethyl cellulose, carbomer, hydroxypropyl cellulose, gellan gum, guar gum, pectin, poly(ethylene)oxide, polycarbophil, alginate, tragacanth, povidone, gelatin, and mixtures thereof.

If the formulation of the invention comprises a gelling agent, it is preferred that the gelling agent is selected from poloxamer, xanthan and/or mixtures thereof.

If the formulation of the invention comprises a gelling agent, it is particularly preferred that the gelling agent is a poloxamer.

If the formulation of the invention comprises a gelling agent, it is particularly preferred that the gelling agent is xanthan (xanthan gum).

Poloxamers are nonionic triblock copolymers composed of a central hydrophobic chain of polyoxypropylene (poly (propylene oxide)) flanked by two hydrophilic chains of polyoxyethylene (poly(ethylene oxide)). Commercially available are Poloxamer 407 and Poloxamer 188.

Poloxamer 407 can have an average molecular weight of about 12600 Dalton. Poloxamer 188 can have an average molecular weight of about 8400 Dalton. In the formulation as described herein, a preferred poloxamer is Poloxamer 407.

In the formulation as described herein, the gelling agent may be present in an amount of from 0.1% to 10% w/w based on the total weight of the formulation, preferably from 0.25% to 5% (w/w), and more preferably from 0.5% to 4% (w/w).

The nanovesicles in the formulation of the present invention comprising a gelling again may have a size (or diameter) of less than or equal to 500 nm or less than or equal to 300 nm, preferably in the range of 5 nm to 200 nm, more preferably in the range of 5 nm to 150 nm, when subjected to at least one freeze-thaw cycle, preferably one, two, three, four or five freeze-thaw cycles. A freeze-thaw cycle may be as described herein.

The nanovesicles in the formulation of the present invention, containing at least one gelling agent, may have a size (or diameter) of less than or equal to 500 nm or less than or equal to 300 nm, preferably in the range of 5 nm to 200 nm, more preferably in the range of 5 nm to 150 nm, when stored at −15° C. to −25° C., preferably at −24° C., in a pressurized container, for example for 4 days.

Conditions of storage are as described herein.

In an embodiment, in the formulation as described herein, the at least one lipophilic component is present in an amount of from 0.1% to less than 15% (w/w), based on the total weight of the nanoemulsion (a), preferably from 0.1% to less than 10% (w/w), preferably from 0.25% to less than 10% (w/w), and more preferably from 0.5% to 8% (w/w) or 3% to 8% (w/w), and the formulation is essentially free of a gelling agent. In particular, the formulation is free of a gelling agent. In this embodiment, the formulation may be free of a poloxamer, such as Poloxamer 407 and Poloxamer 188. In this embodiment, the formulation may be free of xanthan. In this embodiment, the formulation may be free of xanthan and a poloxamer, such as Poloxamer 407 and Poloxamer 188. The at least one lipophilic component is as described herein.

In another embodiment, in the formulation as described herein,
(I) the at least one lipophilic component is present in an amount of from at least 10% to 30% (w/w) based on the total weight of the nanoemulsion (a), preferably from at least 15% to 30% (w/w), and more preferably from at least 20% to 30% (w/w), and
(II) the formulation comprises a gelling agent, in an amount of less than 10% based on the total weight of the formulation, in particular from 0.1% to 10% w/w based on the total weight of the formulation, preferably from 0.25% to 5% (w/w), and more preferably from 0.5% to 4% (w/w). In particular, the gelling agent is a poloxamer, such as Poloxamer 407 and/or Poloxamer 188, as described herein.

The at least one lipophilic component is as described herein.

The formulation as described herein may comprise a preservative. Any suitable preservative may be used. Suitable preservatives are known to the skilled person. The preservative can be selected from benzoate, citric acid, EDTA, potassium sorbate, vitamin C and/or derivatives and any mixtures thereof, wherein the preservative is preferably sodium benzoate. Suitable aqueous mixtures of sodium benzoate and potassium sorbate are commercially available, for example Euxyl™ k 712 preservative (Ashland).

The preservative can be present in the formulation as described herein in an amount of from 0.01% to 3% (w/w)

based on the total weight of the formulation, preferably from 0.2% to 2% (w/w) or 0.1-2% (w/w), and more preferably from 0.2% to 1.5% (w/w).

In particular, the formulation of the present inventions is essentially free of parabens, preferably free of parabens. The class of paraben compounds include p-hydroxybenzoates and esters of p-hydroxybenzoic acid (also known as 4-hydroxybenzoic acid).

Parabens are only slightly soluble in water. In the preparation of an aqueous formulation or a formulation comprising an aqueous component, parabens must be solved in a solvent suitable to introduce the parabens in the aqueous phase. A suitable solvent is propylene glycol.

In the context of the present specification, the term "propylene glycol" refers to propane-1,2-diol (also known as 1,2-propanediol, α-propylene glycol, 1,2-dihydroxypropane, methyl ethyl glycol or methylethylene glycol).

In the present invention, this preparation of a solution of a paraben in propylene glycol is not needed, so the formulation of the present invention can be free of propylene glycol.

The formulation of the present inventions can be essentially free of propylene glycol, preferably free of propylene glycol.

The formulation of the present inventions can be essentially free of propylene glycol and a paraben, preferably free of propylene glycol and a paraben.

In addition to comprising no propylene glycol or only small amounts of propylene glycol as defined above, it is preferred that the formulation comprises no, essentially no or less than 0.9% 0.8%, 0.7%. 0.6%, 0.5%, 0.4%, 0.3%, 0.2%, or 0.1% w/w of a non-cyclic polyol having 2 to 3 carbon atoms (i.e., having not more than 3). Preferably, the formulation comprises no, essentially no or less than 0.9% 0.8%, 0.7%. 0.6%, 0.5%, 0.4%, 0.3%, 0.2%, or 0.1% w/w of a non-cyclic polyol having 2 to 4, 2 to 5, 2 to 6, 2 to 7, 2 to 8, 2 to 9 or 2 to 10 carbon atoms (i.e., having not more than 4, 5, 6, 7, 8, 9, or 10 carbon atoms, respectively). More preferably, the formulation comprises no, essentially no or less than 0.9%, 0.8%, 0.7%. 0.6%, 0.5%, 0.4%, 0.3%, 0.2%, or 0.1% w/w of a polyol having 2 to 4, 2 to 5, 2 to 6, 2 to 7, 2 to 8, 2 to 9, 2 to 10, 2 to 11 or 2 to 12 carbon atoms (i.e., having not more than 4, 5, 6, 7, 8, 9, 10, 11 or 12 carbon atoms, respectively). More preferably, the formulation comprises no, essentially no or less than 0.9% 0.8%, 0.7%. 0.6%, 0.5%, 0.4%, 0.3%, 0.2%, or 0.1% w/w of a non-cyclic polyol having 2 to 15, 2 to 20, 2 to 25 or 2 to 30 carbon atoms (i.e., having not more than 15, 20, 25 or 30 carbon atoms, respectively). Even more preferably, the formulation comprises no, essentially no or less than 0.9%, 0.8%, 0.7%. 0.6%, 0.5%, 0.4%, 0.3%, 0.2%, or 0.1% w/w of a polyol having 2 to 15, 2 to 20, 2 to 25 or 2 to 30 carbon atoms (i.e., having not more than 15, 20, 25 or 30 carbon atoms, respectively). Even more preferably, the formulation comprises no, essentially no or less than 0.9% 0.8%, 0.7%. 0.6%, 0.5%, 0.4%, 0.3%, 0.2%, or 0.1% w/w of a non-cyclic polyol.

"Non-cyclic polyol" in the context of the present specifications means that the polyol does not comprise any cyclic hydrocarbon moieties, in particular no cyclic sugar moieties. The non-cyclic polyol may be linear or branched. The non-cyclic polyol may be a diol, a triol or may comprise more than three OH groups.

In preferred embodiments, the formulation of the invention comprises no, essentially no or less than 0.9%, 0.8%, 0.7%. 0.6%, 0.5%, 0.4%, 0.3%, 0.2%, or 0.1% w/w of a polyol having a molecular weight of less than 100 g/mol, less than 200 g/mol, less than 300 g/mol, less than 400 g/mol, less than 500 g/mol, less than 600 g/mol, less than 700 g/mol, less than 800 g/mol, less than 900 g/mol, or less than 1000 g/mol.

As used herein, the expressions "essentially free of compound X", "does essentially not comprise compound X", or "comprises essentially no compound X" with respect to a formulation are interchangeable. In particular, unless defined otherwise, these expressions specify that the formulation is either free of compound X or comprises less than 0.1% (w/w), less than 0.08% (w/w), less than 0.07% (w/w), less than 0.06% (w/w), less than 0.05% (w/w), less than 0.04% (w/w), less than 0.03% (w/w), less than 0.02% (w/w), or less than 0.01% (w/w) of compound X based on the total weight of the formulation.

As used herein, the expression "the composition comprises less than X % of compound X", is meant to include embodiments in which the composition is essentially free of compound X.

As used herein, "the formulation comprises essentially no propylene glycol" or "the formulation essentially does not comprise propylene glycol" means that the formulation is essentially free of propylene glycol. In particular, the pharmaceutical formulation of the invention is free of propylene glycol, i.e. the formulation does not comprise propylene glycol.

The formulation of the present invention may be essentially free of propylene glycol.

The formulation of the present invention may be essentially free of glycerin.

The formulation of the present invention may be essentially free of diglycerin.

The formulation of the present invention may be essentially free of polyglycerin.

The formulation of the present invention may be essentially free of diethylene glycol.

The formulation of the present invention may be essentially free of dipropylene glycol.

The formulation of the present invention may be essentially free of butylene glycol.

The formulation of the present invention may be essentially free of pentylene glycol.

The formulation of the present invention may be essentially free of hexylene glycol.

The formulation of the present invention may be essentially free of 1,3-propanediol.

The formulation of the present invention may be essentially free of 1,5-pentanediol.

The formulation of the present invention may be essentially free of octane-1,2-diol.

The formulation of the present invention may be essentially free of polyethylene glycols, particularly having from 2 to 50 ethylene oxide groups.

The formulation of the present invention may be essentially free of monosaccharides and disaccharides such as sorbitol, mannitol, and mixtures thereof.

The formulation of the present invention may comprise less than or equal to 0.9%, 0.8%, 0.7%. 0.6%, 0.5%, 0.4%, 0.3%, 0.2%, or 0.1% w/w of propylene glycol or no propylene glycol. This formulation may be free of a paraben, as described herein.

In particular, the formulation of the present invention may comprise less than or equal to 0.7%, 0.5%, 0.3% or 0.1% w/w of propylene glycol. This formulation may be free of a paraben, as described herein.

More particular, the formulation of the present invention may comprise less than or equal to 0.5%, 0.3% or 0.1% w/w of propylene glycol. This formulation may be free of a paraben, as described herein.

Most particular, the formulation of the present invention may comprise less than or equal to 0.3% or 0.1% w/w of propylene glycol. This formulation may be free of a paraben, as described herein.

In preferred embodiments, the formulation of the present invention comprises no propylene glycol.

The formulation of the present invention may comprise less than or equal to 0.9%, 0.8%, 0.7%. 0.6%, 0.5%, 0.4%, 0.3%, 0.2%, or 0.1% w/w of glycerin or no glycerin. This formulation may be free of a paraben, as described herein.

In particular, the formulation of the present invention may comprise less than or equal to 0.7%, 0.5%, 0.3% or 0.1% w/w of glycerin. This formulation may be free of a paraben, as described herein.

More particular, the formulation of the present invention may comprise less than or equal to 0.5%, 0.3% or 0.1% w/w of glycerin. This formulation may be free of a paraben, as described herein.

Most particular, the formulation of the present invention may comprise less than or equal to 0.3% or 0.1% w/w of glycerin. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of diglycerin or no diglycerin. This formulation may be free of a paraben, as described herein.

In particular, the formulation of the present invention may comprise less than or equal to 0.7%, 0.5%, 0.3% or 0.1% w/w of diglycerin. This formulation may be free of a paraben, as described herein.

More particular, the formulation of the present invention may comprise less than or equal to 0.5%, 0.3% or 0.1% w/w of diglycerin. This formulation may be free of a paraben, as described herein.

Most particular, the formulation of the present invention may comprise less than or equal to 0.3% or 0.1% w/w of diglycerin. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of polyglycerin or no polyglycerin. This formulation may be free of a paraben, as described herein.

In particular, the formulation of the present invention may comprise less than or equal to 0.7%, 0.5%, 0.3% or 0.1% w/w of polyglycerin. This formulation may be free of a paraben, as described herein.

More particular, the formulation of the present invention may comprise less than or equal to 0.5%, 0.3% or 0.1% w/w of polyglycerin. This formulation may be free of a paraben, as described herein.

Most particular, the formulation of the present invention may comprise less than or equal to 0.3% or 0.1% w/w of polyglycerin. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of diethylene glycol or no diethylene glycol. This formulation may be free of a paraben, as described herein.

In particular, the formulation of the present invention may comprise less than or equal to 0.7%, 0.5%, 0.3% or 0.1% w/w of diethylene glycol. This formulation may be free of a paraben, as described herein.

More particular, the formulation of the present invention may comprise less than or equal to 0.5%, 0.3% or 0.1% w/w of diethylene glycol. This formulation may be free of a paraben, as described herein.

Most particular, the formulation of the present invention may comprise less than or equal to 0.3% or 0.1% w/w of diethylene glycol. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of dipropylene glycol or no dipropylene glycol. This formulation may be free of a paraben, as described herein.

In particular, the formulation of the present invention may comprise less than or equal to 0.7%, 0.5%, 0.3% or 0.1% w/w of dipropylene glycol. This formulation may be free of a paraben, as described herein.

More particular, the formulation of the present invention may comprise less than or equal to 0.5%, 0.3% or 0.1% w/w of dipropylene glycol. This formulation may be free of a paraben, as described herein.

Most particular, the formulation of the present invention may comprise less than or equal to 0.3% or 0.1% w/w of dipropylene glycol. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of butylene glycol or no butylene glycol. This formulation may be free of a paraben, as described herein.

In particular, the formulation of the present invention may comprise less than or equal to 0.7%, 0.5%, 0.3% or 0.1% w/w of butylene glycol. This formulation may be free of a paraben, as described herein.

More particular, the formulation of the present invention may comprise less than or equal to 0.5%, 0.3% or 0.1% w/w of butylene glycol. This formulation may be free of a paraben, as described herein.

Most particular, the formulation of the present invention may comprise less than or equal to 0.3% or 0.1% w/w of butylene glycol. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of pentylene glycol or no pentylene glycol. This formulation may be free of a paraben, as described herein.

In particular, the formulation of the present invention may comprise less than or equal to 0.7%, 0.5%, 0.3% or 0.1% w/w of pentylene glycol. This formulation may be free of a paraben, as described herein.

More particular, the formulation of the present invention may comprise less than or equal to 0.5%, 0.3% or 0.1% w/w of pentylene glycol. This formulation may be free of a paraben, as described herein.

Most particular, the formulation of the present invention may comprise less than or equal to 0.3% or 0.1% w/w of pentylene glycol. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of hexylene glycol or no hexylene glycol. This formulation may be free of a paraben, as described herein.

In particular, the formulation of the present invention may comprise less than or equal to 0.7%, 0.5%, 0.3% or 0.1% w/w of hexylene glycol. This formulation may be free of a paraben, as described herein.

More particular, the formulation of the present invention may comprise less than or equal to 0.5%, 0.3% or 0.1% w/w of hexylene glycol. This formulation may be free of a paraben, as described herein.

Most particular, the formulation of the present invention may comprise less than or equal to 0.3% or 0.1% w/w of hexylene glycol. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of 1,3-propanediol or no 1,3-propanediol. This formulation may be free of a paraben, as described herein.

In particular, the formulation of the present invention may comprise less than or equal to 0.7%, 0.5%, 0.3% or 0.1% w/w of 1,3-propanediol. This formulation may be free of a paraben, as described herein.

More particular, the formulation of the present invention may comprise less than or equal to 0.5%, 0.3% or 0.1% w/w of 1,3-propanediol. This formulation may be free of a paraben, as described herein.

Most particular, the formulation of the present invention may comprise less than or equal to 0.3% or 0.1% w/w of 1,3-propanediol. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of 1,5-pentanediol or no 1,5-pentanediol. This formulation may be free of a paraben, as described herein.

In particular, the formulation of the present invention may comprise less than or equal to 0.7%, 0.5%, 0.3% or 0.1% w/w of 1,5-pentanediol. This formulation may be free of a paraben, as described herein.

More particular, the formulation of the present invention may comprise less than or equal to 0.5%, 0.3% or 0.1% w/w of 1,5-pentanediol. This formulation may be free of a paraben, as described herein.

Most particular, the formulation of the present invention may comprise less than or equal to 0.3% or 0.1% w/w of 1,5-pentanediol. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of octane-1,2-diol or no octane-1,2-diol. This formulation may be free of a paraben, as described herein.

In particular, the formulation of the present invention may comprise less than or equal to 0.7%, 0.5%, 0.3% or 0.1% w/w of octane-1,2-diol. This formulation may be free of a paraben, as described herein.

More particular, the formulation of the present invention may comprise less than or equal to 0.5%, 0.3% or 0.1% w/w of octane-1,2-diol. This formulation may be free of a paraben, as described herein.

Most particular, the formulation of the present invention may comprise less than or equal to 0.3% or 0.1% w/w of octane-1,2-diol. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of polyethylene glycols or no polyethylene glycols, particularly having from 2 to 50 ethylene oxide groups. This formulation may be free of a paraben, as described herein.

In particular, the formulation of the present invention may comprise less than or equal to 0.7%, 0.5%, 0.3% or 0.1% w/w of polyethylene glycols, particularly having from 2 to 50 ethylene oxide groups. This formulation may be free of a paraben, as described herein.

More particular, the formulation of the present invention may comprise less than or equal to 0.5%, 0.3% or 0.1% w/w of polyethylene glycols, particularly having from 2 to 50 ethylene oxide groups. This formulation may be free of a paraben, as described herein.

Most particular, the formulation of the present invention may comprise less than or equal to 0.3% or 0.1% w/w of polyethylene glycols, particularly having from 2 to 50 ethylene oxide groups. This formulation may be free of a paraben, as described herein.

The formulation of the present invention may comprise less than or equal to 0.9%, 0.8%, 0.7%. 0.6%, 0.5%, 0.4%, 0.3%, 0.2%, or 0.1% w/w of monosaccharides and disaccharides such as sorbitol, mannitol and mixtures thereof. This formulation may be free of a paraben, as described herein.

In particular, the formulation of the present invention may comprise less than or equal to 0.7%, 0.5%, 0.3% or 0.1% w/w of monosaccharides and disaccharides such as sorbitol, mannitol and mixtures thereof or no monosaccharides and disaccharides such as sorbitol, mannitol and mixtures thereof. This formulation may be free of a paraben, as described herein.

More particular, the formulation of the present invention may comprise less than or equal to 0.5%, 0.3% or 0.1% w/w of monosaccharides and disaccharides such as sorbitol, mannitol and mixtures thereof. This formulation may be free of a paraben, as described herein.

Most particular, the formulation of the present invention may comprise less than or equal to 0.3% or 0.1% w/w of monosaccharides and disaccharides such as sorbitol, mannitol and mixtures thereof. This formulation may be free of a paraben, as described herein.

The formulation of the present invention may be free of, may be essentially free of or may comprise less than an indicated amount, such as less than 0.9%, less than 0.8%, less than 0.7%, less than 0.6%, less than 0.5%, less than 0.4%, less than 0.3%, less than 0.2% or less than 0.1% of one polyol, all polyols or any chosen number of polyols selected from the group consisting of glycerin, diglycerin, polyglycerin, diethylene glycol, propylene glycol, dipropylene glycol, butylene glycol, pentylene glycol, hexylene glycol, 1,3-propanediol, 1,5-pentanediol, octane-1,2-diol, polyethyleneglycols, particularly having from 2 to 50 ethylene oxide groups, and sugars such as sorbitol, mannitol and mixtures thereof. The formulation of the present invention may be essentially free of one polyol or any chosen number of polyols selected from the group consisting of glycerin, diglycerin, polyglycerin, diethylene glycol, propylene glycol, dipropylene glycol, butylene glycol, pentylene glycol, hexylene glycol, 1,3-propanediol, 1,5-pentanediol, octane-1,2-diol, polyethyleneglycols, particularly having from 2 to 50 ethylene oxide groups, and monosaccharides or disaccharides such as sorbitol, mannitol and mixtures thereof, but may comprise another polyol. The formulation of the present invention may be essentially free of a polyol that is linear or branched. The formulation of the present invention may be essentially free of a polyol having a carbon atom number of 2 to 30, more preferably 2 to 20, even more preferably 2 to 10 or 2 to 8, most preferably 2 to 6 or 2 to 3.

In particular, the formulation of the present invention may be essentially free of a polyol having a carbon atom number of 2 to 8 or 2 to 6.

The formulation of the present invention may comprise less than or equal to 0.9%, 0.8%, 0.7%. 0.6%, 0.5%, 0.4%, 0.3%, 0.2%, or 0.1% w/w of a polyol or no polyol. The polyol may be a polyol as described herein. This formulation may be free of a paraben, as described herein.

The formulation of the present invention may comprise less than or equal to 0.7%, 0.5%, 0.3% or 0.1% w/w of a polyol. The polyol may be a polyol as described herein. This formulation may be free of a paraben, as described herein.

The formulation of the present invention may comprise less than or equal to 0.5%, 0.3% or 0.1% w/w of a polyol. The polyol may be a polyol as described herein. This formulation may be free of a paraben, as described herein.

The formulation of the present invention may comprise less than or equal to 0.3% or 0.1% w/w of a polyol. The polyol may be a polyol as described herein. This formulation may be free of a paraben, as described herein.

The formulation of the present invention may be essentially free of a polyol.

The formulation of the present inventions can be essentially free of a polyol, as described herein, and a paraben, preferably free of a polyol and a paraben, as described herein.

The formulation as described herein can contain an active agent. The active agent may be present in an amount of from 0.0001% to 50% w/w, based on the total weight of the formulation. In particular, the active agent may be present in an amount of from 0.001% to 50% w/w, based on the total weight of the formulation, in an amount of from 0.01% to 30% w/w, based on the total weight of the formulation, or 0.01% to 10% w/w, based on the total weight of the formulation. In embodiments where the formulation comprises an active agent, the active is agent is either Tacrolimus or is not Tacrolimus.

Tacrolimus (also termed herein "TC") is a macrolide lactone molecule harvested from the soil bacterium *Streptomyces tsukubaensis*. In pharmaceutical medicine, it is described as a calcineurin inhibitor with immunosuppressant capacity. It is applied topically to treat immune system mediated skin conditions such as atopic dermatitis or psoriasis. TC is a molecule with a molecular weight of 804.03 g/mol and very lipophilic properties (log P>3), i.e. by six orders of magnitude more lipophilic than ALA. Due to its very lipophilic nature, TC has been formulated in mixtures of mineral oil, paraffin, propylene carbonate, white petrolatum and white wax. TC has previously been found to be weakly stable in aqueous formulations (approx. 90 days at room temperature).

In preferred embodiments, the active is agent is not Tacrolimus. In embodiments where the active agent is not Tacrolimus, the active agent is another active agent, such as, for example, 5-aminolevulinic acid.

In some embodiments, the active is agent is not a highly lipophilic macrolide lactone.

In some embodiments, the active is agent is not a macrolide lactone having a log P value of 3.0 or higher, wherein P is the octanol-water partition-coefficient.

In some embodiments, the active is agent is not Tacrolimus, Pimecrolimus, Everolimus or Sirolimus, a derivative, a precursor, a metabolite, hydrate, and/or a pharmaceutically acceptable salt thereof.

In preferred embodiments, the active agent is a biogenic substance. In the context of the present specification, the term "biogenic substance" is a substance that is produced or can be produced by a living organism. For example, 5-aminolevulinic acid is a biogenic substance that is produced by living organisms including plants, algae, bacteria, fungi and animals. 5-aminolevulinic acid can also by produced in vitro by chemical synthesis. Since it can be produced by a living organism, 5-aminolevulinic acid is a biogenic substance the context of the present specification, regardless of whether it was produced by chemical synthesis or by a living organism.

As used herein, "active agent", includes an active pharmaceutical agent (herein also termed "pharmaceutical active agent" or "active pharmaceutical ingredient", "API") and an active cosmetic agent (herein also termed "cosmetic active agent"). As used herein, an active pharmaceutical agent is defined as the chemical, biological, mineral or any other entity or component responsible for the therapeutic (pharmacological, physiological, physical, etc.) effects in a product. As used herein, an active cosmetic agent is defined as the chemical, biological, mineral or any other entity or component responsible for the cosmetic effects in a product. The active agent may be a plant extract.

The formulations of the invention provide a very efficient delivery system for a wide variety of active agents. The active agent may be any agent suitable in a pharmaceutical or cosmetic use as described herein. Examples of active agents that may be useful include, but are not limited to an anti-infective, an antibiotic, an antibacterial agent, an antifungal agent, an antiviral agent, an antiparasitic agent, a steroidal anti-inflammatory agent, a non-steroidal anti-inflammatory agent, an immunosuppressive agent, an immunomodulator, an immunoregulating agent, a hormonal agent, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, Vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, an anti-wrinkle agent, a radical scavenger, a chemical sunscreen, a metal oxide (e.g., titanium dioxide, Zinc oxide, Zirconium oxide, iron oxide), silicone oxide, an anti-wrinkle agent, a skin whitening agent, a skin protective agent, a masking agent, an anti-wart agent, and a refatting agent.

The active agent may be a hydrophilic agent, such as 5-aminolevulinic acid, which can be dissolved in the aqueous phase (or aqueous component) and is capable to interact with the surface of the nanovesicles. The active agent may also be a hydrophobic agent, such as diclofenac or tacrolimus, which can be dissolved in the lipid phase (or the carrier component) and thus be incorporated in the lipid core of the nanovesicles.

Another aspect of the present invention relates to the formulation of the first aspect as described herein which is a pharmaceutical formulation.

In the formulation as described herein, in particular the pharmaceutical formulation, the active agent may be a small organic molecule, for example with a molecular weight of from 50 to 2500 g/mol, preferably from 100 to 1000 g/mol, more preferably from 115 to 950 g/mol, and even more preferably from 130 to 900 g/mol.

The active agent may be present in the form of a pharmaceutically and/or cosmetically acceptable salts, such as hydrochloride, phosphates, acetates, sodium and sulfates. The active agent may be present in the form of a pharmaceutically and/or cosmetically acceptable derivatives or analog such as esters, ethers, (methyl-) thioester, (methyl-) thioethers, methoxy-substituted benzyl ethers, silyl ethers, sulfonates, sulfenates, sulfinates, (cyclic) carbonates, carbamates, cyclic acetals or ketals, (chiral) ketones, hydrazones, enamines and enols. Such derivatives or protecting groups are well known for a person skilled in the art and are not limited to the mentioned groups.

In particular, the formulation of the present invention may comprise or consist of:
(a) a nanoemulsion comprising
    (i) an aqueous component, present in an amount of 60 to 96% w/w, preferably 70-95% w/w, based on the total weight of the nanoemulsion (a).
    (ii) nanovesicles, comprising
        (1) 1-5% of at least one phospholipid, based on the total weight of the nanoemulsion (a);
        (2) 2-10% of at least one polyoxyethylene-type surfactant, based on the total weight of the nanoemulsion (a);
        (3) 1-5% $C_3$ to $C_5$ alcohol, based on the total weight of the nanoemulsion (a); and (4) 2-10% triglycerides, based on the total weight of the nanoemulsion (a);
(b) 0.0001-50%, preferably 0.001-30% of a pharmaceutically active organic molecule with a molecular weight from 100 to 1000 g/mol, preferably from 115 to 950 g/mol, and more preferably from 130 to 900 g/mol.
(c) optionally 0.5-4% of at least one gelling agent, based on the total weight of the formulation;
(d) optionally 0.1-2% of at least one preservative, based on the total weight of the formulation; and
(e) a propellant.

In instances where the active agent is Tacrolimus and/or a pharmaceutically acceptable analog or derivative thereof, Tacrolimus may be present in an amount of from 0.001-5% w/w, based on the total weight of the formulation. In particular, tacrolimus may be present in an amount of from 0.01-3% w/w, based on the total weight of the formulation, or 0.05-1% w/w, based on the total weight of the formulation, or 0.01-1%, based on the total weight of the formulation.

In instances where the active agent is Tacrolimus, the formulation of the present invention may comprise or consist of:
(a) a nanoemulsion comprising
    (i) an aqueous component, present in an amount of 70-95% w/w, based on the total weight of the nanoemulsion (a).
    (ii) nanovesicles, comprising
        (1) 1-5% of at least one phospholipid, based on the total weight of the nanoemulsion (a);
        (2) 2-10% of at least one polyoxyethylene-type surfactant, based on the total weight of the nanoemulsion (a);
        (3) 1-5% $C_3$ to $C_5$ alcohol, based on the total weight of the nanoemulsion (a); and (4) 2-10% triglycerides, based on the total weight of the nanoemulsion (a);

(b) 0.01-1% tacrolimus, based on the total weight of the formulation;
(c) optionally 0.5-4% of at least one gelling agent, based on the total weight of the formulation;
(d) optionally 0.1-2% of at least one preservative, based on the total weight of the formulation; and
(e) a propellant.

The active agent may be a photosensitizer or a metabolic photosensitizer precursor, such as 5-aminolevulinic acid (also termed herein "ALA" or "5-ALA"), a pharmaceutically acceptable salt, a derivative, precursor and/or metabolite thereof. A preferred salt of 5-aminolevulinic acid is 5-aminolevulinic acid hydrochloride.

5-Aminolevulinic acid has the following chemical structure:

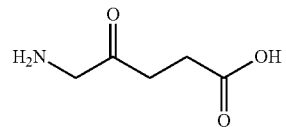

Molecular Weight: 131.13 g/mol

5-Aminolevulinic acid and/or a pharmaceutically acceptable salt thereof may be present in an amount of from 0.1-30% w/w, based on the total weight of the formulation. In particular, 5-aminolevulinic acid and/or a pharmaceutically acceptable salt, ester or other pharmaceutically relevant derivative, such as methyl-, or hexyl aminolevulinic acid thereof may be present in an amount of from 1-20% w/w, based on the total weight of the formulation, or 1-10% w/w, based on the total weight of the formulation.

The active agent may be a nonsteroidal anti-inflammatory drug (NSAID), such as Diclofenac, a pharmaceutically acceptable salt, a derivative, precursor and/or metabolite thereof.

Diclofenac has the following chemical structure:

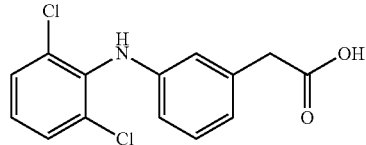

Molecular Weight: 296.15

Diclofenac and/or a pharmaceutically acceptable salt thereof may be present in an amount of from 0.01-30% w/w, based on the total weight of the formulation. In particular, diclofenac and/or a pharmaceutically acceptable salt, ester or other pharmaceutically relevant derivative may be present in an amount of from 0.1-20% w/w, based on the total weight of the formulation, or 0.1-10% w/w, based on the total weight of the formulation.

Another aspect of the present invention relates to the formulation of the first aspect as described herein which is a cosmetic formulation.

In the cosmetic formulation of the present invention, the active agent is a cosmetic active agent. In particular, the cosmetic active agent is selected from plant extracts, natural or synthetic moisturizers, natural or synthetic cleaning agents, natural or synthetic protective agents, natural or synthetic detergents, natural or synthetic anti-oxidants, natural or synthetic skin conditioning agents and natural or synthetic vitamins.

Suitable plant extracts include, but are not limited to extracts obtained from *Mahonia* root, *Matricaria chamomilla*, *Camellia sinensis*, *Salvia officinalis* (common sage), *Achillea millefolium*, *Hamamelis virginiana*, yeast, *Glycyrrhiza glabra* (liquorice), Shea tree (e.g., shea butter), plant oils that contain squalan, avocado and *Acmella oleracea* (main compound: spilanthol), and mixtures thereof. An extract of *Salvia officinalis* or *Mahonia* is preferred. Also, the plant extracts disclosed in Faccio, 2020, (iScience 23, 101358, Aug. 21, 2020), the disclosure of which is included herein by reference, are suitable cosmetic ingredients in the formulation of the present invention.

Also suitable cosmetic active agents include, but are not limited to berberine (alkaloid from *Mahonia aquifolium*, can be found also in other plants) and α-(−)-bisabolol (monocyclic sesquiterpene alcohol, can be found in German chamomile).

The cosmetic formulation of the present invention can be used to moisturize skin, clean the skin, protect from sun (UV rays) or other external influences, help maintain skin barrier function, beautify the skin, reduce signs of skin ageing, and as supportive care for stressed skin or diseased skin.

In particular, the formulation of the first aspect of the present invention may comprise or consist of:
(a) a nanoemulsion comprising
  (i) an aqueous component, present in an amount of 70% to 95% w/w, based on the total weight of the nanoemulsion (a);
  (ii) nanovesicles, comprising
    (1) 1-5% of at least one phospholipid, based on the total weight of the nanoemulsion (a);
    (2) 2-10% of at least one polyoxyethylene-type surfactant, based on the total weight of the nanoemulsion (a);
    (3) 1-5% $C_3$ to $C_5$ alcohol, based on the total weight of the nanoemulsion (a); and (4) 2-10% triglycerides, based on the total weight of the nanoemulsion (a);
(b) 1-20% of a photosensitizer or a metabolic precursor thereof, preferably 5-aminolevulinic acid hydrochloride, based on the total weight of the formulation;
(c) optionally 0.5-4% of at least one gelling agent, based on the total weight of the formulation;
(d) optionally 0.1-2% of at least one preservative, based on the total weight of the formulation; and
(e) a propellant.

The formulation comprising 5-aminolevulinic acid and/or a pharmaceutically acceptable salt thereof, the aqueous component, may contain the at least one phospholipid, the at least one polyoxyethylene-type surfactant, the $C_3$ to $C_5$ alcohol, the triglycerides, the gelling agent, the at least one preservative, and the propellant independently selected according to the herein-described disclosure.

The present invention also relates to a nanovesicle, comprising
(i) 16-19% w/w of soy lecithin,
(ii) 32-36% w/w of Polysorbate 80,
(iii) 32-36% w/w of caprylic/capric triglycerides, and
(iv) 12-16% w/w of isopropyl alcohol.
A preferred nanovesicle of the invention comprises
(i) 17% w/w of soy lecithin
(ii) 34% w/w of Polysorbate 80
(iii) 35% w/w of caprylic/capric triglycerides
(iv) 14% w/w of isopropyl alcohol.

The present invention also relates to a nanoemulsion, comprising
(a) 1.6-3.6% w/w of soy lecithin
(b) 3.3-6.9% w/w of Polysorbate 80
(c) 3.3-7.0% w/w of caprylic/capric triglycerides
(d) 1.3-2.9% w/w of isopropyl alcohol
(e) aqueous phosphate buffer, for example aqueous 5-20 mM phosphate buffer, pH 2-8, preferably pH 2-7, more preferably pH 3-6, ad 100%.

A preferred nanoemulsion of the present invention comprises:
(a) 1.7% w/w of soy lecithin
(b) 3.4% w/w of Polysorbate 80
(c) 3.5% w/w of caprylic/capric triglycerides
(d) 1.4% w/w of isopropyl alcohol
(e) aqueous 10 mM phosphate buffer, pH 6, ad 100%.

This formulation is termed herein "BF200". The BF200 nanoemulsion can be obtained by contacting a mixture of ingredients (a)-(d) in a total amount of 10% w/w and 90% w/w of an aqueous 10 mM phosphate buffer, pH 6, under condition allowing formation of a nanoemulsion, thereby forming the nanoemulsion. An exemplary method for manufacture of the BF200 formulation is described in Example 1.

Another preferred nanoemulsion of the present invention comprises:
(a) 2-3% w/w of soy lecithin
(b) 4.5-5.5% w/w of Polysorbate 80
(c) 4.5-5.5% w/w of caprylic/capric triglycerides
(d) 2-3% w/w of isopropyl alcohol
(e) aqueous 10 mM phosphate buffer, pH 6, ad 100%.

This formulation is termed herein "BF215". The BF215 nanoemulsion can be obtained by contacting a mixture of ingredients (a)-(d) in a total amount of 15% w/w and 85% w/w of an aqueous 10 mM phosphate buffer, pH 6, under condition allowing formation of a nanoemulsion, thereby forming the nanoemulsion. An exemplary method for manufacture of the BF215 formulation is described in Example 1.

Yet another preferred nanoemulsion of the present invention comprises:
(a) 3-4% w/w of soy lecithin
(b) 6-7% w/w of Polysorbate 80
(c) 6-8% w/w of caprylic/capric triglycerides
(d) 2-4% w/w of isopropyl alcohol
(e) aqueous 10 mM phosphate buffer, pH 6, ad 100%.

This formulation is termed herein "BF220". The BF220 nanoemulsion can be obtained by contacting a mixture of ingredients (a)-(d) in a total amount of 20% w/w and 80% w/w of an aqueous 10 mM phosphate buffer, pH 6, under condition allowing formation of a nanoemulsion, thereby forming the nanoemulsion. An exemplary method for manufacture of the BF220 formulation is described in Example 1.

A preferred formulation of the present invention comprises:
(1) 17.5% nanoemulsion BF200, as described herein,
(2) 0-4% w/w Poloxamer 407
(3) 0.1-0.3% w/w sodium benzoate
(4) 3% w/w 5-ALA hydrochloride
(5) water, ad 100%

This formulation may have a pH of 2.5-3.5.

Another preferred formulation of the present invention comprises:
(1) 17.5% nanoemulsion BF200, as described herein,
(2) 0-4% w/w Poloxamer 407
(3) 0.1-0.3% w/w sodium benzoate
(4) 3% w/w 5-ALA hydrochloride
(5) water, ad 100%.

This formulation may have a pH of 2.5-3.5.

Yet another preferred formulation of the present invention comprises:
(1) 35% nanoemulsion BF200, as described herein,
(2) 2-4% w/w Poloxamer 407
(3) 0.1-0.3% w/w sodium benzoate
(4) 3% w/w 5-ALA hydrochloride
(5) water, ad 100%.
This formulation may have a pH of 2.5-3.5.

Yet another preferred formulation of the present invention comprises:
(1) 18-20% nanoemulsion BF220, as described herein,
(2) 0-4% w/w Poloxamer 407
(3) 0.1-0.3% w/w sodium benzoate
(4) 0.1-1% w/w citric acid
(5) 0-1% w/w EDTA
(6) 0-1% w/w α-tocopheryl acetate
(7) 0.03, 0.06 or 0.1% w/w tacrolimus
(8) water, ad 100%
This formulation may have a pH of 3.0-4.0.

Yet another preferred formulation of the present invention comprises:
(1) 18-20% nanoemulsion BF200, as described herein,
(2) 0-4% w/w Poloxamer 407
(3) 0-1% w/w xanthan gum
(4) 4-6% w/w pentylene glycol
(5) 0-2% w/w of aqueous mixture of water, sodium benzoate and sodium sorbate (e.g., Euxyl 712 K)
(9) 0-1% w/w α-tocopheryl acetate
(6) 0-1% w/w perfume
(7) 0-1% w/w D-panthenol
(8) 10% propellant (mixture of isobutane, n-butane and propane)
(9) 1-3% w/w *Mahonia* extract
(10) Water, ad 100%.
This formulation may have a pH of 5.0-6.5.

Formulations of the first aspect of the invention comprise the above described preferred formulations and further a propellant and are comprised in a pressurized container. The formulations of the first aspect of the invention comprise essentially no fatty alcohol.

All terms defined with respect to the first aspect of the invention have the same meaning when used with respect to other aspects of the invention, where applicable and unless specifically defined otherwise. Further, all embodiments specified for the first aspect of the invention are also envisaged for the other aspects of the invention, where applicable.

Another aspect of the present invention is a formulation, said formulation comprising
(a) a nanoemulsion comprising:
  (i) at least one aqueous component;
  (ii) a carrier component comprising:
    (1) at least one lipophilic component,
    (2) at least one surfactant, and
    (3) at least one alcohol,
  (iii) optionally an active agent
    (1) dissolved in the aqueous phase and capable to interact with the surface of the nanovesicles, and/or
    (2) dissolved in the lipid core of the nanovesicles,
(b) optionally a gelling agent,
wherein the formulation is provided in a container further comprising a propellant, wherein the propellant is provided to pressurize the container. The nanoemulsion (a) is a nanoemulsion as described herein. In contrast to the formulation of the first aspect, in this formulation, the propellant is not defined as integral component of the formulation. Instead, the formulation is defined as such, and the propellant is provided to pressurize the container in which the formulation is comprised. In preferred embodiments, the formulation of this aspect comprises essentially no atty alcohol, preferably essentially no foam adjuvant. In preferred embodiments, the formulation of this aspect comprises essentially no fatty alcohol, preferably essentially no foam adjuvant. The optional gelling agent (b) is a gelling agent as described herein. The propellant, provided to pressurize the container is a propellant, as described herein.

The container can be a container, as described herein, in particular a dispenser, such as a foam dispenser or a spray dispenser, preferably a foam dispenser, as described herein.

The formulation provided in a container may be used in medicine. The medical use may be any medical use as described herein, in particular the treatment and/or prevention of a dermatological disease or condition in a subject, as described herein.

Another aspect of the present invention is a formulation, said formulation comprising
(a) a nanoemulsion comprising:
  (i) at least one aqueous component;
  (ii) a carrier component comprising:
    (1) at least one lipophilic component,
    (2) at least one surfactant, and
    (3) at least one alcohol,
  (iii) optionally an active agent
    (1) dissolved in the aqueous phase and capable to interact with the surface of the nanovesicles, and/or
    (2) dissolved in the lipid core of the nanovesicles,
(b) optionally a gelling agent,
wherein the formulation is prepared as a pressurized formulation, wherein a propellant is provided to pressurize the formulation. The nanoemulsion (a) is a nanoemulsion as described herein. In contrast to the formulation of the first aspect, in this formulation, the propellant is not defined as integral component of the formulation. Instead, the formulation is defined as such, and the propellant is provided to pressurize the formulation, thereby providing a pressurized formulation. In preferred embodiments, the formulation of this aspect comprises essentially no fatty alcohol, preferably essentially no foam adjuvant. The optional gelling agent (b) is a gelling agent as described herein. The propellant, provided to pressurize the container is a propellant, as described herein.

The pressurized formulation may be used in medicine. The medical use may be any medical use as described herein, in particular the treatment and/or prevention of a dermatological disease or condition in a subject, as described herein.

Another aspect of the present invention relates to a formulation that is defined as the formulation of the first aspect of the invention but may comprise a fatty alcohol or another foam adjuvant.

A second aspect of the invention relates to a method for stabilizing of a nanoemulsion, comprising the following steps: (a) providing a nanoemulsion comprising: (i) at least one aqueous component; (ii) a carrier component comprising: (1) at least one lipophilic component, (2) at least one surfactant, and (3) at least one alcohol; (b) introducing the nanoemulsion into a container; and (c) adding a propellant to the container to pressurize the container.

This aspect is based on the surprising finding that the stability of a nanoemulsion can be significantly increased when the nanoemulsion is stored together with a propellant in a pressurized container, compared to storage in another vessel, such as a glass vial. The overall increase in stability does not depend on the presence of a gelling agent. The increase in stability is particularly striking at stressed conditions, such as storage at elevated temperatures.

The skilled person is aware of suitable methods to fill the nanoemulsion or the formulation comprising the nanoemulsion and the propellant a container to obtain a pressurized container comprising the nanoemulsion or the formulation comprising the nanoemulsion and the propellant. In preferred embodiments, the propellant is added to the container comprising the nanoemulsion or the formulation comprising the nanoemulsion via a valve.

The method also provides for stabilizing of a nanoemulsion formulation, i.e. a formulation comprising a nanoemulsion and further an active agent and/or an additional aqueous component such as water, a buffer or a gelling agent. Thus, in some embodiments, the method of the second aspect is a method for stabilizing of a formulation comprising a nanoemulsion. In embodiments where the nanoemulsion formulation comprises an active agent, the active agent is also stabilized, i.e. the concentration of the active agent remains stable, even under stressed conditions.

In this second aspect, the nanoemulsion is a nanoemulsion as defined with respect to the first aspect. In this second aspect, the formulation comprising the nanoemulsion corresponds to the formulation as defined with respect to the first aspect, with the difference that the formulation does not comprise a propellant (the propellant is provided in step (c)), and that the formulation comprising the nanoemulsion may comprise a fatty alcohol or another foam adjuvant. In preferred embodiments, the formulation comprising the nanoemulsion comprises essentially no fatty alcohol, preferably essentially no foam adjuvant. In preferred embodiments, the formulation comprising the nanoemulsion comprises essentially no gelling agent.

In preferred embodiments, the nanovesicles comprised in the nanoemulsion have a stable size of less than or equal to 500 nm, preferably in the range of 5 nm to 200 nm, when stored one month, two months, three months, or at least one month, at least two months, or at least three months at 4-40° C., at 10-40° C., at 20-40° C., at 30-40° C., or at 40° C. in the pressurized container. Preferably, the size is determined by dynamic light scattering.

In preferred embodiments, the nanoemulsion is characterized by a stable polydispersity index of less than or equal to 0.4 and/or 0.3, when stored one month, two months, three months, or at least one month, at least two months, or at least three months at 4-40° C., at 10-40° C., at 20-40° C., at 30-40° C., or at 40° C. in the pressurized container. Preferably, the polydispersity index is determined by dynamic light scattering.

A third aspect of the invention relates to a use of a nanoemulsion for the preparation of a foam, comprising the following steps: (a) providing a formulation comprising a nanoemulsion, the nanoemulsion comprising: (i) at least one aqueous component; (ii) a carrier component comprising: (1) at least one lipophilic component, (2) at least one surfactant, and (3) at least one alcohol; (b) introducing the formulation comprising the nanoemulsion into a container; (c) adding a propellant to the container to pressurize the container; and (d) releasing a foam from the pressurized container. The foam comprises the nanoemulsion.

This third aspect is based on the surprising finding that a stable foam can be prepared from a formulation comprising a nanoemulsion that is comprised in a pressurized container, even in the absence of a fatty alcohol or another foam adjuvant.

The foam is characterized by a high stability and a long collapse time. For example, the collapse time is at least 8 minutes, at least 9 minutes or at least 10 minutes at temperatures below 40° C., e.g. at 25° C. or 36° C.

In addition, this third aspect is based on the surprising finding that the stability of a nanoemulsion can be significantly increased when the nanoemulsion is stored together with a propellant in a pressurized container, compared to storage in another vessel, such as a glass vial, even in the absence of a fatty alcohol or another foam adjuvant.

In embodiments where the nanoemulsion formulation comprises an active agent, the active agent is also stabilized, i.e. the concentration of the active agent remains stable, even under stressed conditions.

In this third aspect, the nanoemulsion is a nanoemulsion as defined with respect to the first aspect. In this third aspect, the formulation comprising the nanoemulsion corresponds to the formulation as defined with respect to the first aspect, with the difference that the formulation does not comprise a propellant (the propellant is provided in step (c)), and that the formulation comprising the nanoemulsion may comprise a fatty alcohol or another foam adjuvant. In preferred embodiments, the formulation comprising the nanoemulsion comprises essentially no fatty alcohol, preferably essentially no foam adjuvant. In preferred embodiments, the formulation comprising the nanoemulsion comprises essentially no gelling agent.

Yet another aspect of the present invention is a method for the preparation the formulation of first aspect of the present invention, comprising the following steps:
(a) mixing the at least one lipophilic component, the at least one surfactant, and the at least one alcohol,
(b) contacting the mixture obtained in step (a) with an aqueous component, under conditions allowing formation of a nanoemulsion,
(c) introducing the formulation obtained in steps (c) into container, and
(d) adding a propellant to the container to pressurize the container.

The method may comprise a step of adding an active agent.

In step (b), the conditions allowing formation of the nanoemulsion may include mixing both phases at an appropriate temperature and stirring in a fashion to form nanovesicle. The skilled knows suitable temperature and stirring conditions. A vesicle size of less than or equal to 500 nm or less than or equal to 300 nm, preferably in the range of 5 nm to 200 nm, more preferably in the range of 5 nm to 100 nm can be obtained. In particular, the preparation of the nanoemulsion of the present invention according to step (b) can be prepared without the use of high energy methods, which are well known in the art. High energy method includes high-pressure homogenization, microfluidization, and ultrasonication (Prev Nutr Food Sci. 2019 September; 24 (3): 225-234).

In some embodiments, the container is comprised in a dispenser, such as a foam dispenser or spray dispenser, preferably a foam dispenser. In other words, the container may be part of a dispenser.

The dispenser may be any suitable dispenser. Examples of a foam dispenser and a spray dispenser are shown in FIG. 1. Suitable dispensers are known to the skilled person. The container may be any suitable container, capable of being pressurized. Suitable containers are known to the skilled person.

The active agent may be added in step (a), or may be added to the aqueous component before contacting the mixture obtained in step (a) with an aqueous component in step (b), or may be added to the nanoemulsion obtained in step (b).

The conditions allowing interactions of the active agent with the surface of the nanovesicles when dissolved in the aqueous phase, and/or dissolving the active agent in the lipid core of the nanovesicles may depend upon the hydrophilicity or lipophilicity of the active agent.

A hydrophilic compound, such as an amino acid, preferably a photosensitizer or a metabolic precursor, such as ALA, or/and a pharmaceutically acceptable salt thereof (such as ALA hydrochloride) or acceptable derivative (such as Methyl-ALA), can be added to the aqueous component before contacting the mixture obtained in step (a) with an aqueous component in step (b), such that the active agent is dissolved in the aqueous phase, and capable to interact with the nanovesicles (in particular to the nanovesicle surface) in step (b).

A hydrophilic compound, such as an amino acid, preferably a photosensitizer or a metabolic precursor, such as ALA, or/and a pharmaceutically acceptable salt thereof (such as ALA hydrochloride) or acceptable derivative (such as Methyl-ALA), can also be added to the nanoemulsion obtained in step (b), such that the active agent is dissolved in the aqueous phase, and capable to interact with the nanovesicles (in particular to the nanovesicle surface).

A lipophilic compound, such as a pharmaceutically acceptable macrolide lactone, preferably a calcineurin inhibitor, such as tacrolimus, or/and a pharmaceutically acceptable derivative, can be added in step (a), such that the active agent is dissolved in the lipid core of the nanovesicles.

The method for the preparation the formulation of the present invention can further comprise:
(i) adding a gelling agent, and/or
(ii) adding a preservative.

A fourth aspect of the invention relates to a container or a dispenser product comprising a container, comprising a formulation, wherein said formulation comprises a nanoemulsion comprising (i) at least one aqueous component; (ii) a carrier component comprising (1) at least one lipophilic component, (2) at least one surfactant, and (3) at least one alcohol; and (b) a propellant, wherein the formulation comprises essentially no emollient, essentially no fatty alcohol, preferably essentially no foam adjuvant and/or essentially no gelling agent; and wherein the container further comprises a propellant, wherein the propellant is provided to pressurize the container.

In preferred embodiments, the dispenser product is a foam dispenser or a spray dispenser, preferably a foam dispenser. The dispenser product comprises a container, containing the formulation and a pressurized propellant, and a foam-generating device mounted on the container. Said foam-generating device can comprise a valve for releasing and dosing of the formulation, and a push button for actuating the valve. Upon actuating the push button, the formulation can be released and can form a foam. Examples of dispensers are shown in FIG. 1. Suitable dispensers are known to the skilled person.

A fifth aspect of the invention relates to a foam obtained from the formulation of the first aspect. The foam, comprises the formulation as described herein. The foam is formed upon release of the formulation from a suitable pressurized device, for example from the foam dispenser product as described herein.

Surprisingly, the inventors found that the nanoemulsion foam, obtained from the formulation of the invention, has a collapse time of at least 10 min at room temperature without any foaming agents, after the formulation comprised in a pressurized container was subjected to stressed conditions, such as freeze-thaw cycles or storing under elevated temperatures (40° C.). As used herein, the collapse time is the time for the foam to collapse to half of its initial foamed volume upon release. The nanoemulsion foam described in the present invention does not need any foaming agent to form a stable foam upon release but breaks under sheer force. Furthermore, it was discovered that with higher lipophilic content (e.g., 20% lipid content example), the foam described in the present invention, has a collapse time of at least 8 min at 36° C. (skin temperature). It is preferred that the formulation of the invention has a collapse time which is at least 8 minutes or at least 10 minutes at room temperature, for example 20-25° C.

A sixth aspect of the invention relates to a cosmetic use of the formulation of the first aspect or the foam of the fifth aspect.

In this aspect, the formulation comprises a cosmetic agent as described herein. A seventh aspect of the invention relates to the formulation of the first aspect or the foam of the fifth aspect for use in medicine.

In preferred embodiments, the formulation or foam is provided for use in a method of treatment and/or prevention of a dermatological disease or condition in a subject.

Treatment and/or prevention of the dermatological disease or condition may comprise:
(a) topically administering to the subject, a pharmaceutically effective amount of the formulation comprising a pharmaceutically acceptable macrolide lactone, preferably a calcineurin inhibitor, such as tacrolimus, a derivative, precursor, analog and/or metabolite thereof, as described herein, to a diseased or affected area and an area surrounding the diseased or affected area of the skin, wherein the formulation forms a foam, and,
(b) optionally incubating the pharmaceutically formulation on the skin of the subject with or without occlusion of the area of the skin to which the formulation was administered, the occlusion preferably performed using low density polyethylene or polyurethane film, to enhance deep layer tissue penetration.

The treatment and/or prevention of the dermatological disease or condition may also comprise:
(a) topically administering to the subject, a pharmaceutically effective amount of the formulation comprising a photosensitizer or a metabolic precursor thereof, preferably 5-aminolevulinic acid, a pharmaceutically acceptable salt, a derivative, precursor and/or metabolite thereof, as described herein, to a diseased or affected area and optionally an area surrounding the diseased or affected area of the skin, wherein the formulation forms a foam, and
(b) optionally incubating the pharmaceutically formulation on the skin of the subject with or without occlusion of the area of the skin to which the formulation was administered, the occlusion preferably performed using low density polyethylene or polyurethane film, to enhance deep layer tissue penetration.

The treatment and/or prevention of the dermatological disease or condition may also comprise:
(a) topically administering to the subject, a pharmaceutically effective amount of the formulation comprising a photosensitizer or a metabolic precursor thereof, preferably 5-aminolevulinic acid, a pharmaceutically acceptable salt, a derivative, precursor and/or metabolite thereof, as described herein, to a diseased or affected area and optionally an area surrounding the diseased or affected area of the skin, wherein the formulation forms a foam, and (b) optionally incubating the pharmaceutically formulation on the skin of the subject with or without occlusion of the area of the skin to which the formulation was administered, the occlusion preferably performed using low density polyethylene or polyurethane film, to enhance deep layer tissue penetration, and (c) irradiating the skin area to which the formulation was administered, with light.

The light spectrum used for irradiation in step (c) may match the absorption spectrum of a fluorescent porphyrin. For example, the light spectrum may match the absorption peaks of protoporphyrin IX. In particular, the light used for irradiation in step (c) may comprise any visible wavelength in the range of 380 nm to 780 nm, preferably with equal irradiance throughout or irradiance peak(s) at around 410 and/or 505 and/or 542 and/or 575 and/or 635 nm. The wavelength spectrum may be essentially free of radiation with a wavelength of less than 380 nm and/or larger than 780 nm. In particular, the light used for irradiation in step (c) may comprise any visible wavelength in the range of 380-440 nm and/or 580-650 nm. The light used for irradiation in step (c) may further be capable to induce red fluorescence of accumulated porphyrins.

The light used in step (c) may be red light, blue light, green light and/or violet light, preferably red light and/or violet light, more preferably wherein (a) the red light results in a radiant exposure of 10-75 $J/cm^2$, preferably of 25-45 $J/cm^2$; and/or the violet light results in a radiant exposure of 1-30 $J/cm^2$, preferably 5 to 15 $J/cm^2$.

Irradiation in step (c) may be performed with artificial light, sunlight and/or daylight or with an artificial light source emitting light with a wavelength spectrum and preferably also irradiance similar or identical to sun light. The light with a wavelength spectrum and preferably also irradiance similar or identical to sun light may have a wavelength spectrum of 100 nm to 1000 nm, a wavelength spectrum of 380 nm to 780 nm, preferably with equal irradiance throughout or irradiance peak(s) at around 410 and/or 505 and/or 635 nm, or a wavelength spectrum of 570 nm to 650 nm or 570 nm to 630 nm, and/or a wavelength spectrum of 380 nm to 440 nm. Artificial light may be provided by an LED. A suitable device providing artificial light is described, for example, in U.S. Pat. No. 11,235,169 B1 and U.S. Pat. No. 11,219,781 B2, the disclosure of which is incorporated herein by reference.

The area surrounding the diseased or affected area of the skin may include a surrounding area not affected, to ensure that the diseased or affected area is adequately treated in the peripheral diseased or affected areas. For example, the area surrounding the diseased or affected area of the skin may include an area of at least about 5 mm width.

The dermatological disease or condition to be treated with the pharmaceutical formulation as described herein, may include, but is not limited to, diseases or conditions of the skin, skin appendages or mucosa.

The dermatological disease or condition to be treated with the pharmaceutical formulation as described herein, may be selected from the group consisting of inflammatory, neoplastic, proliferative, infectious, and/or autoimmune diseases or conditions, and/or the cutaneous manifestation thereof, and/or diseases associated with single lesions or fields of lesions, neoplastic, proliferative and/or inflammatory changes.

The inflammatory dermatological disease or condition to be treated with the pharmaceutical formulation as described herein, may be selected from the group consisting of dermatitis, contact dermatitis, acne, atopic dermatitis, eczema, pustular dermatitis, seborrheic dermatitis, perioral dermatitis, chronic wound, urticaria, skin ulcer, rosacea, rash, drug eruptions, toxic epidermal necrolysis; erythema multiforme, erythema nodosum, granuloma annulare, and other cutaneous manifestations of inflammation.

The neoplastic and/or proliferative dermatological disease or condition to be treated with the pharmaceutical formulation as described herein, may be selected from the group consisting of basal cell carcinoma, preferably superficial basal cell carcinoma or nodular basal cell carcinoma; squamous cell carcinoma, preferably Morbus Bowen or invasive squamous cell carcinoma; vulvar intraepithelial neoplasia (VIN); cutaneous T-cell lymphoma; Merkel cell carcinoma; hemangioma; a nodular or subcutaneous cancer disease; field cancerization; non-melanoma skin cancer in organ transplant recipients; and prevention of non-melanoma skin cancer in organ transplant recipients.

The infectious dermatological disease or condition to be treated with the pharmaceutical formulation as described herein, may be selected from the group consisting of bacterial infections, viral infections, fungal infections, parasitic infections, and combinations thereof.

The autoimmune dermatological disease or condition, or the cutaneous manifestation of the autoimmune condition to be treated with the pharmaceutical formulation as described herein, may be selected from the group consisting of psoriasis, pemphigus, systemic lupus erythematodes, lichen planus, morphea, sclerodermia, epidermolysis bullosa, dermatomyositis, graft-versus-host syndrome.

The dermatological disease or condition to be treated with the pharmaceutical formulation as described herein, may be selected from the group consisting of disorders of sweating, pigmentation disorders including hypopigmentation such as vitiligo, albinism and post inflammatory hypopigmentation and hyperpigmentation such as melasma, reactions to sunlight, such as sunburn, skin ageing, photosensitivity, disorders of hair follicles and sebaceous glands such as hypertrichosis, alopecia, male pattern baldness.

The formulation as described herein, in particular a pharmaceutical composition comprising a photosensitizer or a metabolic precursor thereof, preferably 5-aminolevulinic acid, a pharmaceutically acceptable salt, a derivative, precursor and/or metabolite thereof, as described herein, may be used in a method of photodynamic diagnosis of a neoplastic and/or proliferative dermatological disease or condition, such as benign or malignant neoplasia or precursors thereof; an inflammatory dermatological disease or condition; and/or a condition associated with bacterial proliferation such as acne.

The formulation as described herein, in particular a pharmaceutical composition comprising (a) a photosensitizer or a metabolic precursor thereof, preferably 5-aminolevulinic acid, a pharmaceutically acceptable salt, a derivative, precursor and/or metabolite thereof, or (b) a pharmaceutically acceptable macrolide lactone, preferably a calcineurin inhibitor, such as tacrolimus, a derivative, precursor and/or metabolite thereof, may be used in the treatment of a disease or condition as described herein, for example, neoplastic and/or proliferative dermatological diseases or conditions, such as benign or malignant skin neoplasia or precursors thereof, inflammatory dermatological diseases or conditions such as atopic dermatitis, eczema, psoriasis, rosacea or chronic wounds, and conditions associated with bacterial proliferation such as acne.

Yet another aspect of the present invention is the use of the formulation of the present invention, as described herein, for the manufacture of a medicament for the treatment and/or prevention of a dermatological disease or condition in a subject. In particular, the dermatological disease is a dermatological disease or condition as described herein.

Yet another aspect of the present invention is a method of treatment and/or prevention of a dermatological disease or condition in a subject, said method comprising administering to the subject, a pharmaceutically effective amount of the formulation as described herein. In particular, the dermatological disease is a dermatological disease or condition as described herein.

Yet another aspect of the present invention is a method of photodynamic diagnosis of a neoplastic and/or proliferative dermatological disease or condition, such as benign or malignant neoplasia or precursors thereof; an inflammatory dermatological disease or condition; and/or a condition associated with bacterial proliferation such as acne.

ALA (and derivatives) containing drugs drive the synthesis of fluorescent porphyrins that accumulate preferentially in cells/tissues with increased metabolic activity. This can be exploited in the method of photodynamic diagnostics, which can be applied to neoplastic diseases of the skin, such as benign or malignant neoplasia or precursors thereof, inflammatory conditions or conditions associated with bacterial proliferation such as acne. For photodynamic diagnosis, a ALA (or derivative) containing formulation is applied to the skin area to be diagnosed and incubated for an appropriate time. Subsequently, blue spectrum light is applied to induce red fluorescence of accumulated porphyrins. The fluorescence can be detected by visual inspection or appropriate technical devices for qualitative or quantitative assessment.

The method of photodynamic diagnosis may comprise:
  (i) administering the formulation comprising, a photosensitizer or a metabolic precursor thereof, preferably 5-aminolevulinic acid, a pharmaceutically acceptable salt, a derivative, precursor and/or metabolite thereof, as described herein to the skin area to be diagnosed, under conditions allowing synthesis of fluorescent porphyrins in the cells and/or tissues, and
  (ii) irradiating the skin area to which the formulation was administered, under conditions inducing fluorescence of accumulated porphyrins, wherein increased fluorescence of porphyrins indicates increased metabolic activity, being indicative for a neoplastic and/or proliferative dermatological disease or condition, an inflammatory dermatological disease or condition; and/or a condition associated with bacterial proliferation.

In step (i), a photosensitizer or a metabolic precursor thereof, preferably 5-aminolevulinic acid, a pharmaceutically acceptable salt, a derivative, precursor and/or metabolite thereof may be incubated on the skin for an appropriate duration.

In step (ii), the skin can be irradiated with light capable to induce red fluorescence of accumulated porphyrins. Suitable irradiation conditions are described herein.

Diagnosis of the neoplastic and/or proliferative dermatological disease or condition, can be performed by detection of increased fluorescence (e.g., compared with healthy tissue and/or skin, e.g., adjacent to the suspected area). Detection of fluorescence can be performed by visual inspection or appropriate technical devices for qualitative or quantitative assessment.

Diagnosis according to the method described herein may be performed for demarcation of tumor borders to assist surgery, to assess treatment efficacy, and/or the assessment of light induced photobleaching for light dosimetry in photodynamic therapy.

Yet another aspect of the present invention is a method of cosmetic treatment and/or prevention of a dermatological condition in a subject, said method comprising administering to the subject, an effective amount of the formulation as described herein. In particular, the cosmetic treatment and/or prevention may include to moisturize skin, clean the skin, protect the skin from sun (UV rays) or other external influences, help maintain skin barrier function, beautify the skin, reduce signs of skin ageing, and as supportive care for stressed skin or diseased skin.

The invention also pertains to the following embodiments:
  1. A formulation comprising:
    (a) a nanoemulsion comprising:
      (i) at least one aqueous component;
      (ii) a carrier component comprising:
        (1) at least one lipophilic component,
        (2) at least one surfactant, and
        (3) at least one alcohol; and
    (b) a propellant,
    wherein the formulation is comprised in a pressurized container, and wherein the formulation comprises essentially no fatty alcohol.
  2. The formulation of embodiment 1, wherein the formulation comprises essentially no fatty acid.
  3. The formulation of embodiment 1 or 2, preferably 2, wherein the formulation comprises essentially no gelling agent.
  4. The formulation of any one of embodiments 1 to 3, preferably 3, wherein the formulation comprises essentially no emollient selected from a monoester or diester comprising an alcohol and a fatty acid.
  5. The formulation of any one of embodiments 1 or 2, preferably 2, wherein the formulation comprises a gelling agent, wherein the gelling agent is present in an amount of 0.1% to 10% (w/w) based on the total weight of the formulation.
  6. The formulation of embodiment 5, wherein the gelling agent is a poloxamer, wherein the poloxamer is present in an amount of 0.5% to 4% (w/w) based on the total weight of the formulation.
  7. The formulation of embodiment 6, wherein the at least one lipophilic component is present in an amount of 10% to 30% (w/w), preferably 15% to 30% (w/w), and more preferably 20% to 30% (w/w) based on the total weight of the nanoemulsion (a).
  8. The formulation of any one of embodiments 1 to 7, wherein the nanoemulsion
    a. comprises nanovesicles having a size of less than or equal to 500 nm, preferably in the range of 5 nm to 200 nm, when stored one month, two months, three months, six months, or twelve months at 2-40° C., at 10-40° C., at 20-40° C., at 30-40° C., or at 40° C. in the pressurized container; and/or
    b. is characterized by a polydispersity index of less than or equal to 0.4, when stored one month, two months, three months, six months, or twelve months, at 2-40° C., at 10-40° C., at 20-40° C., at 30-40° C., or at 40° C. in the pressurized container; and/or
    c. comprises nanovesicles having a size of less than or equal to 500 nm, preferably in the range of 5 nm to 200 nm, when stored one month, two months, three months, six months, twelve months, eighteen months, or twenty-four months at 2-25° C., at 10-25° C., at 15-25° C., at 2-8° C., at 5° C. or at 25° C. in the pressurized container; and/or d. comprises nanovesicles having a size of less than or equal to 500 nm, preferably in the range of 5 nm to 200 nm, when subjected to 1, 2, 3, 4, 5 or more freeze-thaw cycles; and/or e. is characterized by a polydispersity index of less than or equal to 0.4, when stored one month, two months, three months, six months, twelve months, eighteen months, or twenty-four months at 2-25° C., at 10-25° C., at 15-25° C., at 2-8° C., at 5° C. or at 25° C. in the pressurized container; and/or f. comprises nanovesicles having a size of less than or equal to 500 nm, preferably in the range of 5 nm to 200 nm, when stored one month, two months, three months, six months, twelve months, eighteen months, twenty-four months, thirty months, or thirty six months at 2-8° C. or at 5° C. in the pressurized container; and/or g. is characterized by a polydispersity index of less than or equal to 0.4, when stored one month, two months, three months, six months, twelve months, eighteen months, twenty-four months, thirty months, or thirty six months, at 2-8° C. or at 5° C. in the pressurized container and/or h. is characterized by a polydispersity index of less than or equal to 0.4, when subjected to 1, 2, 3, 4, 5 or more freeze-thaw cycles.

9. The formulation of any one of embodiments 1 to 8, comprising an active agent.

10. The formulation of embodiment 9, wherein the active agent is 5-aminolevulinic acid, a pharmaceutically acceptable salt, a derivative, precursor and/or metabolite thereof.

11. The formulation of any one of embodiments 1 to 10, wherein
the at least one lipophilic component is selected from triglycerides and mixtures thereof;
the at least one surfactant is selected from the group consisting of a phospholipid, a lysophospholipid, a ceramide and/or a mixture thereof, and/or the at least one surfactant is a polyoxyethylene-type surfactant;
the at least one alcohol has 3-5 carbon atoms; and/or
the propellant is propane, isobutane or n-butane or a mixture thereof.

12. The formulation of any one of embodiments 1 to 11, comprising a total aqueous component in an amount of from 50% to 99% (w/w).

13. The formulation of embodiment 5, wherein the gelling agent is selected from the group consisting of poloxamer, xanthan, bentonite, sodium carboxymethylcellulose, hydroxymethyl cellulose, carbomer, hydroxypropyl cellulose, gellan gum, guar gum, pectin, poly(ethylene)oxide, polycarbophil, alginate, tragacanth, povidone, gelatin, and mixtures thereof.

14. A method for stabilizing a nanoemulsion, comprising the following steps:
(a) providing a nanoemulsion comprising:
  (i) at least one aqueous component;
  (ii) a carrier component comprising:
    (1) at least one lipophilic component,
    (2) at least one surfactant, and
    (3) at least one alcohol;
(b) introducing the nanoemulsion into a container; and
(c) adding a propellant to the container to pressurize the container and/or the nanoemulsion in the container.

15. The method of embodiment 14, wherein the nanoemulsion
a. comprises nanovesicles having a size of less than or equal to 500 nm, preferably in the range of 5 nm to 200 nm, when stored one month, two months, three months, six months, or twelve months at 2-40° C., at 10-40° C., at 20-40° C., at 30-40° C., or at 40° C. in the pressurized container; and/or
b. is characterized by a polydispersity index of less than or equal to 0.4, when stored one month, two months, three months, six months, or twelve months at 2-40° C., at 10-40° C., at 20-40° C., at 30-40° C., or at 40° C. in the pressurized container; and/or
c. comprises nanovesicles having a size of less than or equal to 500 nm, preferably in the range of 5 nm to 200 nm, when stored one month, two months, three months, six months, twelve months, 18 months, or 24 months at 2-25° C., at 10-25° C., at 15-25° C., at 2-8° C., at 5° C. or at 25° C. in the pressurized container; and/or
d. comprises nanovesicles having a size of less than or equal to 500 nm, preferably in the range of 5 nm to 200 nm, when subjected to 1, 2, 3, 4, 5 or more freeze-thaw cycles; and/or
e. is characterized by a polydispersity index of less than or equal to 0.4, when stored one month, two months, three months, six months, twelve months, 18 months, or 24 months at 2-25° C., at 10-25° C., at 15-25° C., at 2-8° C., at 5° C. or at 25° C. in the pressurized container; and/or
f. comprises nanovesicles having a size of less than or equal to 500 nm, preferably in the range of 5 nm to 200 nm, when stored one month, two months, three months, six months, twelve months, eighteen months, twenty-four months, thirty months, or thirty six months at 2-8° C. or at 5° C. in the pressurized container; and/or
g. is characterized by a polydispersity index of less than or equal to 0.4, when stored one month, two months, three months, six months, twelve months, eighteen months, twenty-four months, thirty months, or thirty six months, at 2-8° C. or at 5° C. in the pressurized container and/or
h. is characterized by a polydispersity index of less than or equal to 0.4, when subjected to 1, 2, 3, 4, 5 or more freeze-thaw cycles.

16. Use of a nanoemulsion for the preparation of a foam or a spray, comprising the following steps:
(a) providing a formulation comprising a nanoemulsion comprising:
  (i) at least one aqueous component;
  (ii) a carrier component comprising:
    (1) at least one lipophilic component,
    (2) at least one surfactant, and
    (3) at least one alcohol;
(b) introducing the formulation comprising a nanoemulsion into a container; and
(c) adding a propellant to the container to pressurize the container; and
(d) releasing a foam or a spray from the pressurized container.

17. A container or a foam or spray dispenser product comprising a container, comprising the formulation of any one of embodiments 1 to 13.

18. A foam obtained from the formulation of any one of embodiments 1 to 13.
19. Cosmetic use of the formulation of embodiment any one of embodiments 1 to 13.
20. A method of treating a dermatological disease or condition, comprising administration of an effective amount of the formulation of embodiment 9 to a subject in need thereof.

The invention also pertains to the following items:
1. A formulation comprising:
   (a) a nanoemulsion comprising:
      (i) at least one aqueous component;
      (ii) a carrier component comprising:
         (1) at least one lipophilic component,
         (2) at least one surfactant, and
         (3) at least one alcohol; and
   (b) a propellant,
   wherein the formulation is comprised in a pressurized container, and
   wherein the formulation comprises essentially no fatty alcohol, preferably essentially no fatty alcohol and no fatty acid.
2. The formulation of item 1, wherein the formulation comprises essentially no foam adjuvant.
3. The formulation of any of the preceding items, wherein the formulation comprises essentially no emollient.
4. The formulation of any of the preceding items, wherein formulation comprises essentially no emollient selected from a monoester or diester of an alcohol and a fatty acid.
5. The formulation of any of the preceding items, wherein the formulation comprises essentially no gelling agent.
6. The formulation of any of the preceding items, wherein the nanoemulsion comprises nanovesicles comprising the carrier component.
7. The formulation of item 6, wherein the nanovesicles have a stable size of less than or equal to 500 nm, preferably in the range of 5 nm to 200 nm when stored for one, two, three or at least three months at 40° C. in a pressurized container.
8. The formulation of any of the preceding items, wherein the total aqueous component is present in an amount of 50% to 99% w/w, preferably from 70% to 95% (w/w), and more preferably from 75% to 95% (w/w), based on the total weight of the nanoemulsion (a).
9. The formulation of any one of the preceding items, wherein the aqueous component comprises at least one pH buffering agent, preferably wherein the at least one pH buffering agent is selected from the group consisting of citrate, phosphate, acetate and carbonate.
10. The formulation of any one of the preceding items, wherein at least one lipophilic component is selected from triglycerides and mixtures thereof, preferably wherein the at least one lipophilic component is a caprylic and/or a capric triglyceride or a mixture thereof.
11. The formulation of any one of the preceding items, wherein at least one lipophilic component is present in an amount of from 0.1% to 30% (w/w), preferably from 0.25% to 15% (w/w), preferably from 0.25% to 10% (w/w), and more preferably from 0.5% to 8% (w/w) or 3% to 8% (w/w), based on the total weight of the nanoemulsion (a).
12. The formulation of any one of the preceding items, wherein the at least one surfactant is selected from the group consisting of a phospholipid, a lysophospholipid, a ceramide and/or a mixture thereof, and/or the at least one surfactant is a polyoxyethylene-type surfactant.
13. The formulation of any one of the preceding items, wherein the at least one surfactant is lecithin, preferably soy lecithin, preferably wherein the lecithin has a phosphatidylcholine content of at least 80% by weight.
14. The formulation of item 12, wherein the phospholipid, the lysophospholipid, the ceramide and/or the mixture thereof is present in an amount of from 1% to 10% (w/w), preferably from 1.25% to 5% (w/w), and more preferably from 1.5% to 4% (w/w), based on the total weight of the nanoemulsion (a).
15. The formulation of item 12, wherein the polyoxyethylene-type surfactant is Polysorbate 80.
16. The formulation of any one of items 12 or 15, wherein the polyoxyethylene-type surfactant is present in an amount of from 1% to 10% (w/w), more preferably from 2% to 8% (w/w), and most preferably from 3% to 7% (w/w), based on the total weight of the nanoemulsion (a).
17. The formulation of any one of the preceding items, wherein the at least one alcohol is selected from the group consisting of 1-propanol or 2-propanol and mixtures thereof.
18. The formulation of any one of the preceding items, wherein the alcohol is present in an amount of from 0.1% to 10% w/w, preferably from 0.5% to 5% (w/w), and more preferably from 1% to 3% (w/w), based on the total weight of the nanoemulsion (a).
19. The formulation of any one of the preceding items, wherein the propellant is propane, isobutane or n-butane or a mixture thereof, preferably the propellant is a mixture of propane and isobutane.
20. The formulation of any one of items 1~4 or 6-19, comprising a gelling agent.
21. The formulation of item 20, wherein the gelling agent is selected from the group consisting of poloxamer, xanthan, bentonite, sodium carboxymethylcellulose, hydroxymethyl cellulose, carbomer, hydroxypropyl cellulose, gellan gum, guar gum, pectin, poly(ethylene) oxide, polycarbophil, alginate, tragacanth, povidone, gelatin, and mixtures thereof.
22. The formulation of item 20 or 21, wherein the gelling agent is selected from poloxamer, xanthan and/or mixtures thereof.
23. The formulation of any one of items 20-22, wherein the gelling agent is present in an amount of from 0.1% to 10% w/w, preferably from 0.25% to 5% (w/w), and more preferably from 0.5% to 4% (w/w), based on the total weight of the formulation.
24. The formulation of any one of items 20-23, wherein the nanoemulsion comprises nanovesicles comprising the carrier component, and wherein the nanovesicles have a stable size of less than or equal to 300 nm, preferably in the range of 5 nm to 200 nm, when stored at −15° C. to −25° C., preferably at −24° C., for 4 days in a pressurized container, wherein the size is determined by dynamic light scattering.
25. The formulation of any one of the preceding items, comprising a preservative, preferably wherein the preservative is selected from benzoate, citric acid, EDTA, potassium sorbate, wherein the preservative is preferably sodium benzoate.
26. The formulation of item 23 or 24, wherein the preservative is present in an amount of from 0.01% to 3% w/w, preferably from 0.2% to 2% (w/w) or 0.1-2%

(w/w), and more preferably from 0.2% to 1.5% (w/w), based on the total weight of the formulation.

27. The formulation of any one of the preceding items, which is essentially free of parabens.

28. The formulation of any one of the preceding items, characterized by a polydispersity index of less than or equal to one of the following values 0.4 or 0.3, wherein the polydispersity index is determined by dynamic light scattering.

29. The formulation of any one of the preceding items, wherein the active agent is present in an amount of from 0.001% to 50% w/w, based on the total weight of the formulation.

30. The formulation according to any one of the items 1-29, which is a pharmaceutical formulation comprising an active agent.

31. The formulation of item 30, wherein the active agent is a small organic molecule and has a molecular weight of from 100 to 1000 g/mol, preferably from 115 to 950 g/mol, and more preferably from 130 to 900 g/mol.

32. The formulation of item 30 or 31, wherein the active agent is not a pharmaceutically acceptable macrolide lactone.

33. The formulation of item 32, wherein the active agent is not tacrolimus.

34. The formulation of item 30 or 31, wherein the active agent is a photosensitizer or a metabolic precursor thereof, preferably 5-aminolevulinic acid, a pharmaceutically acceptable salt, a derivative, precursor and/or metabolite thereof.

35. The formulation of item 34, comprising
   (a) a nanoemulsion comprising
      (i) an aqueous component, present in an amount of 70% to 95% w/w, based on the total weight of the nanoemulsion (a);
      (ii) nanovesicles, comprising
         (1) 1-5% of at least one phospholipid, based on the total weight of the nanoemulsion (a);
         (2) 3-7% of at least one polyoxyethylene-type surfactant, based on the total weight of the nanoemulsion (a);
         (3) 1-3% $C_3$ to $C_5$ alcohol, based on the total weight of the nanoemulsion (a); and
         (4) 3-8% triglycerides, based on the total weight of the nanoemulsion (a);
   (b) 1-20% of a photosensitizer or a metabolic precursor thereof, preferably 5-aminolevulinic acid hydrochloride, based on the total weight of the formulation;
   (c) optionally 0.5-4% of at least one gelling agent, based on the total weight of the formulation;
   (d) optionally 0.1-2% of at least one preservative, based on the total weight of the formulation; and
   (e) a propellant.

36. The formulation of any one of the items 1-35, for use in medicine.

37. The formulation of any one of the items 32-35, for use in a method of treatment and/or prevention of a dermatological disease or condition in a subject.

38. The formulation for use of item 37, wherein treatment and/or prevention of the dermatological disease or condition comprises:
   (a) topically administering to the subject, a pharmaceutically effective amount of the formulation of any one of the items 32-35, to a diseased or affected area and area surrounding the diseased or affected area of the skin, wherein the formulation forms a foam, and,
   (b) optionally incubating the pharmaceutically formulation on the skin of the subject with or without occlusion of the area of the skin to which the formulation was administered, the occlusion preferably performed using low density polyethylene or polyurethane film, to enhance deep layer tissue penetration.

39. The formulation of any one of the items 34-35, for use in a method of treatment and/or prevention of a dermatological disease or condition in a subject, wherein the treatment and/or prevention of the dermatological disease or condition comprises:
   (a) topically administering to the subject, a pharmaceutically effective amount of the formulation of any one of the items 33-34, to a diseased or affected area and optionally an area surrounding the diseased or affected area of the skin, wherein the formulation forms a foam, and
   (b) optionally incubating the pharmaceutically formulation on the skin of the subject with or without occlusion of the area of the skin to which the formulation was administered, the occlusion preferably performed using low density polyethylene or polyurethane film, to enhance deep layer tissue penetration, and
   (c) irradiating the skin area to which the formulation was administered, with light.

40. The formulation for use of any one of the items 38-39, wherein the area surrounding the diseased or affected area of the skin includes an area of at least about 5 mm width.

41. The formulation for use of any one of the items 37-40, wherein the dermatological disease or condition includes diseases or conditions of the skin, skin appendages or mucosa.

42. The formulation for use of any one of the items 37-41, wherein the dermatological disease or condition is selected from the group consisting of inflammatory, neoplastic, proliferative, infectious, and/or autoimmune diseases or conditions, and/or the cutaneous manifestation thereof, and/or diseases associated with single lesions or fields of lesions, neoplastic, proliferative and/or inflammatory changes.

43. The formulation for use of item 42, wherein the inflammatory dermatological disease or condition is selected from the group consisting of dermatitis, contact dermatitis, acne, atopic dermatitis, eczema, pustular dermatitis, seborrheic dermatitis, perioral dermatitis, chronic wound, urticaria, skin ulcer, rosacea, rash, drug eruptions, toxic epidermal necrolysis; erythema multiforme, erythema nodosum, granuloma annulare, and other cutaneous manifestations of inflammation.

44. The formulation for use of item 42, wherein the neoplastic and/or proliferative dermatological disease or condition is selected from the group consisting of basal cell carcinoma, preferably superficial basal cell carcinoma or nodular basal cell carcinoma; squamous cell carcinoma, preferably Morbus Bowen or invasive squamous cell carcinoma; vulvar intraepithelial neoplasia (VIN); cutaneous T-cell lymphoma; Merkel cell carcinoma; hemangioma; a nodular or subcutaneous cancer disease; field cancerization; non-melanoma skin cancer in organ transplant recipients; and prevention of non-melanoma skin cancer in organ transplant recipients.

45. The formulation for use of item 42, wherein the infectious dermatological disease or condition is selected from the group consisting of bacterial infections, viral infections, fungal infections, parasitic infections, and combinations thereof.

46. The formulation for use of item 42, wherein the autoimmune dermatological disease or condition, or the cutaneous manifestation of the autoimmune condition is selected from the group consisting of psoriasis, pemphigus, systemic lupus erythematodes, lichen planus, morphea, sclerodermia, epidermolysis bullosa, dermatomyositis, graft-versus-host syndrome.

47. The formulation for use of any one of the items 37-46, wherein the dermatological disease or condition is selected from the group consisting of disorders of sweating, pigmentation disorders including hypopigmentation such as vitiligo, albinism and post inflammatory hypopigmentation and hyperpigmentation such as melasma, reactions to sunlight, such as sunburn, skin ageing, photosensitivity, disorders of hair follicles and sebaceous glands such as hypertrichosis, alopecia, male pattern baldness.

48. The formulation of any one of the items 34-35, for use in a method of photodynamic diagnosis of a neoplastic and/or proliferative dermatological disease or condition, such as benign or malignant neoplasia or precursors thereof; an inflammatory dermatological disease or condition; and/or a condition associated with bacterial proliferation such as acne.

49. The formulation according to any one of the items 1-29, which is a cosmetic formulation.

50. The formulation of item 49, wherein the active agent is a cosmetic active agent selected from plant extracts, natural or synthetic moisturizers, natural or synthetic cleaning agents, natural or synthetic protective agents, natural or synthetic detergents, natural or synthetic antioxidants, natural or synthetic skin conditioning agents and natural or synthetic vitamins.

51. Use of the formulation of item 49 or 50 to moisturize skin, clean skin, protect from sun (UV rays) or other external influences, help maintain skin barrier function, beautify skin, reduce signs of skin aging, or as supportive care for stressed skin or diseased skin.

52. A method for the preparation the formulation of any one of the items 1-50, comprising the following steps:
    (a) mixing the at least one lipophilic component, the at least one surfactant, and the at least one alcohol having at least three carbon atoms,
    (b) contacting the mixture obtained in step (a) with an aqueous component, under conditions allowing formation of a nanoemulsion,
    (c) introducing the formulation obtained in steps (c) into a dispenser or container, and
    (d) adding a propellant to the dispenser or container to pressurize the dispenser or container.

53. The method of item 52, further comprising
    (i) adding an active agent;
    (ii) adding a gelling agent, and/or
    (iii) adding a preservative.

54. A container comprising a formulation, wherein said formulation comprises a nanoemulsion comprising:
    (i) at least one aqueous component;
    (ii) a carrier component comprising:
        (1) at least one lipophilic component,
        (2) at least one surfactant, and
        (3) at least one alcohol;
    wherein the formulation comprises essentially no emollient; and
    wherein the container further comprises a propellant, wherein the propellant is provided to pressurize the container.

55. A dispenser product comprising a container, comprising a formulation, wherein said formulation comprises a nanoemulsion comprising:
    (i) at least one aqueous component;
    (ii) a carrier component comprising:
        (1) at least one lipophilic component,
        (2) at least one surfactant, and
        (3) at least one alcohol;
    wherein the formulation comprises essentially no foam adjuvant; and
    wherein the container further comprises a propellant, wherein the propellant is provided to pressurize the container.

56. The container of item 54 or the dispenser product of item 55, wherein the formulation and the propellant are independently as defined in any one of items 1-50.

57. A formulation, said formulation comprising
    (a) a nanoemulsion comprising:
        (i) at least one aqueous component;
        (ii) a carrier component comprising:
            (1) at least one lipophilic component,
            (2) at least one surfactant, and
            (3) at least one alcohol having at least three carbon atoms,
        (iii) optionally an active agent
    (b) optionally a gelling agent,
    wherein the formulation is provided in a container further comprising a propellant, wherein the propellant is provided to pressurize the container.

58. A formulation, said formulation comprising
    (a) a nanoemulsion comprising:
        (i) at least one aqueous component;
        (ii) a carrier component comprising:
            (1) at least one lipophilic component,
            (2) at least one surfactant, and
            (3) at least one alcohol having at least three carbon atoms,
        (iii) optionally an active agent
    (b) optionally a gelling agent,
    wherein the formulation is prepared as a pressurized formulation, wherein a propellant is provided to pressurize the formulation.

59. The formulation of item 57 or 58, wherein the constituents of the formulation, in particular the nanoemulsion, the gelling agent and the propellant are independently as defined in any one of items 1-50.

60. The formulation of any one of items 57-59, for use in medicine.

61. The formulation of any one of items 57-59, for use in a method of treatment and/or prevention of a dermatological disease or condition in a subject.

62. A foam, obtained from or comprising the formulation of any one of items 1-50, or 57-61.

63. Cosmetic use of the formulation according to any one of the items 1-29, 57, 58 and 59.

64. Use of the formulation according to any one of the items 1-48, 57, 58 and 59, for the manufacture of a medicament for the treatment and/or prevention of a dermatological disease or condition in a subject.

65. Method of treatment and/or prevention of a dermatological disease or condition in a subject, said method comprising administering to the subject, a pharmaceutically effective amount of the formulation of any one of the items 1-48, 57, 58 and 59.

66. Method of photodynamic diagnosis of a neoplastic and/or proliferative dermatological disease or condition, such as benign or malignant neoplasia or precursors thereof; an inflammatory dermatological disease or condition; and/or a condition associated with bacterial proliferation such as acne, said method comprising
   (i) administering the formulation according to item 34 or 35 to the skin area to be diagnosed, under conditions allowing synthesis of fluorescent porphyrins in the cells and/or tissues, and
   (ii) irradiating the skin area to which the formulation was administered, under conditions inducing fluorescence of accumulated porphyrins,
   wherein increased fluorescence of porphyrins indicates increased metabolic activity, being indicative for a neoplastic and/or proliferative dermatological disease or condition, an inflammatory dermatological disease or condition; and/or a condition associated with bacterial proliferation.
67. Method of cosmetic treatment and/or prevention of a dermatological condition in a subject, said method comprising administering to the subject, an effective amount of the formulation of any one of the items 1-29 and 49-51 and 57-59.
68. A method for stabilizing a nanoemulsion, comprising the following steps
   (a) providing a nanoemulsion comprising:
       (i) at least one aqueous component;
       (ii) a carrier component comprising:
           (1) at least one lipophilic component,
           (2) at least one surfactant, and
           (3) at least one alcohol;
   (b) introducing the nanoemulsion into a container; and
   (c) adding a propellant to the container to pressurize the container.
69. The method of item 68, wherein
   the nanoemulsion comprises nanovesicles comprising the carrier component, and wherein the nanovesicles have a stable size of less than or equal to 500 nm, preferably in the range of 5 nm to 200 nm, when stored one month, two months, three months, or at least one month, at least two months, or at least three months at 4-40° C., at 10-40° C., at 20-40° C., at 30-40° C., or at 40° C. in the pressurized container; and/or
   the nanoemulsion is characterized by a stable polydispersity index of less than or equal to 0.4 and/or 0.3, when stored one month, two months, three months, or at least one month, at least two months, or at least three months at 4-40° C., at 10-40° C., at 20-40° C., at 30-40° C., or at 40° C. in the pressurized container.
70. The method of item 68 or 69, wherein the method is for stabilizing a formulation comprising a nanoemulsion.
71. The method of item 70, wherein the formulation, the nanoemulsion and the propellant are independently as defined in any one of items 1-50.
72. Use of a nanoemulsion for the preparation of a foam or a spray, comprising the following steps:
   (a) providing a formulation comprising a nanoemulsion comprising:
       (i) at least one aqueous component;
       (ii) a carrier component comprising:
           (1) at least one lipophilic component,
           (2) at least one surfactant, and
           (3) at least one alcohol;
   (b) introducing the formulation comprising a nanoemulsion into a container; and
   (c) adding a propellant to the container to pressurize the container; and
   (d) releasing a foam or a spray from the pressurized container.
73. The use of item 72, wherein the formulation comprising the nanoemulsion, the nanoemulsion and the propellant are independently as defined in any one of items 1-50.

The invention also pertains to the following items:
1. A formulation comprising:
   (a) a nanoemulsion comprising:
       (i) at least one aqueous component;
       (ii) a carrier component comprising:
           (1) at least one lipophilic component,
           (2) at least one surfactant, and
           (3) at least one alcohol; and
   (b) a propellant,
   wherein the formulation is comprised in a pressurized container, and
   wherein the formulation comprises essentially no fatty alcohol.
2. The formulation of item 1, wherein the formulation comprises essentially no emollient selected from a monoester or diester comprising an alcohol and a fatty acid.
3. The formulation of item 1 or 2, wherein the formulation comprises essentially no gelling agent.
4. The formulation of any one of the preceding items, wherein the at least one lipophilic component is selected from triglycerides and mixtures thereof, preferably wherein the at least one lipophilic component is a caprylic and/or a capric triglyceride or a mixture thereof.
5. The formulation of any one of the preceding items, wherein the at least one surfactant is selected from the group consisting of a phospholipid, a lysophospholipid, a ceramide and/or a mixture thereof, and/or the at least one surfactant is a polyoxyethylene-type surfactant.
6. The formulation of any one of the preceding items, wherein the at least one alcohol has 3-5 carbon atoms, more preferably the at least one alcohol is selected from the group consisting of 1-propanol and 2-propanol and mixtures thereof.
7. The formulation of any one of the preceding items, wherein the propellant is propane, isobutane or n-butane or a mixture thereof.
8. The formulation of any one of the preceding items, comprising a total aqueous component in an amount of from 50% to 99% (w/w), preferably from 70% to 95% (w/w), more preferably from 75% to 95% (w/w), even more preferably from 80% to 90% (w/w).
9. The formulation of any one of the preceding items, comprising
   (a) the at least one lipophilic component in an amount of from 0.1% to 30% (w/w), preferably from 0.25% to 15% (w/w), preferably from 0.25% to 10% (w/w), and more preferably from 0.5% to 8% (w/w) or 3% to 8% (w/w); and/or
   (b) the at least one alcohol in an amount of from 0.1% to 10% (w/w), preferably from 0.5% to 5% (w/w), and more preferably from 1% to 3% (w/w), based on the total weight of the nanoemulsion (a).

10. The formulation of any one of items 1, 2, or 4 to 9, comprising a gelling agent, preferably wherein the gelling agent is selected from the group consisting of poloxamer, xanthan, bentonite, sodium carboxymethylcellulose, hydroxymethyl cellulose, carbomer, hydroxypropyl cellulose, gellan gum, guar gum, pectin, poly(ethylene)oxide, polycarbophil, alginate, tragacanth, povidone, gelatin, and mixtures thereof, more preferably wherein the gelling agent is selected from poloxamer, xanthan and mixtures thereof, in particular wherein the gelling agent is present in an amount of from 0.1% to 10% (w/w), preferably from 0.25% to 5% (w/w), and more preferably from 0.5% to 4% (w/w), based on the total weight of the formulation.

11. The formulation of item 10, wherein
    the at least one lipophilic component is present in an amount of 10% to 30% (w/w), preferably 15% to 30% (w/w), and more preferably 20% to 30% (w/w) based on the total weight of the nanoemulsion (a), and
    the gelling agent, preferably a poloxamer, is present in an amount of 0.1% to 10% (w/w), preferably 0.25% to 5% (w/w), more preferably 0.5% to 4% (w/w) based on the total weight of the formulation.

12. The formulation of any one of the preceding items, wherein the nanoemulsion
    a. comprises nanovesicles having a size of less than or equal to 500 nm, preferably in the range of 5 nm to 200 nm, when stored one month, two months, three months, six months, or twelve months at 2-40° C., at 10-40° C., at 20-40° C., at 30-40° C., or at 40° C. in the pressurized container; and/or
    b. is characterized by a polydispersity index of less than or equal to 0.4, when stored one month, two months, three months, six months, or twelve months, at 2-40° C., at 10-40° C., at 20-40° C., at 30-40° C., or at 40° C. in the pressurized container; and/or
    c. comprises nanovesicles having a size of less than or equal to 500 nm, preferably in the range of 5 nm to 200 nm, when stored one month, two months, three months, six months, twelve months, eighteen months, or twenty-four months at 2-25° C., at 10-25° C., at 15-25° C., at 2-8° C., at 5° C. or at 25° C. in the pressurized container; and/or
    d. comprises nanovesicles having a size of less than or equal to 500 nm, preferably in the range of 5 nm to 200 nm, when subjected to 1, 2, 3, 4, 5 or more freeze-thaw cycles; and/or
    e. is characterized by a polydispersity index of less than or equal to 0.4, when stored one month, two months, three months, six months, twelve months, eighteen months, or twenty-four months at 2-25° C., at 10-25° C., at 15-25° C., at 2-8° C., at 5° C. or at 25° C. in the pressurized container; and/or
    f. comprises nanovesicles having a size of less than or equal to 500 nm, preferably in the range of 5 nm to 200 nm, when stored one month, two months, three months, six months, twelve months, eighteen months, twenty-four months, thirty months, or thirty six months at 2-8° C. or at 5° C. in the pressurized container; and/or
    g. is characterized by a polydispersity index of less than or equal to 0.4, when stored one month, two months, three months, six months, twelve months, eighteen months, twenty-four months, thirty months, or thirty six months, at 2-8° C. or at 5° C. in the pressurized container; and/or
    h. is characterized by a polydispersity index of less than or equal to 0.4, when subjected to 1, 2, 3, 4, 5 or more freeze-thaw cycles.

13. The formulation of any one of the preceding items, comprising an active agent, preferably a biogenic substance, more preferably
    5-aminolevulinic acid, a pharmaceutically acceptable salt, a derivative, precursor and/or metabolite thereof,
    or diclofenac, a pharmaceutically acceptable salt, a derivative, precursor and/or metabolite thereof.

14. The formulation of any one of the preceding items, comprising 5-aminolevulinic acid, a pharmaceutically acceptable salt, a derivative, precursor and/or metabolite thereof.

15. A method for stabilizing a nanoemulsion, comprising the following steps:
    (a) providing a nanoemulsion comprising:
        (i) at least one aqueous component;
        (ii) a carrier component comprising:
            (1) at least one lipophilic component,
            (2) at least one surfactant, and
            (3) at least one alcohol;
    (b) introducing the nanoemulsion into a container; and
    (c) adding a propellant to the container to pressurize the container and/or the nanoemulsion in the container.

16. The method of item 15, wherein the nanoemulsion is a nanoemulsion formulation comprising an active agent.

17. The method of item 16, wherein the nanoemulsion
    a. comprises nanovesicles having a size of less than or equal to 500 nm, preferably in the range of 5 nm to 200 nm, when stored one month, two months, three months, six months, or twelve months at 2-40° C., at 10-40° C., at 20-40° C., at 30-40° C., or at 40° C. in the pressurized container; and/or
    b. is characterized by a polydispersity index of less than or equal to 0.4, when stored one month, two months, three months, six months, or twelve months at 2-40° C., at 10-40° C., at 20-40° C., at 30-40° C., or at 40° C. in the pressurized container; and/or
    c. comprises nanovesicles having a size of less than or equal to 500 nm, preferably in the range of 5 nm to 200 nm, when stored one month, two months, three months, six months, twelve months, 18 months, or 24 months at 2-25° C., at 10-25° C., at 15-25° C., at 2-8° C., at 5° C. or at 25° C. in the pressurized container; and/or
    d. comprises nanovesicles having a size of less than or equal to 500 nm, preferably in the range of 5 nm to 200 nm, when subjected to 1, 2, 3, 4, 5 or more freeze-thaw cycles; and/or
    e. is characterized by a polydispersity index of less than or equal to 0.4, when stored one month, two months, three months, six months, twelve months, 18 months, or 24 months at 2-25° C., at 10-25° C., at 15-25° C., at 2-8° C., at 5° C. or at 25° C. in the pressurized container; and/or
    f. comprises nanovesicles having a size of less than or equal to 500 nm, preferably in the range of 5 nm to 200 nm, when stored one month, two months, three months, six months, twelve months, eighteen months, twenty-four months, thirty months, or thirty six months at 2-8° C. or at 5° C. in the pressurized container; and/or g. is characterized by a polydispersity index of less than or equal to 0.4, when stored one month, two months, three months, six months, twelve months, eighteen months, twenty-four months, thirty months, or thirty six months, at 2-8° C. or at 5° C. in the pressurized container and/or h. is characterized by a polydispersity index of less than or equal to 0.4, when subjected to 1, 2, 3, 4, 5 or more freeze-thaw cycles.

18. Use of a nanoemulsion for the preparation of a foam or a spray, comprising the following steps:
    (a) providing a formulation comprising a nanoemulsion comprising:
        (i) at least one aqueous component;
        (ii) a carrier component comprising:
            (1) at least one lipophilic component,
            (2) at least one surfactant, and
            (3) at least one alcohol;
    (b) introducing the formulation comprising a nanoemulsion into a container; and
    (c) adding a propellant to the container to pressurize the container; and
    (d) releasing a foam or a spray from the pressurized container.

19. The use of item 18, wherein the formulation comprises an active agent.

20. A container or a foam or spray dispenser product comprising a container, comprising a formulation, wherein said formulation comprises a nanoemulsion comprising:
    (i) at least one aqueous component;
    (ii) a carrier component comprising:
        (1) at least one lipophilic component,
        (2) at least one surfactant, and
        (3) at least one alcohol;
    wherein the formulation comprises essentially no fatty alcohol; and
    wherein the container further comprises a propellant, wherein the propellant is provided to pressurize the container.

21. The container or foam or spray dispenser product of item 20, wherein the formulation comprises an active agent.

22. A foam or spray obtained from the formulation of any one of items 1-14.

23. Cosmetic use of the formulation of any one of the items 1-14 or the foam or spray of item 22.

24. The formulation of item 13 or 14 or the foam or spray of item 22, for use in medicine, preferably for use in a method of treatment and/or prevention of a dermatological disease or condition.

The present invention is further illustrated by the following Figures and Examples.

FIGURE LEGENDS

FIG. 1: Exemplary pressurized dispensers (or containers) with spray head (middle) or foam dispenser valve (left) used in the Examples of the invention for storage of the exemplary formulations. Glass vial used in the Examples of the invention for storage of the exemplary unpressurized comparative formulations (right).

Figure 2:
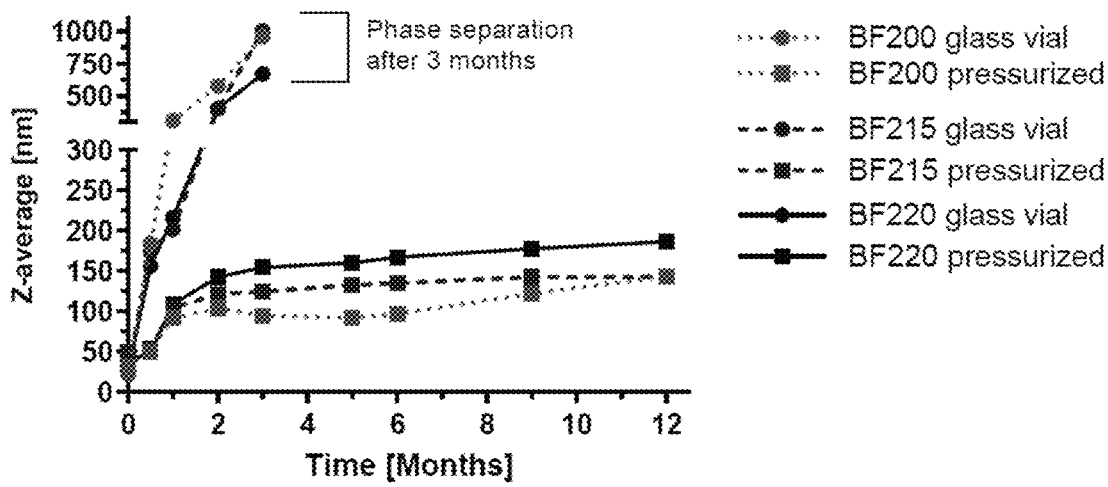
Figure 2:
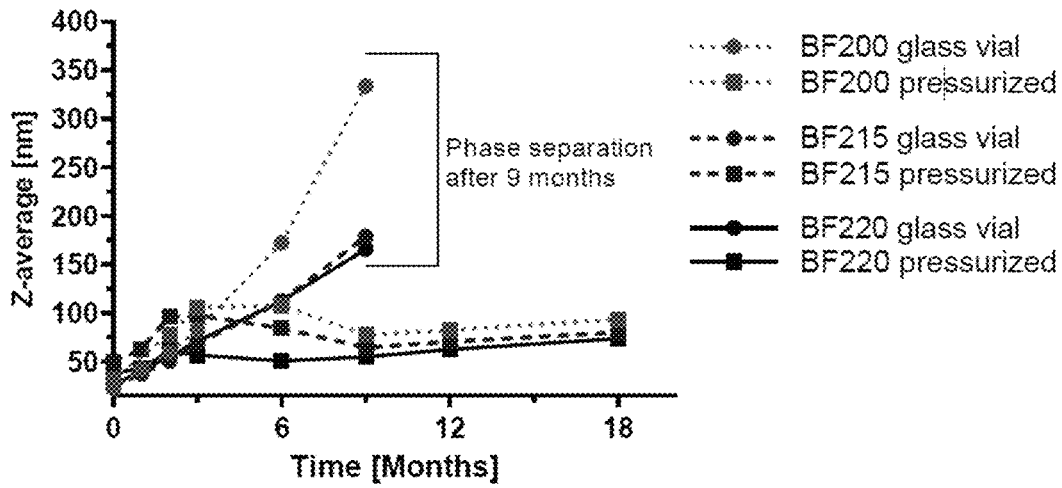

FIG. 2: Comparison of nanoemulsion formulations with different lipophilic contents and without gelling agent: vesicle size over time at different temperatures.

Figure 3:
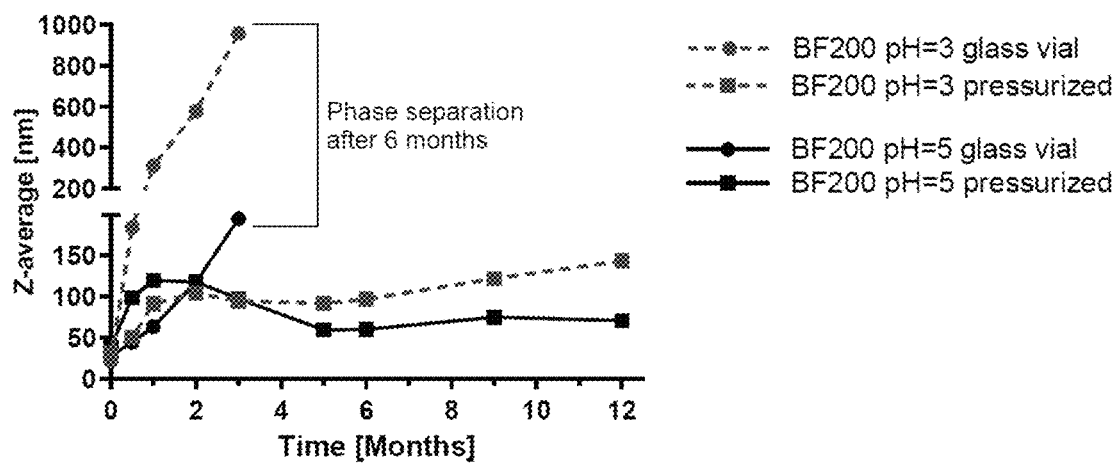
Figure 3:
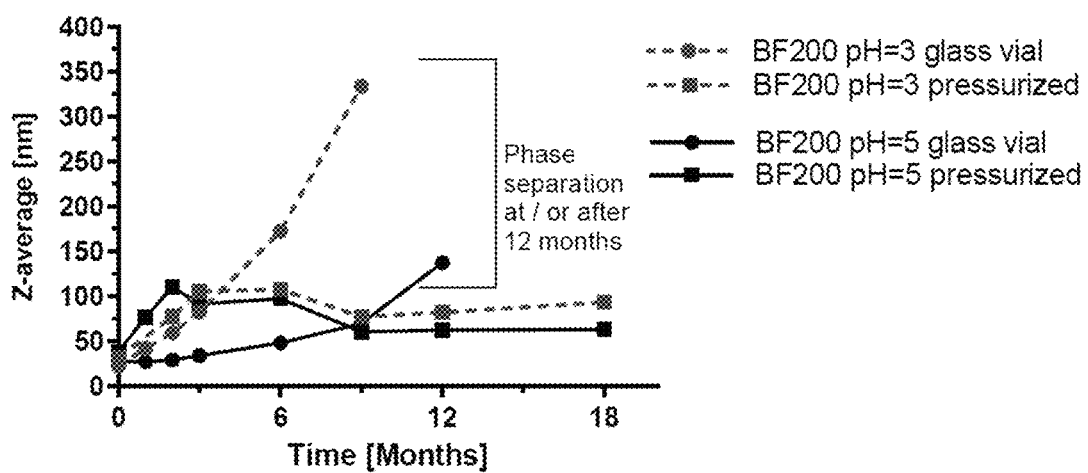

FIG. 3: Comparison of nanoemulsion formulations with different pH values and without gelling agent: vesicle size over time at different temperatures.

Figure 4:
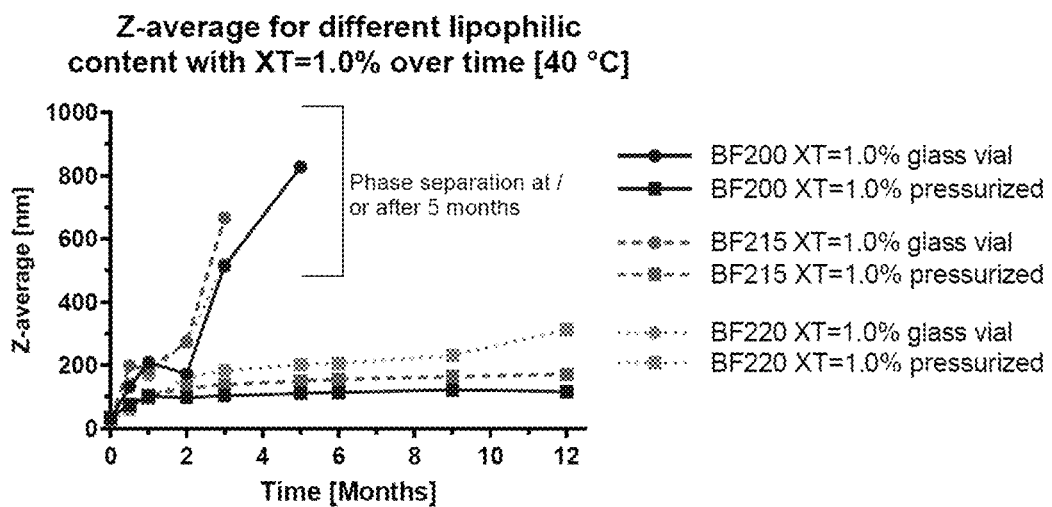
Figure 4:
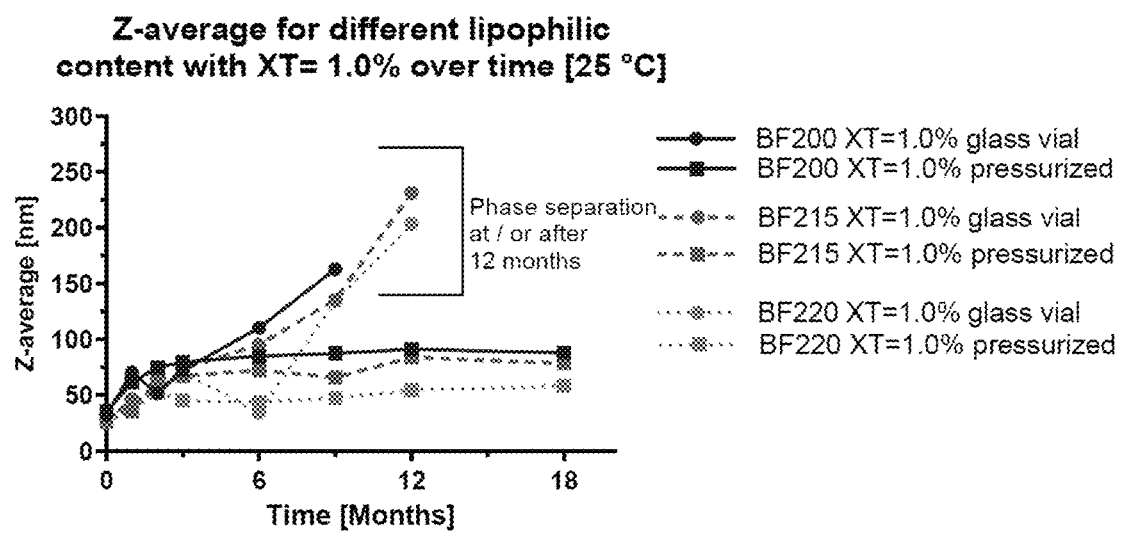

FIG. 4: Comparison of nanoemulsion formulations with different lipophilic contents and with XT=1%: vesicle size over time at different temperatures.

Figure 5:
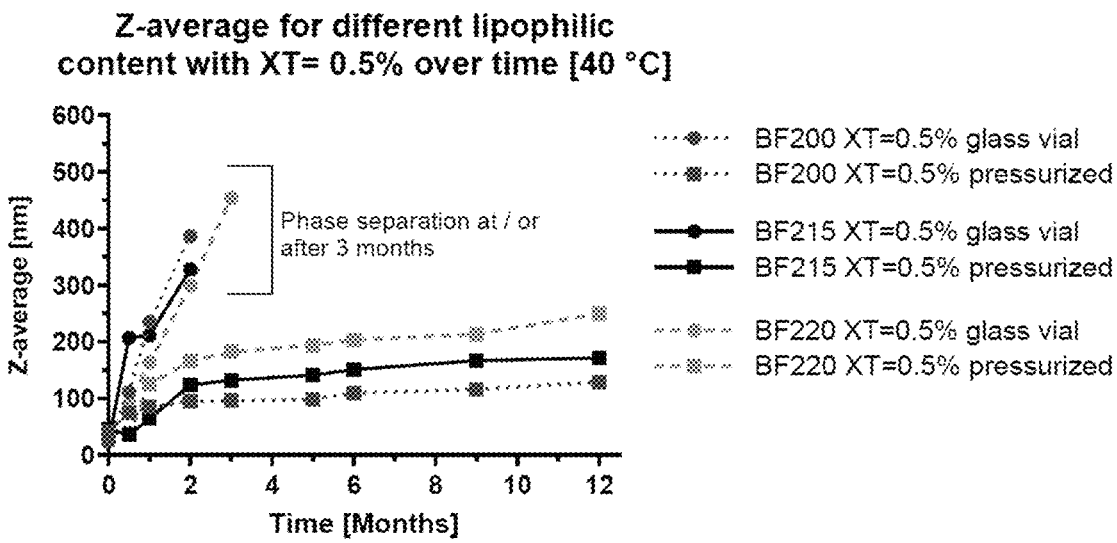
Figure 5:
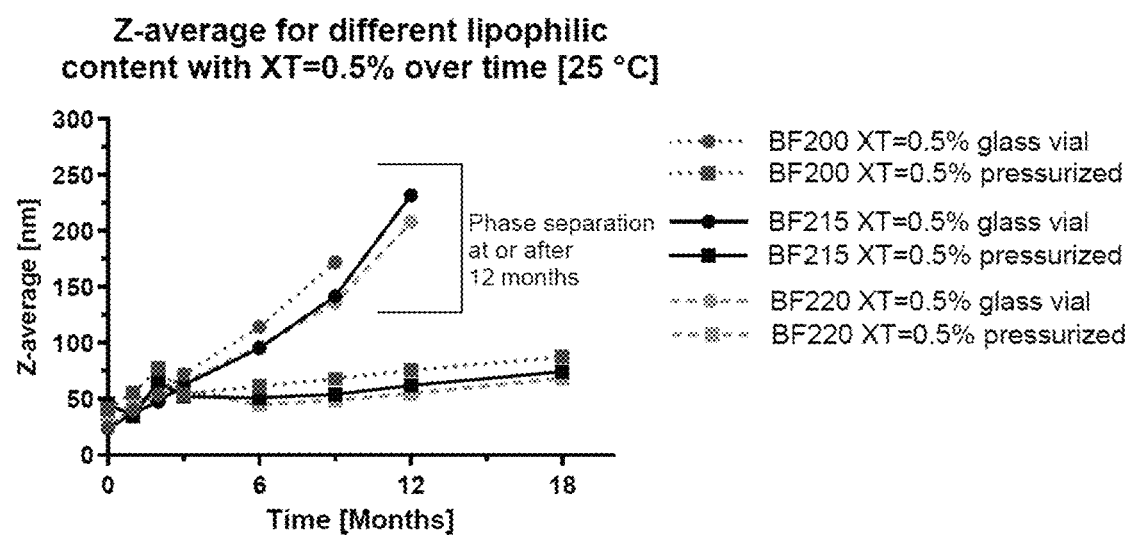

FIG. 5: Comparison of nanoemulsion formulations with different lipophilic contents and with XT=0.5%: vesicle size over time at different temperatures.

Figure 6:
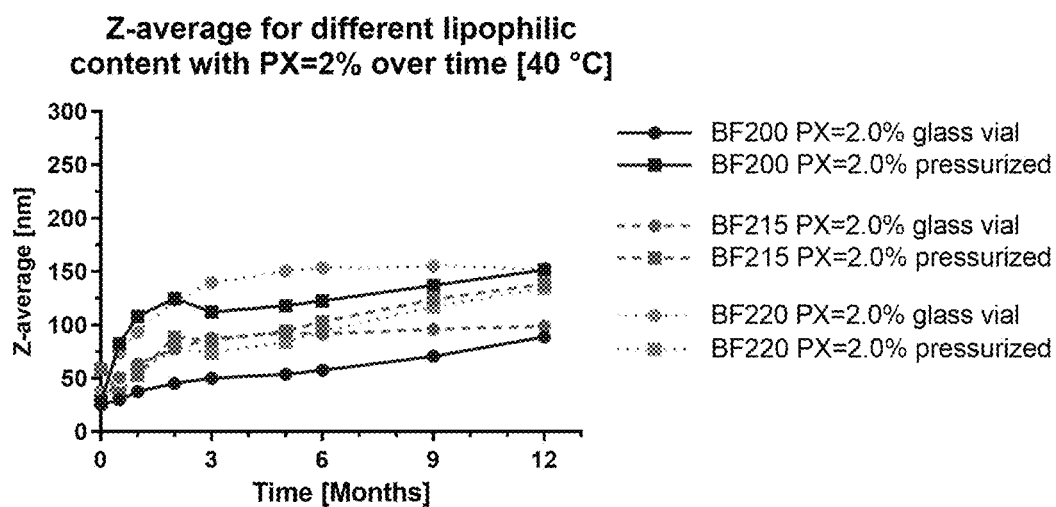
Figure 6:
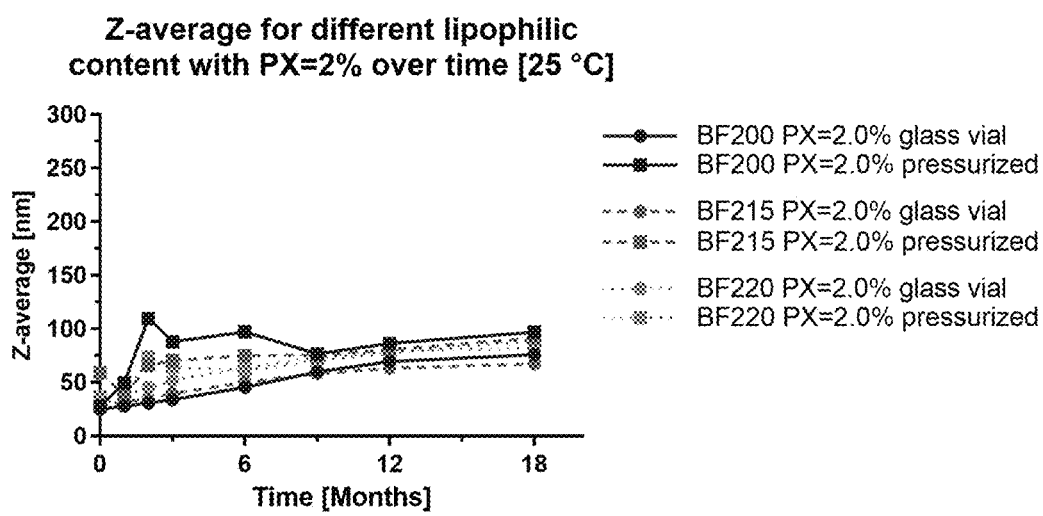

FIG. 6: Comparison of nanoemulsion formulations with different lipophilic contents and with PX=2%: vesicle size over time at different temperatures.

Figure 7:
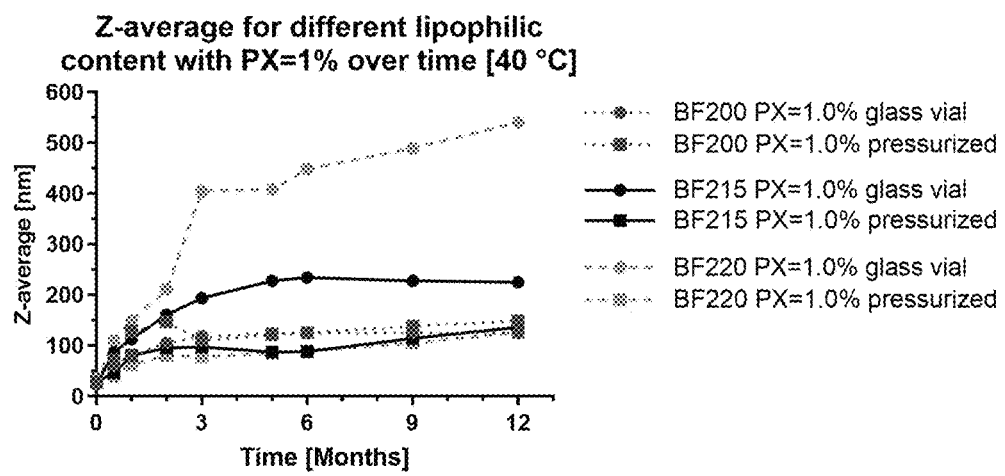
Figure 7:
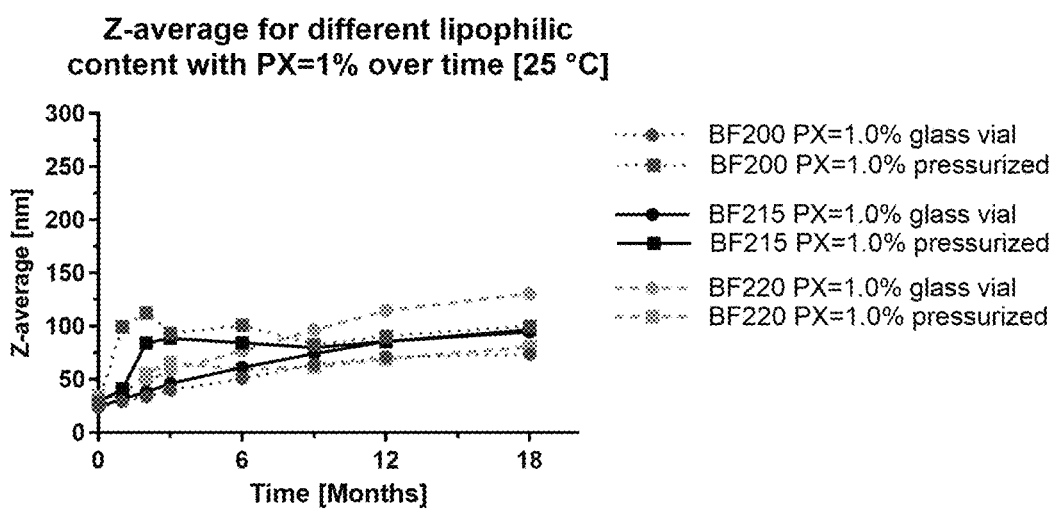

FIG. 7: Comparison of nanoemulsion formulations with different lipophilic contents and with PX=1%: vesicle size over time at different temperatures.

Figure 8:
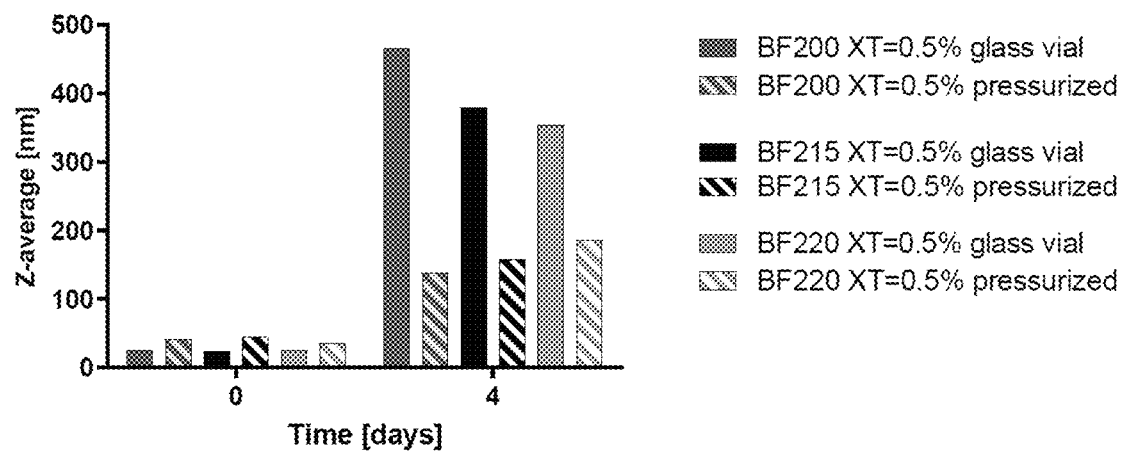
Figure 8:
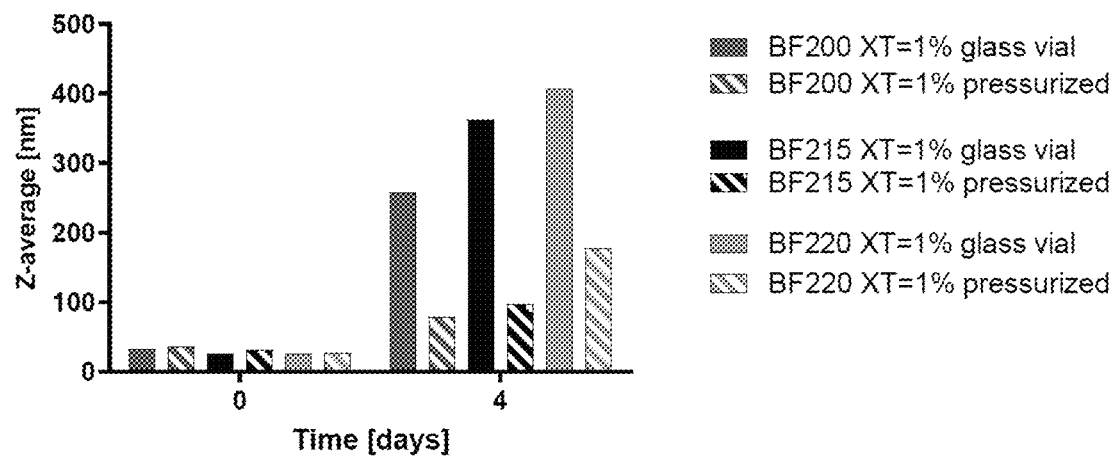

FIG. 8: Comparison of nanoemulsion formulations with different lipophilic contents and with xanthan gum as frost protection (4 days freezing, one time). From left to right: BF200 XT=0.5%/1.0% glass, BF200 XT=0.5%/1.0% foam, BF215 XT=0.5%/1.0% glass, BF215 XT=0.5%/1.0% foam, BF220 XT=0.5%/1.0% glass, BF220 XT=0.5%/1.0% foam.

Figure 9:
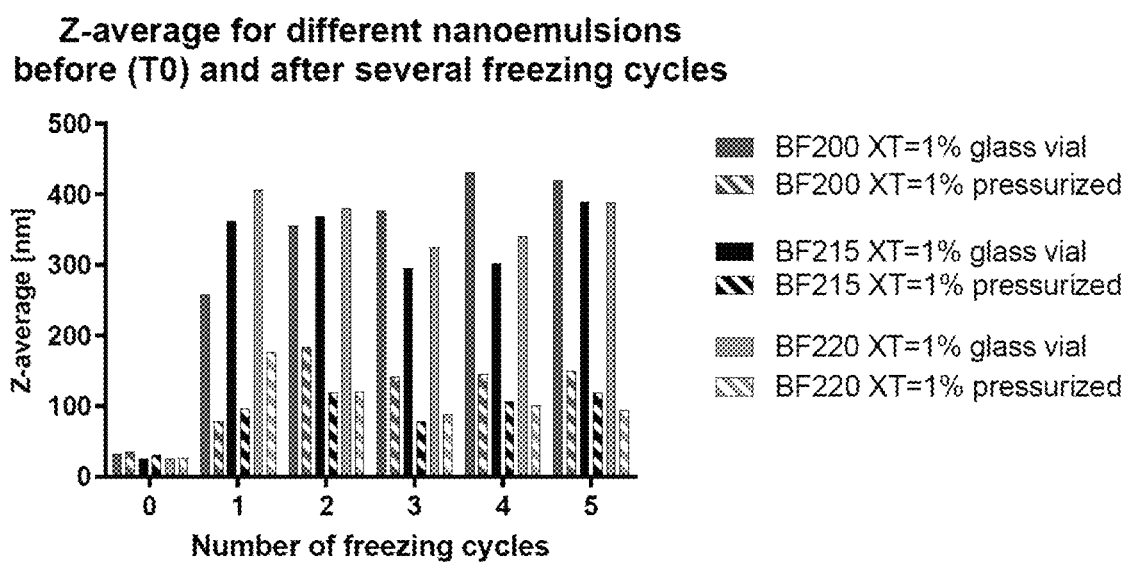

FIG. 9: Comparison of nanoemulsion formulations with different lipophilic contents and with xanthan gum as frost protection (5 freeze-thaw cycles). From left to right: BF200 XT=1% glass, BF200 XT=1% foam, BF215 XT=1% glass, BF215 XT=1% foam, BF220 XT=1% glass, BF220 XT=1% foam.

Figure 10:
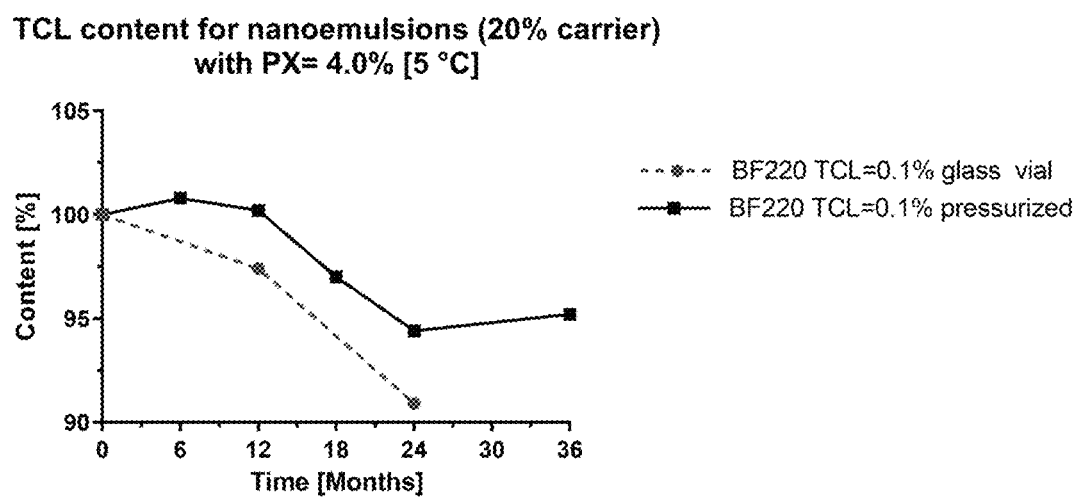

FIG. 10: Comparison of TC-content over time in BF220 with PX=4% as gelling agent at 5° C.

Figure 11:
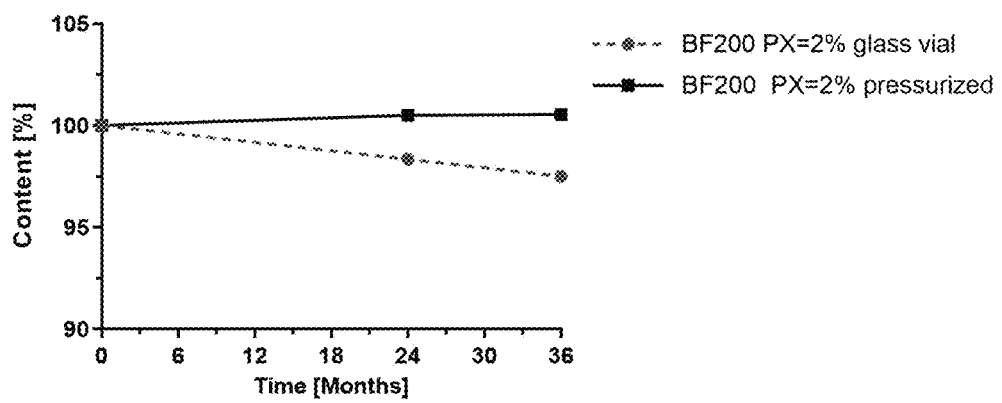
Figure 11:
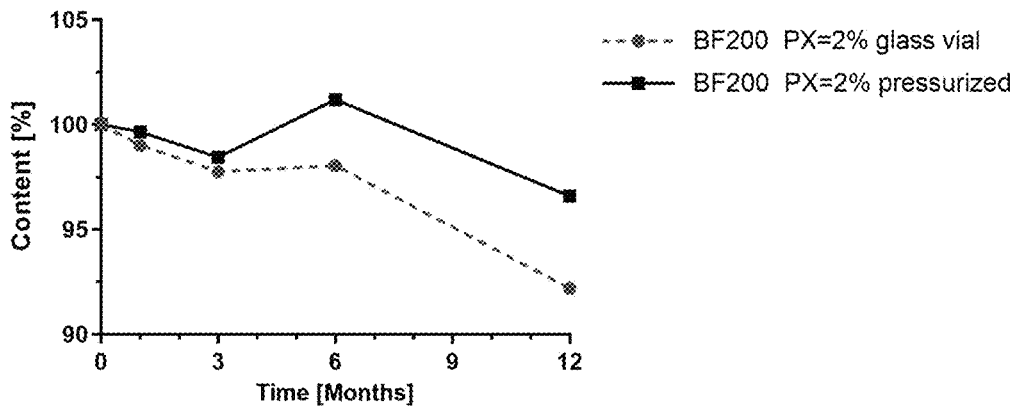

FIG. 11: Comparison of ALA-content over time in BF200 with PX=2% as gelling agent at 5° C. and 25° C.

Figure 12:
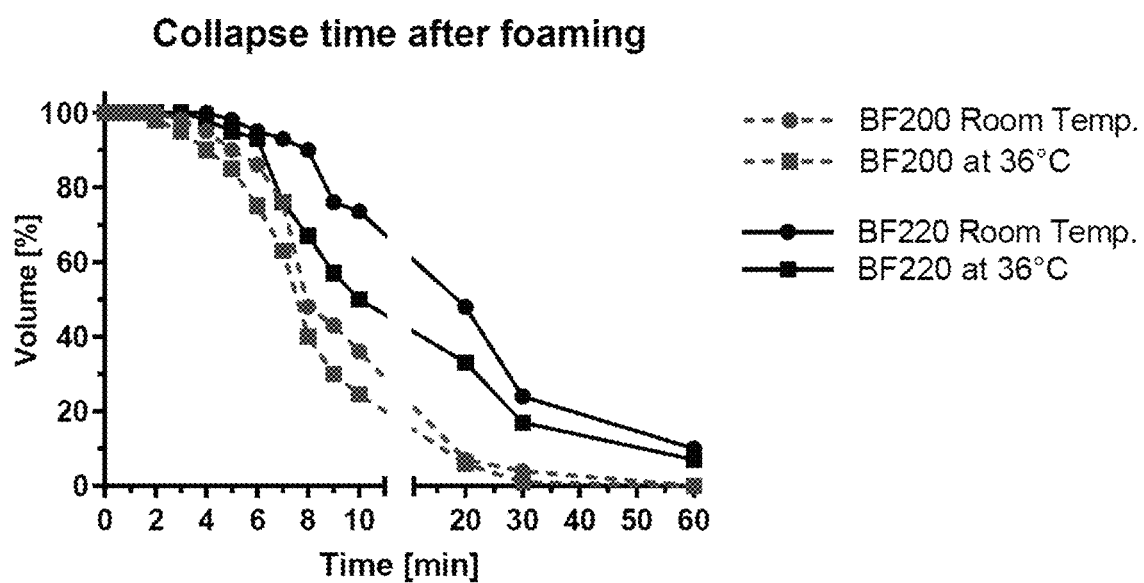

FIG. 12: Analysis of foam collapse times at room temperature and 36° C. of nanoemulsions BF200 and BF220 as described in Table 2.

EXAMPLES

In the Examples, vesicle size and API content, describing stability of nanoemulsion formulations are determined, depending on lipophilic content, pH and gelling agents under various conditions (0° C., 25° C., 40° C., freeze-thaw cycles).

Example 1: Preparation of Nanoemulsions BF200, BF215 and BF220 and Nanoemulsion Formulations

TABLE 1

| Lipophilic content of nanoemulsions used in the Examples | |
| --- | --- |
| BF200 | 10% lipophilic content |
| BF215 | 15% lipophilic content |
| BF220 | 20% lipophilic content |

The qualitative and quantitative compositions of the nanoemulsions BF200, BF215 and BF220 are given in Table 2.

TABLE 2

Composition of nanoemulsions BF200, BF215 and BF220

| | Ingredient | Content (% w/w) BF200 | Content (% w/w) BF215 | Content (% w/w) BF220 | Function | Quality |
|---|---|---|---|---|---|---|
| 1 | Soy lecithin | 1.7 | 2.0-3.0 | 3.0-4.0 | surfactant | >90% phosphadidylcholine, for pharmaceutical use, USP |
| 2 | Polysorbate 80 (polyoxyethylene sorbitol monooleate) | 3.4 | 4.5-5.5 | 6.0-7.0 | surfactant | Ph. Eur. |
| 3 | Caprylic/capric triglycerides | 3.5 | 4.5-5.5 | 6.0-8.0 | lipid core | Ph. Eur. |
| 4 | Isopropyl alcohol | 1.4 | 2.0-3.0 | 2.0-4.0 | solvent | Ph. Eur. |
| | Content (% w/w) ingredients 1-4 | 10.0 | 15.0 | 20.0 | | |
| | 10 mM phosphate buffer, pH 6 | ad 100.00 | ad 100.00 | ad 100.00 | solvent | Water for injection: Ph. Eur.; Disodium phosphate and sodium hydrogen phosphate: Ph. Eur. |

The formulations are free of a gelling agent, such as Poloxamer 407.

The manufacturing process for the nanoemulsions in a typical batch size consists of the following steps 1-4:

Step 1: Preparation of a 10 mM Phosphate Buffer (Aqueous Component)

10 mM phosphate buffer (1000 g), pH 6, was prepared optionally sterilized by filtration through a sterile filter.

Step 2: Preparation of a Carrier Containing the Lipophilic Component, the Surfactants and the Alcohol

TABLE 3

| Carrier component | |
|---|---|
| Ingredient | Weight (g) |
| Soy lecithin | 17 |
| Polysorbate 80 (polyoxyethylene sorbitol monooleate) | 34 |
| Caprylic/capric triglycerides | 35 |
| Isopropyl alcohol | 14 |

Soy lecithin (17 g) was weighed in a suitable vessel, isopropyl alcohol (14 g) was added and the vessel was covered to avoid alcohol evaporation. Soy lecithin was dissolved under continuous stirring with a suitable stirrer at room temperature. Caprylic/capric triglycerides (35 g) and Polysorbate 80 (34 g) were weighed and added to the solution of soy lecithin. The mixture was stirred with a suitable stirrer at room temperature until a homogenous clear solution was obtained. This solution is the carrier phase to be included in the nanoemulsion containing all emulsifiers and lipid components of the nanoemulsion BF200. According to this procedure BF215 and BF220 was prepared by adapting the amount of the components (see Table 2).

Step 3: Manufacturing of the Nanoemulsion by Mixing the Aqueous Component from Step 1 and the Carrier from Step 2 for a Lipid Content of 10% (BF200)

Manufacturing of an emulsion by mixing 900 g phosphate buffer (from Step 1) and 100 g carrier (from Step 2). First, the aqueous component comprising the phosphate buffer was heated to approximately 45° C.-60° C. in a suitable vessel. Then, the carrier (concentrate) of step 2 was heated to approximately 45° C.-60° C. Subsequently, the carrier was poured to the phosphate buffer under continuous stirring with a propeller mixer resulting in the formation of a stable trombe (or spout) having the maximal possible diameter without causing foaming or sputtering. The resulting nanoemulsion was stirred for about 15 min. Finally, the nanoemulsion was cooled down to room temperature.

In nanoemulsion BF215, 850 g phosphate buffer (from Step 1) and 150 g carrier were mixed. In nanoemulsion BF220, 800 g phosphate buffer (from Step 1) and 200 g carrier were mixed.

In the following examples, the terms "nanoemulsion BF200", "nanoemulsion BF215", and "nanoemulsion BF220" are used to describe nanoemulsions prepared according to steps 1-3. Nanoemulsions BF200, BF215 and BF220 were used in Examples A and G.

Step 4: Preparation of the Final Nanoemulsion Formulation and Primary Packaging

The nanoemulsion was optionally sterilized by filtration through a sterile filter and filled into 100 ml sterile glass bottles under laminar flow hood.

Depending on the purpose of the nanoemulsion, one may add adjuvants and/or excipients and/or active ingredients (at the appropriate step according to the description) and/or dilute the nanoemulsion in a way to get a suitable "nanoemulsion formulation", e.g., by adding water, a suitable buffer, or an aqueous gel base with poloxamer 407 or xanthan gum.

In the following examples, the terms "nanoemulsion formulation BF200", "nanoemulsion formulation BF215", and "nanoemulsion formulation BF220" are used to describe nanoemulsion formulations prepared according to steps 1-4.

The abbreviations "BF200", "BF215", and "BF220" are used both for (stock) nanoemulsions and for nanoemulsion formulations.

The nanoemulsions or nanoemulsion formulations were filled into a conventional glass vials ("BF200 glass vial", "BF215 glass vial" and "BF220 glass vial") or a foam dispenser, pressurized with a mixture of propane, isobutane and n-butane ("BF200 pressurized", "BF215 pressurized" and "BF220 pressurized"). Typical examples of dispensers (pressurized containers) and a glass vial are shown in FIG. 1.

Example 2: Preparation of Nanoemulsion BF200, BF215 and BF220 at pH 3 or 5

The BF200, BF215 and BF220 nanoemulsions are produced according to Example 1, Step 1-3, except that in Step 3 (manufacturing of the nanoemulsion by mixing the aqueous component from Step 1 and the carrier from Step 2), a phosphate buffer with an appropriate pH is used. Other acids different to phosphoric acid and it salts can be used for pH adjustment. If necessary, the pH may be additionally adjusted by adding a suitable acids, salts or buffers.

The BF200, BF215 and BF220 nanoemulsions were filled into a conventional glass vial ("BF200 pH=3 glass", "BF200 pH=5 glass", "BF215 pH=3 glass", "BF220 pH=3 glass") or a foam dispenser ("BF200 pH=3 foam", "BF200 pH=5 foam", "BF215 pH=3 foam", "BF220 pH=3 foam"), as described in Example 1.

The nanoemulsions described in this example were used in Example B.

Example 3: Preparation of Nanoemulsion Formulations BF200, BF215 and BF220 Containing 0.5 or 1% w/w of Xanthan The nanoemulsion formulations BF200, BF215 and BF220 are produced according to Example 1 with the addition of the appropriate amount of an aqueous gel base with xanthan gum in step 4.

The formulations were filled into a conventional glass vial ("BF200 XT=0.5% glass", "BF215 XT=0.5% glass", "BF220 XT=0.5% glass") or a foam dispenser ("BF200 XT=0.5% foam", "BF215 XT=0.5% foam", and "BF220 XT=0.5% foam"), as described in Example 1.

The formulations were filled into a conventional glass vial ("BF200 XT=1.0% glass", "BF215 XT=1.0% glass", "BF220 XT=1.0% glass") or a foam dispenser ("BF200 XT=1.0% foam", "BF215 XT=1.0% foam", and "BF220 XT=1.0% foam"), as described in Example 1.

The nanoemulsion formulations described in this example were used in Examples C, D, G and H.

Example 4: Preparation of Nanoemulsion Formulations BF200, BF215 and BF220 Containing 1 or 2% w/w of Poloxamer 407 (PX)

The nanoemulsion formulations are produced according to Example 1 with the addition of the appropriate amount of an aqueous gel base with poloxamer 407 in step 4.

The formulations were filled into a conventional glass vial ("BF200 PX=2.0% % glass", "BF215 PX=2.0% % glass", "BF220 PX=2.0% % glass") or a foam dispenser ("BF200 PX=2.0% % foam", "BF215 PX=2.0% % foam", and "BF220 PX=2.0% % foam"), as described in Example 1.

Nanoemulsion formulations BF200 PX=2.0% glass, BF215 PX=2.0% glass, BF220 PX=2.0% glass, BF200 PX=2.0% foam, BF215 PX=2.0% foam, and BF220 PX=2.0% foam, as described herein, were used in Example E.

The formulations were filled into a conventional glass vial ("BF200 PX=1.0% % glass", "BF215 PX=1.0% % glass", "BF220 PX=1.0% % glass") or a foam dispenser ("BF200 PX=1.0% % foam", "BF215 PX=1.0% % foam", and "BF220 PX=1.0% % foam"), as described in Example 1.

Nanoemulsion formulations BF200 PX=1.0% glass, BF215 PX=1.0% glass, BF220 PX=1.0% glass, BF200 PX=1.0% foam, BF215 PX=1.0% foam, and BF220 PX=1.0% foam, as described herein, were used in Example F.

Example 5: Preparation of Nanoemulsion Formulation BF200 Containing 3% 5-Aminolevulinic Acid and 2% Poloxamer 407

The formulations were prepared according to Example 1 with the addition of the appropriate amount of an aqueous gel base with poloxamer 407 in step 4. 5-ALA in an amount of 3% was added.

The nanoemulsion formulations described in this example were used in Example I.

Example 6: Preparation of Nanoemulsion Formulation BF220 Containing 0.1% Tacrolimus (TC) and 4% Poloxamer 407

The formulations were prepared according to Example 1 with the addition of the appropriate amount of an aqueous gel base with poloxamer 407 in step 4. TC in an amount of 0.1% was added.

The nanoemulsion formulations described in this example were used in Example J.

Example 7: Determination of Vesicle Size and Polydispersity Index by Dynamic Light Scattering The size, expressed as the z-average size (e.g., in nm), and the polydispersity index of nanoemulsion formulations was determined by dynamic light scattering (sometimes referred as Photon Correlation Spectroscopy (PCS) or Quasi-Elastic Light Scattering (QELS)). The technique is well known in the art and well established to determine size of nano or micro particles or vesicles in emulsions, suspensions or polymeric solutions with a laser. For foam samples, the analysis was performed following collapse of the foam. Measurements were conducted with an Zetasizer Nano ZS (Malvern Instruments Ltd, Malvern, Worcestershire, UK). The measurement was performed according to the manufacturer's instructions.

The Zetasizer Nano ZS is instrumented with a 633 nm green laser and optics with a 173°scattering detector angle for size measurement. The device may be operated under vacuum for measurements, but in these cases, vacuum was not applied to the samples for size and homogeneity measurements.

Example 8: Determination of Viscosity

Viscosity was measured by rotation (measuring geometry: cone/plate) with a constant shear rate of $90.0 \text{ s}^{-1}$ at 20° C.

Example A

Comparison of Nanoemulsions with Different Lipophilic Contents and without Gelling Agent: Vesicle Size Over Time at Different Temperatures and Polydispersity Index Over Time Nanoemulsions BF200, BF215 and BF220 were prepared as described in Example 1. The nanoemulsions were stored for 18 months at 25° C. or 12 months at 40° C. The size of the nanovesicles was determined at 0 (starting point) and various time points during the storage period by dynamic light scattering as described in Example 7. The results are shown in FIG. 2 and Table 4.

TABLE 4

Polydispersity index of nanoemulsions
BF200, BF215 and BF220 stored at 40° C.

| Storage time and container closure system | BF200 | BF215 | BF220 |
|---|---|---|---|
| 0 month | 0.07 | 0.15 | 0.17 |
| 1 month pressurized | 0.19 | 0.14 | 0.11 |
| 1 month glass vial | 0.22 | 0.25 | 0.15 |
| 3 months pressurized | 0.06 | 0.06 | 0.02 |
| 3 months glass vial | | Phase separation | |
| 6 months pressurized | 0.06 | 0.07 | 0.04 |
| 6 months glass vial | | Phase separation | |
| 9 months pressurized | 0.20 | 0.06 | 0.02 |
| 9 months glass vial | | Phase separation | |
| 12 months pressurized | 0.16 | 0.05 | 0.02 |
| 12 months glass vial | | Phase separation | |

When the nanoemulsion (without gelling agents) is stored in a pressurized can the vesicle size is extremely stable at ambient conditions (25° C.) and stressed conditions (40° C.), compared with conventional storage in a glass vial that degrade much earlier under phase separation.

Conclusion: The pressurized can is extremely advantageous for storage at ambient and stressed conditions.

Example B

Comparison of Nanoemulsions with Different pH Values and without Gelling Agent: Vesicle Size Over Time at Different Temperatures Nanoemulsions BF200 pH=3 glass, BF200 pH=5 glass, BF200 pH=3 foam, and BF200 pH=5 foam, BF215 pH=3 glass, BF220 pH=3 glass, BF215 pH=3 foam, and BF220 pH=3 foam were prepared as described in Example 2. The nanoemulsions were stored 18 months at 25° C. or 12 months at 40° C. The size of the nanovesicles was determined at 0 (starting point) and various time points during the storage period by dynamic light scattering as described in Example 7. The results are shown in FIG. 3 and Table 5.

TABLE 5

Vesicle size after 12 months of storage at 40° C. without any stabilizing agent.

| Formulation | Vesicle size of samples stored in glass vial | Vesicle size of samples stored under pressure |
|---|---|---|
| 10% lipophilic content (BF200), pH = 3 | Phase separation | 143.4 nm |
| 10% lipophilic content (BF200), pH = 5 | Phase separation | 70.78 nm |
| 15% lipophilic content (BF215), pH = 3 | Phase separation | 142.85 nm |
| 20% lipophilic content (BF220), pH = 3 | Phase separation | 186.35 nm |

In a glass vial, the combination of acidic pH and high temperatures (e.g., 40° C.) impairs the stability of the vesicle size in the nanoemulsion (phase separation) over storage for 12 months.

At 40° C., in the pressurized can as storing unit, vesicle size remained below 190 nm over 12 months.

In a glass vial, the combination of acidic pH and ambient temperatures (e.g., 25° C.) impairs the stability of the vesicle size in the nanoemulsion (phase separation) over storage for 18 months.

At 25° C., in the pressurized can as storing unit, vesicle size remained below 95 nm over 18 months.

Conclusion: The pressurized can is extremely advantageous for storage of nanoemulsions at pH 3 or pH 5 at ambient and elevated temperatures (e.g., 25° C. and 40° C.).

Example C

Comparison of Nanoemulsion Formulations with Different Lipophilic Contents and with Xanthan (XT)=1%: Vesicle Size Over Time at Different Temperatures Nanoemulsion formulations BF200 XT=1.0% glass, BF215 XT=1.0% glass, BF220 XT=1.0% glass, BF200 XT=1.0% foam, BF215 XT=1.0% foam, and BF220 XT=1.0% foam, were prepared as described in Example 3. The nanoemulsion formulations were stored for 18 months at 25° C. or 12 months at 40° C. The size of the nanovesicles was determined at 0 (starting point) and various time points during the storage period by dynamic light scattering as described in Example 7. The results are shown in FIG. 4.

In a glass vial, high temperatures (e.g., 40° C.) impair the stability of the vesicle size in the nanoemulsion (phase separation) over storage for 12 months.

At 40° C., in the pressurized can as storing unit, vesicle size remained below 315 nm over 12 months.

In a glass vial, the ambient temperatures (e.g., 25° C.) impairs the stability of the vesicle size in the nanoemulsion (phase separation) over storage for 18 months.

At 25° C., in the pressurized can as storing unit, vesicle size remained below 90 nm over 18 months.

Conclusion: The pressurized can is extremely advantageous for storage of nanoemulsion formulations containing xanthan as a gelling agent at ambient (25° C.) and elevated temperatures (e.g., 40° C.). XT=1% has a stabilizing effect at standard conditions (glass vial) and lower temperatures (5° C.), especially for nanoemulsion formulations with high lipophilic content (BF215, BF220).

Example D

Comparison of Nanoemulsion Formulations with Different Lipophilic Contents and with XT=0.5%: Vesicle Size Over Time at Different Temperatures Nanoemulsion formulations BF200 XT=0.5% glass, BF215 XT=0.5% glass, BF220 XT=0.5% glass, BF200 XT=0.5% foam, BF215 XT=0.5% foam, and BF220 XT=0.5% foam, were prepared as described in Example 3. The nanoemulsion formulations were stored for 18 months at 25° C. or 12 months at 40° C. The size of the nanovesicles was determined at 0 (starting point) and various time points during the storage period by dynamic light scattering as described in Example 7. The results are shown in FIG. 5.

In a glass vial, high temperatures (e.g., 40° C.) impairs the stability of the vesicle size in the nanoemulsion (phase separation) over storage for 12 months.

At 40° C., in the pressurized can as storing unit, vesicle size remained below 250 nm over 12 months.

In a glass vial, the ambient temperatures (e.g., 25° C.) impairs the stability of the vesicle size in the nanoemulsion (phase separation) over storage for 18 months.

At 25° C., in the pressurized can as storing unit, vesicle size remained below 90 nm over 18 months.

Conclusion: The pressurized can is extremely advantageous for storage of nanoemulsion formulations containing xanthan as a gelling agent at ambient (25° C.) and elevated temperatures (e.g., 40° C.).

Example E

Comparison of Nanoemulsion Formulations with Different Lipophilic Contents and with Poloxamer 407 (PX)=2%: Vesicle Size Over Time at Different Temperatures Nanoemulsion formulations BF200 PX=2.0% glass, BF215 PX=2.0% glass, BF220 PX=2.0% glass, BF200 PX=2.0% foam, BF215 PX=2.0% foam, and BF220 PX=2.0% foam, were prepared as described in Example 4. The nanoemulsion formulations were stored for 18 months at 25° C. or 12 months at 40° C. The size of the nanovesicles was determined at 0 (starting point) and various time points during the storage period by dynamic light scattering as described in Example 7. The results are shown in FIG. 6.

At all conditions, vesicle size after 12 months storage was below 160 nm (40° C.) or 110 nm (25° C.), indicating a stabilizing effect of 2% Poloxamer 407 in a pressurized can as in a conventional storing unit (glass vial).

Conclusion: Poloxamer 407 stabilizes the nanoemulsion over 18 months storage at 25-40° C. in a pressurized can and a glass vial.

Example F

Comparison of Nanoemulsion Formulations with Different Lipophilic Contents and with Poloxamer 407 (PX)=1%: Vesicle Size Over Time at Different Temperatures Nanoemulsion formulations BF200 PX=1.0% glass, BF215 PX=1.0% glass, BF220 PX=1.0% glass, BF200 PX=1.0% foam, BF215 PX=1.0% foam, and BF220 PX=1.0% foam, were prepared as described in Example 4. The nanoemulsion formulations were stored for 18 months at 25° C. or 12 months at 40° C. The size of the nanovesicles was determined at 0 (starting point) and various time points during the storage period by dynamic light scattering as described in Example 7. The results are shown in FIG. 7.

At 40° C. storage for 12 months, vesicle size increases to 234-541 nm at high lipid content (BF215, BF220) in glass vial. In the samples stored in a pressurized can vesicle size remained below 160 nm.

After 18 months, the vesicle size remained at or below 100 nm (25° C.). At high lipid content (BF220) in glass vial increased up to 131 nm.

Conclusion: PX=1% has a stabilizing effect at ambient temperature (25° C.), this effect is strengthen by pressurized container closure system. A pressurized container closure system improves the stability at 40° C.

Example G

Comparison of Nanoemulsion Formulations with Different Lipophilic Contents and with Xanthan Gum as Frost Protection Nanoemulsion formulations BF200 XT=0% glass (=BF200 glass), BF215 XT=0% glass (=BF215 glass), BF220 XT=0% glass (=BF220 glass), BF200 XT=0% foam (=BF200 foam), BF215 XT=0% foam (=BF215 foam), and BF220 XT=0% foam (=BF220 foam), were prepared as described in Example 1.

Nanoemulsion formulations BF200 XT=0.5% glass, BF215 XT=0.5% glass, BF220 XT=0.5% glass, BF200 XT=0.5% foam, BF215 XT=0.5% foam and BF220 XT=0.5% foam, were prepared as described in Example 3.

Nanoemulsion formulations BF200 XT=1.0% glass, BF215 XT=1.0% glass, BF220 XT=1.0% glass, BF200 XT=1.0% foam, BF215 XT=1.0% foam and BF220 XT=1.0% foam, were prepared as described in Example 3.

The formulations were stored for 4 days at −24° C. and thawed thereafter (one freeze-thaw cycle). Vesicle size was determined, as described in Example 7. The results are described in FIG. 8 and Table 6.

TABLE 6

Vesicle size after one freeze thaw cycle with a pH = 3.

| Formulation | Vesicle size of samples stored in glass vial | Vesicle size of samples stored under pressure |
|---|---|---|
| 10% lipophilic content (BF200) c (xanthan gum) = 0.5%* | 465.8 nm | 138.1 nm |
| 10% lipophilic content (BF200) c (xanthan gum) = 1.0% | 258.0 nm | 79.0 nm |
| 15% lipophilic content (BF215) c (xanthan gum) = 0.5% | 379.3 nm | 157.5 nm |
| 15% lipophilic content (BF215) c (xanthan gum) = 1.0% | 362.0 nm | 97.0 nm |
| 20% lipophilic content (BF220) c (xanthan gum) = 0.5% | 353.6 nm | 186.5 nm |
| 20% lipophilic content (BF220) c (xanthan gum) = 1.0% | 407.0 nm | 177.0 nm |

*c (xanthan gum): content of xanthan gum, % w/w.

Nanoemulsion formulations containing xanthan gum are better protected under freezing conditions, when stored in pressurized cans (compared to conventional storing units, i.e., glass vials).

In the absence of xanthan (XT=0%), this is not the case.

Conclusion: Frost protection, for example by xanthan gum can ensure appropriate freeze protection in pressurized cans. The combination of xanthan gum and pressurized can is superior to any "non-pressurized" conditions, such as storage in a conventional glass vial.

Example H

Comparison of Nanoemulsion Formulations with Different Lipophilic Contents and with Xanthan Gum as Frost Protection Nanoemulsion formulations BF200 XT=1.0% glass, BF215 XT=1.0% glass, BF220 XT=1.0% glass, BF200

XT=1.0% foam, BF215 XT=1.0% foam and BF220 XT=1.0% foam, will be prepared as described in Example 3.

Other nanoemulsions were not prepared based on the results of example G.

The formulations undergo 5 freeze-thaw cycles. In a cycle, the nanoemulsion will be frozen at −24° C., thereafter thawed at room temperature. After final thawing, vesicle size will be determined after thawing, as described in Example 7. The results are described in FIG. 9 and Table 7.

TABLE 7

Vesicle size after five freeze-thaw cycles with a pH = 3.

| Formulation | Vesicle size of samples stored in glass vial | Vesicle size of samples stored under pressure |
|---|---|---|
| 10% lipophilic content (BF200) c (xanthan gum) = 1.0% | 420.5 nm | 150.0 nm |
| 15% lipophilic content (BF215) c (xanthan gum) = 1.0% | 388.6 nm | 119.1 nm |
| 20% lipophilic content (BF220) c (xanthan gum) = 1.0% | 388.1 nm | 94.0 nm |

In all conditions tested, improved stability after 5 freeze-thaw cycles is found in a nanovesicle formulation stored in a pressurized container, wherein the formulations comprised a gelling agent as frost protectant, for example xanthan gum. The combination of xanthan gum and pressurized container is found to be superior to any "non-pressurized" conditions, such as storage in a conventional glass vial.

Example I

Comparison of 5-Aminolevulinic Acid (ALA, 5-ALA) Content Over Time in BF200 with PX=2% as Gelling Agent at Different Temperatures Nanoemulsion formulations BF200 PX=2% glass and BF200 PX=2% foam were prepared as described in Example 5. The nanoemulsion formulations were stored at 25° C. and 2-8° C. The content of ALA was determined at 0 (starting point) and various time points during the 36 months storage period. The results are shown in FIG. 11.

Conclusion: at all conditions: pressurized cans preserve the API (5-ALA) content better than conventional storing units (e.g., glass vials). After 36 months storage at 2-25° C., the ALA content was at least 90%.

Example J

Comparison of Tacrolimus (TC) Content Over Time in BF220 with PX=4% as Gelling Agent at Different Temperatures Nanoemulsion formulations BF220 TC=0.1% glass and BF220 TC=0.1% foam were prepared as described in Example 6. The nanoemulsion formulations were stored at 2-8° C. The content of TC was determined at 0 (starting point) and various time points during the 36 months storage period. The results are shown in FIG. 10.

Conclusion: At 2-8° C.: pressurized cans preserve the API (TC) content better than conventional storing units (e.g., glass vials). The formulation stored in a pressurized container was found to be stable for at least 36 months storage at 2-8° C. (5° C.). After 36 months storage at 2-8° C., the TC content was at least 90%.

The invention claimed is:

1. A formulation comprising:
   (a) a nanoemulsion comprising:
      (i) at least one aqueous component;
      (ii) a carrier component comprising:
         (1) at least one lipophilic component,
         (2) at least one surfactant, and
         (3) at least one alcohol; and
   (b) a propellant,
   wherein the formulation is comprised in a pressurized container;
   wherein the formulation comprises less than 0.5% (w/w) based on the total weight of the formulation or no fatty alcohol;
   wherein the formulation comprises an active agent;
   wherein the active agent is 5-aminolevulinic acid, a pharmaceutically acceptable salt thereof, or a pharmaceutically acceptable derivative thereof; and
   wherein the pharmaceutically acceptable derivative thereof comprises esters, ethers, thioesters, methyl-thioesters, thioethers, methyl-thioethers methoxy-substituted benzyl ethers, silyl ethers, sulfonates, sulfenates, sulfinates, carbonates, cyclic carbonates, carbamates, cyclic acetals, cyclic ketals, ketones, chiral ketones, hydrazones, enamines and/or enols.

2. The formulation of claim 1, wherein the formulation comprises less than 0.5% (w/w) based on the total weight of the formulation or no fatty acid.

3. The formulation of claim 2, wherein the formulation comprises less than 0.5% (w/w) based on the total weight of the formulation or no gelling agent.

4. The formulation of claim 3, wherein the formulation comprises less than 0.5% (w/w) based on the total weight of the formulation or no emollient selected from a monoester or diester comprising an alcohol and a fatty acid.

5. The formulation of claim 2, wherein the formulation comprises a gelling agent, wherein the gelling agent is present in an amount of 0.1% to 10% (w/w) based on the total weight of the formulation.

6. The formulation of claim 5, wherein the gelling agent is a poloxamer, wherein the poloxamer is present in an amount of 0.5% to 4% (w/w) based on the total weight of the formulation.

7. The formulation of claim 6, wherein the at least one lipophilic component is present in an amount of 10% to 30% (w/w) based on the total weight of the nanoemulsion (a).

8. The formulation of claim 1, wherein the nanoemulsion:
   a. comprises nanovesicles having a size of less than or equal to 500 nm when stored one month, two months, three months, six months, or twelve months at 2-40° C., at 10-40° C., at 20-40° C., at 30-40° C., or at 40° C. in the pressurized container; and/or
   b. is characterized by a polydispersity index of less than or equal to 0.4, when stored one month, two months, three months, six months, or twelve months, at 2-40° C., at 10-40° C., at 20-40° C., at 30-40° C., or at 40° C. in the pressurized container; and/or
   c. comprises nanovesicles having a size of less than or equal to 500 nm when stored one month, two months, three months, six months, twelve months, eighteen months, or twenty-four months at 2-25° C., at 10-25° C., at 15-25° C., at 2-8° C., at 5° C. or at 25° C. in the pressurized container; and/or d. comprises nanovesicles having a size of less than or equal to 500 nm when subjected to 1, 2, 3, 4, 5 or more freeze-thaw cycles; and/or e. is characterized by a polydispersity index of less than or equal to 0.4, when stored one month, two months, three months, six months, twelve months, eighteen months, or twenty-four months at 2-25° C., at 10-25° C., at 15-25° C., at 2-8° C., at 5° C. or at 25° C. in the pressurized container; and/or f. comprises nanovesicles having a size of less than or equal to 500 nm when stored one month, two months, three months, six months, twelve months, eighteen months, twenty-four months, thirty months, or thirty-six months at 2-8° C. or at 5° C. in the pressurized container; and/or g. is characterized by a polydispersity index of less than or equal to 0.4, when stored one month, two months, three months, six months, twelve months, eighteen months, twenty-four months, thirty months, or thirty-six months, at 2-8° C. or at 5° C. in the pressurized container and/or h. is characterized by a polydispersity index of less than or equal to 0.4, when subjected to 1, 2, 3, 4, 5 or more freeze-thaw cycles.

9. The formulation of claim 1, wherein:
the at least one lipophilic component is selected from triglycerides and mixtures thereof;
the at least one surfactant comprises a phospholipid, a lysophospholipid, a ceramide, a mixture thereof, and/or a nonionic surfactant;
the at least one alcohol has 3-5 carbon atoms; and/or
the propellant is propane, isobutane, n-butane, or a mixture thereof.

10. The formulation of claim 1, comprising a total aqueous component in an amount of 50% to 99% (w/w) based on the total weight of the nanoemulsion (a).

11. The formulation of claim 5, wherein the gelling agent is selected from the group consisting of poloxamer, xanthan, bentonite, sodium carboxymethylcellulose, hydroxymethyl cellulose, carbomer, hydroxypropyl cellulose, gellan gum, guar gum, pectin, poly(ethylene)oxide, polycarbophil, alginate, tragacanth, povidone, gelatin, and mixtures thereof.

12. A container or a foam or spray dispenser product comprising a container, comprising the formulation of claim 1.

13. A foam comprising the formulation of claim 1.

14. A cosmetic comprising the formulation of claim 1.

15. A formulation comprising:
(a) a nanoemulsion comprising:
(i) at least one aqueous component;
(ii) a carrier component comprising:
(1) at least one lipophilic component,
(2) at least one surfactant, and
(3) at least one alcohol; and
(b) a propellant,
wherein the formulation is comprised in a pressurized container,
wherein the formulation comprises less than 0.5% (w/w) based on the total weight of the formulation or no fatty alcohol,
wherein the formulation comprises a gelling agent, and
wherein the gelling agent is present in an amount of 0.1% to 10% (w/w) based on the total weight of the formulation.

16. The formulation of claim 15, further comprising an active agent.

17. The formulation of claim 16, wherein the active agent is 5-aminolevulinic acid, a pharmaceutically acceptable salt thereof, or a pharmaceutically acceptable derivative thereof, wherein the pharmaceutically acceptable derivative comprises esters, ethers, thioesters, methyl-thioesters, thioethers, methyl-thioethers methoxy-substituted benzyl ethers, silyl ethers, sulfonates, sulfenates, sulfinates, carbonates, cyclic carbonates, carbamates, cyclic acetals, cyclic ketals, ketones, chiral ketones, hydrazones, enamines and/or enols.

18. A container or a foam or spray dispenser product comprising a container comprising the formulation of claim 15.

19. A foam comprising the formulation of claim 15.

20. A cosmetic comprising the formulation of claim 15.

21. A formulation comprising:
(a) a nanoemulsion comprising:
(i) at least one aqueous component;
(ii) a carrier component comprising:
(1) at least one lipophilic component,
(2) at least one surfactant, and
(3) at least one alcohol; and
(b) a propellant,
wherein the formulation is comprised in a pressurized container,
wherein the formulation comprises less than 0.5% (w/w) fatty alcohol based on the total weight of the formulation or no fatty alcohol; and
wherein the formulation comprises an active agent, and
wherein the active agent is 5-aminolevulinic acid or a pharmaceutically acceptable salt or a pharmaceutically acceptable derivative thereof comprising an ester.

* * * * *